(12) United States Patent
Sastry et al.

(10) Patent No.: US 6,656,471 B1
(45) Date of Patent: Dec. 2, 2003

(54) HIV-SPECIFIC T-CELL INDUCTION

(75) Inventors: K. Jagannadha Sastry, Bastrop, TX (US); Ralph B. Arlinghaus, Bellaire, TX (US); Pramod N. Nehete, Bastrop, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/440,772

(22) Filed: Nov. 16, 1999

Related U.S. Application Data

(60) Provisional application No. 60/108,563, filed on Nov. 16, 1998, and provisional application No. 60/115,175, filed on Jan. 8, 1999.

(51) Int. Cl.$^7$ ................................................ A61K 38/00
(52) U.S. Cl. ............................... 424/188.1; 424/185.1; 424/186.1; 424/187.1; 530/324; 530/325; 530/826
(58) Field of Search ................. 530/324, 325, 530/826; 424/185.1, 186.1, 187.1, 188.1, 282.1, 283.1

(56) References Cited

U.S. PATENT DOCUMENTS

| | | | |
|---|---|---|---|
| 3,791,932 A | 2/1974 | Schuurs et al. | 195/103.5 R |
| 3,949,064 A | 4/1976 | Bornstein et al. | 424/1 |
| 4,174,384 A | 11/1979 | Ullman et al. | 424/8 |
| 4,452,901 A | 6/1984 | Gordon et al. | 436/506 |
| 4,554,101 A | 11/1985 | Hopp | 260/112.5 R |
| 4,596,792 A | 6/1986 | Vyas | 514/21 |
| 4,599,230 A | 7/1986 | Milich et al. | 424/89 |
| 4,601,903 A | 7/1986 | Frasch | 424/92 |
| 4,608,251 A | 8/1986 | Mia | 424/85 |
| 4,683,195 A | 7/1987 | Mullis et al. | 435/6 |
| 4,683,202 A | 7/1987 | Mullis | 435/91 |
| 4,690,915 A | 9/1987 | Rosenberg | 514/2 |
| 4,797,368 A | 1/1989 | Carter et al. | 435/320 |
| 4,800,159 A | 1/1989 | Mullis et al. | 435/172.3 |
| 4,883,750 A | 11/1989 | Whiteley et al. | 435/6 |
| 5,028,592 A | 7/1991 | Lipton | 514/18 |
| 5,139,941 A | 8/1992 | Muzyczka et al. | 435/172.3 |
| 5,199,942 A | 4/1993 | Gillis | 604/4 |
| 5,221,605 A | 6/1993 | Bard et al. | 435/4 |
| 5,238,808 A | 8/1993 | Bard et al. | 435/4 |
| 5,279,721 A | 1/1994 | Schmid | 204/182.8 |
| 5,310,687 A | 5/1994 | Bard et al. | 436/518 |
| 5,620,896 A | 4/1997 | Herrmann et al. | 435/320.1 |
| 5,780,036 A | 7/1998 | Chisari | 424/189.1 |
| 5,958,895 A | 9/1999 | Pachuk et al. | 514/44 |
| 6,271,198 B1 * | 8/2001 | Braisted et al. | 514/2 |

FOREIGN PATENT DOCUMENTS

| | | |
|---|---|---|
| EP | 320308 | 6/1989 |
| EP | 329822 | 8/1989 |
| GB | 2202328 | 9/1988 |
| WO | WO 88/10315 | 12/1988 |
| WO | WO 89/06700 | 7/1989 |
| WO | WO 93/19775 | 10/1993 |
| WO | WO 96/33734 | 10/1996 |

OTHER PUBLICATIONS

Goulder et al., "Novel, cross–restricted, conserved and immunodominant cytotoxic T lymphocyte epitopes in slow progressors in HIV type I infection," *AIDS Res. Hum. Retroviruses,* 12(18):1691–1698, 1996.

Gorse et al., "Recombinant gp160 vaccination schedule and MHC HLA type as factors influencing cellular responses to HIV–1 envelope glycoprotein," *Vaccine,* 13(13):1170–1179, 1995.

Falk et al., "Allele–specific peptide ligand motifs of HLA–C molecules," *Proc. Natl. Acad. Sci. USA,* 90:12005–12009, 1993.

Aichele et al., "Antiviral cytotoxic T cell response induced by in vivo priming with a free synthetic peptide," *J. Exp. Med.,* 171:1815–1820, 1990.

Altman et al., "Phenotypic analysis of antigen–specific T lymphocytes," *Science,* 274:94–96, 1996.

An and Whitton, "A multialent minigene vaccine, containing B–cell, cytotoxic T–lymphocyte, and $T_h$ epitopes from several microbes, induces appropriate responses in vivo and confers protection against more than one pathogen," *J. Virol.,* 71(3):2292–2302, 1997.

Barry et al., "Protection against mycoplasma infection using defined epitopes," *FASEB J.,* 5:2412–2418, 1991.

Berzofsky, "Development of artificial vaccines against HIV using defined epitopes," *FASEB J.,* 5:2412–2418, 1991.

Bevan, "Stimulating killer cells," *Nature,* 342:478–479, 1989.

Bogedain et al., "Specific cytotoxic T lymphocytes recognize the immediate–early transactivator ZTA of Epstein–Barr virus," *J. Virol.,* 69(8):4872–4879, 1995.

Boyson et al., The MHC class I genes of the rhesus monkey, *J. Immunol.* 156:4656–4665, 1996.

(List continued on next page.)

*Primary Examiner*—Jeffrey Stucker
(74) *Attorney, Agent, or Firm*—Fulbright & Jaworski L.L.P.

(57) ABSTRACT

This invention discloses diagnostic, preventative, and treatment therapies of AIDS involving determining whether a subject exhibits an HLA-Cw7-restricted CTL response. Some methods are directed to the use of HLA-Cw7 as a genetic marker for long-term non-progression and amenability to treatment therapies. Diagnostic methods include a method for predicting long term non-progression in an HIV-infected subject. Preventative and treatment methods encompass determining whether a subject exhibits or can exhibit an HLA-Cw7-restricted CTL response. They also encompass ways of eliciting such a response, if necessary. Furthermore, some of the methods involve administering one or more HIV polypeptides or peptides, or polynucleotides encoding them, as a treatment therapy to prevent the development of AIDS.

25 Claims, 27 Drawing Sheets

OTHER PUBLICATIONS

Braciale et al., "Antigen presentation pathways to class I and class II MHC–restricted T lymphocytes," *Immunol. Rev.*, 98:95–114, 1987.

Carmichael et al., "Quantitative analysis of the human immunodeficiency virus Type I (HIV–1)–specific cytotoxic T lymphocyte (CTL) response at different stages of HIV–1 infection: differential CTL responses to HIV–1 and Epstein–Barr virus in late disease," *J. Exp. Med.*, 177:249–256, 1993.

Casement et al., "Cross–reactive cytotoxic T lymphocytes induced by V3 loop synthetic peptides from different strains of human immunodeficiency virus type I," *Virology*, 21(1):261–67, 1995.

Chopra et al., "Cloning and expression of putative cytotonic enterotoxin–encoding genes from *Aeromonas hydrophila*," *Gene* 139:87–91, 1994.

Chopra et al., Molecular and biochemical characterization of a heat–labile cytotonic enterotoxin from *Aeromonas hydrophila, Microbial Path.* 21:357–377, 1996.

Ciernik et al., "Induction of cytotoxic T lymphocytes and antitumor immunity with DNA vaccines expressing single T–cell epitopes," *J. Immunol.*, 156:2369–2375, 1996.

Clerget–Raslain et al., "Specificity of anti–peptide antibodies elicited against synthetic peptides mimicking conserved regions of HIV1 envelope glycoprotein," *Res. Virol.*, 142:423–438, 1991.

Agren et al., "Genetically engineered nontoxic vaccine adjuvant that combines B cell targeting with immunomodulation by cholera toxin A1 subunit," *J. Immunol.* 158:3936–3946, 1997.

Dadaglio et al., "Epitope recognition of conserved HIV envelope sequences by human cytotoxic T lymphocytes," *J. Immunol.*, 147:2302–2309, 1991.

Dai et al., "Mutation of human immonudeficiency virus type 1 at amino acid 585 on gp41 results in loss of killing by CD8+ A24–restricted cytotoxic T lymphocytes," *J. Virol.*, 66:3151–3154, 1992.

De Rossi, et al., "Synthetic peptides from the principal neutralizing domain of human immunodeficiency virus type 1 (HIV–1) enhance HIV–1 infection through a CD4–dependent mechanism," *Virology*, 185:187–196, 1991.

Del Guercio et al., "Potent immunogenic short linear peptide constructs composed of B cell epitopes and Pan DR T helper epitopes (PADRE) for antibody responses in vivo," Vaccine 15:441–448, 1997.

Deres et al., "In vivo priming of virus specific cytotoxic T lymphocytes with synthetic lipopeptide vaccine," *Nature*, 342:561–564, 1989.

Dupuis et al., "Characterization of HLA–A*0201–restricted cytotoxic T cell epitopes in conserved regions of the HIV type 1 gp160 protein," *J. Immunol.*, 155:2232–2239, 1995.

Falk et al., "Expression of HLA–C molecules confers target cell resistance to some non–major histocompatibility complex–restricted T cells in a manner analogous to allospecific natural killer cells," *J. Exp. Med.*, 182:1005–1018, 1995.

Ferguson et al., "Amino–acid residues involves in biological functions of the cytotoxic enterotoxin from *Aeromonas hydrophila*," Gene 156:79–83, 1995.

Ferguson et al., "Hyperproduction, purification and mechanism of action of the cytotoxic enterotoxin produced by *Aeromonas hydrophila*," *Infec. Immun.*, 65:4299–4308, 1997.

Flotte et al., "An improved system for packaging recombinant adeno–associated virus vectors capable of in vivo transduction," *Gene Therapy*, 2:29–37, 1995.

Fuller and Haynes, "A qualitative progression in HIV type 1 glycoprotein 120–specific cytotoxic cellular and humoral immune responses in mice receiving a DNA–based glycoprotein 120 vaccine," *AIDS Res. Hum. Retroviruses*, 11:1433–1441, 1994.

Gallichan and Rosenthal, "Long–lived cytotoxic T lymphocyte memory in mucosal tissues after mucosal but not systemic immunication," *J. Exp. Med.* 181:1879–1890, 1996.

Gussow et al., "Isolation, expression and the primary structure of HLA–Cw1 and HLA–Cw2 genes: evolutionary aspects," *Immunogenetics*, 25:313–322, 1987.

Gao et al., "Priming of influenza virus–specific cytotoxic T lymphocytes vivo by short synthetic peptides," *J. Immun.*, 147(10):3268–3273.

Imaoka, et al., "Nasal immunization of nonhuman primates with simian immunodeficiency virus $p55^{gag}$ and cholera toxin adjuvant induces Th1/Th2 help for virus specific immune responses in reproductive tissues," *J. Immunol.*, 161:5952–5958, 1998.

Ishioka et al., "Utilization of MHC class I transgenic mice for development of minigene DNA vaccines encoding multpile HLA–restricted CTL epitopes," *J. Immunol.*, 162:3915–3925, 1999.

Jassoy et al., "Detection of a vigourous HIV–1–specific cytotoxic T lymphocyte response in cerebrospinal fluid from infected persons with AIDS dementia complex," *J. Immunol.*, 149:3113–3119, 1992.

Johnson et al., "Identification of overlapping HLA class I–restricted cytotoxic epitopes in a conserved region of the human immunodeficiency virus type 1 envelope glycoprotein: definition of minimum epitopes and analysis of the effects of sequence variation," *J. Exp. Med.*, 175:961–971, 1992.

Johnson et al., "Recognition of a highly conserved region of human immunodeficiency virus type 1 gp120 by an HLA–Cw4–restricted cytotoxic T–lymphocyte clone," *J. Virol.*, 67(1):438–445, 1993.

Kast et al., "Protection against lethal Sendai virus infection by in vivo priming of virus–specific cytotoxic T lymphocytes with a free synthetic peptide," *Proc. Nat'l Acad. Sci. USA*, 88:2283, 1991.

Keusch et al., "Classification of enterotoxins on the basis of activity in cell culture," *J. Infect. Dis.* 131(1):58–63, 1973.

Klein et al., "Kinetics of gag–specific cytotoxic T–lymphocyte responses during the clinical course of HIV–1 infection: a longitudinal analysis of rapid progressors and long–term asymptomatics," *J. Exp. Med.*, 181:1365–1372, 1995.

Koup et al., "Temporal association of cellular immune responses with the initial control of viremia in primary human immunodeficiency virus type 1 syndrome," *J. Virol.*, 68:4650–4655, 1994.

Levy, "Pathogenesis of HIV infection," *Microbiol. Rev.*, 57:185–253, 1993.

Littaua et al., "An HLA–C–restricted CD8+ cytotoxic T–Lymphocyte clone recognizes a highly conserved epitope on human immunodeficiency virus type 1 gag," *J. Viol.*, 65:4051–4056, 1991.

Lu et al., "Use of DNAs expressing HIV–1 Env and non-infectious HIV–1 particles to raise antibody responses in mice," *Virology*, 209:147–154, 1995.

Merino et al., "Emerging Pathogens: Aeromonas spp.," *Int'l. J. Food. Microbiol.* 28:157–168, 1995.

Modrow et al., "Computer–assisted analysis of envelope protein sequences of seven human immunodeficiency virus isolates: prediction of antigenic epitopes in conserved and variable regions," *J. Virol.* 61:570–578, 1987.

Mortara et al., "Type 1 CD4+ T–cell help is required for induction of antipeptide multispecific cytotoxic T lymphocytes by a lipopeptidic vaccine in rhesus macaques," *J. Virol.* 73:4447–4451, 1999.

Musey et al., "Cytotoxic–T–cell responses, viral load, and disease progression in early human immunodeficiency virus type 1 infection," *New Engl. J. Med.,* 337(18):1267–1274, 1997.

Muzyczka, "Use of adeno–associated virus as a general transduction vector for mammalian cells," *Curr. Top. Microbiol. Immunol.,* 158:97–129, 1992.

Nehete et al., "Studies on V3–specific cross–reactive T–cell responses in chimpanzees chronically infected with HIV-1$_{IIIB}$," *AIDS* 9:567–572, 1995.

Nehete et al., "Induction of human immunodeficiency virus–specific T cell responses in rhesus monkeys by synthetic peptides from gp160," *AIDS Res. Hum. Retroviruses,* 9:235–240, 1993.

Nehete et al., "Studies on in vivo induction of HIV–1 envelope–specific cytotoxic T lymphocytes by synthetic peptides from V3 loop region of HIV–1 IIIB gp120," *Cell. Immunol.,* 160:217, 1995.

Nehete et al., "Cross–reactive T–cell proliferative responses to V3 peptides corresponding to different geographical HIV–1 isoaltes in HIV–seropositive individuals," *J. Clin. Immunol.,* 16(2):115–124, 1996.

Nehete et al., "Presence of HLA–C–restricted cytotoxic T–lymphocyte responses in long–term nonprogressors infected with human immunodeficiency virus," *Vir. Immunol.,* 11(3):119–129, 1998.

Nehete et al., "A synthetic peptide from the first conserved region in the envelope protein gp160 is a strong T–cell epitope in HIV–infected chimpanzees and humans," *Vir. Immunol.,* 11(3):147–158, 1998.

Nehete et al., "Use of helper T cell–inducing peptides from conserved regins in HIV–1 env in a noncovalent mixture with a CTL–inducing V3–loop peptide for in vivo induction of long–lasting systemic CTL response," *Vir. Immunol.,* 7(4):189–197, 1994.

Pantaleo et al., "Major expansion of CD8+ T cells with a predominant Vβ usage during the primary immune response to HIV," *Nature,* 370:463–467, 1994.

Peterson et al., "Cholera toxin B subunit activates arachidonic acid metabolism," *Infect. Immunol.* 67:794–799, 1999.

Picard et al., "A 2–year follow–up of an anti–HIV immune reaction in HIV–1 gp–160–immunized healthy seronegative humans: evidence for persistent cell–mediated immunity," *J. Acquired Immune Defic. Syndr.,* 5:539–546., 1992.

Pontesilli et al., "HIV–specific lymphoproliferative responses in asymptomatic HIV–infected individuals," *Clin. Exp. Immunol.,* 100:419–424, 1995.

Porgador et al., Intranasal immunization with CTL epitope peptides from HIV–1 or ovalbumin and the mucosal adjuvant cholera toxin induces peptide–specific CTLs and protection against tumor development in vivo, *J. Immunol.,* 158:834–841, 1997.

Roos et al., "T cell function in vitro is an independent progression marker for AIDS to human immunodeficiency virus–infected asymptomatic subjects," *J. Infect. Dis.,* 171:531–536, 1995.

Rosenberg et al., *Science,* "Vigorous HIV–1–specific CD4+ T cell responses associated with control of viremia," 278:1447–1450, 1997.

Rowland–Jones et al., "HIV–specific cytotoxic T–cell activity in an HIV–exposed but uninfected infant," *Lancet,* 341:860–861, 1993.

Rowland–Jones et al., "HIV–specific cytotoxic T–cells in HIV–exposed but uninfected Gambian women," *Nature Med.,* 1:59–64, 1995.

Sarkar et al., "Studies on in vivo induction of cytotoxic T lymphocyte responses by synthetic peptides from E6 and E7 oncoproteins of human papillomavirus type 16," *Viral Imm.,* 8:165–174, 1995.

Sastry and Arlinghaus, "Identification of T–cell epitopes without B–cell activity in the first and second conserved regions of the HIV Env protein," *AIDS,* 5:699–707, 1991.

Sastry et al., "Rapid in vivo induction of HIV–specific CD8+ cytotoxic T lymphocytes by a 15–amino acid unmodified free peptide from the immunodominant V3–loop of GP120," *Virology,* 188:502–509, 1992.

Schendel et al., "Cytotoxic T lymphocytes show HLA–C–restricted recognition of EBV–bearing cells and allorecognition of HLA class I molecules presenting self–peptides," *J. Immunol.,* 149:2406–2416, 1992.

Schrier et al., "T cell recognition of HIV synthetic peptides in a natural infection," *J. Immunol.,* 142:1166–1176.

Sedegah et al., "Protection against malaria by immunization with plasmid DNA encoding circumsporozoite protein," *Immunology,* 91:9866–9870, 1994.

Takahashi et al., Specific lysis of human immunodeficiency virus type 1–infected cells by a HLC–A3.1–restricted CD8+ sytotoxic t–lymphocyte clone that recognizes a conserved peptide sequence within the gp41 subunit of the envelope protein, *Proc. Natl. Acad. Sci. USA,* 88:10277–10281, 1991.

Ulmer et al., "Heterologous protection against influenza by injection of DNA encoding a viral protein," *Science,* 259:1745–1749, 1993.

Unanue & Cerottini, "Antigen presentation," *FASEB J.* 3:2496–2502, 1989.

van den Eynde et al., "A new family of genes coding for an antigen recognized by autologous cytolytic T lymphocytes on a human melanoma," *J. Exp. Med.,* 182:689–698, 1995.

Wang et al., "Simultaneous induction of multiple antigen–specific cytotoxic T lymphocytes in nonhuman primates by immunization with a mixture of four plasmodium falciparum DNA plasmids," *Infec. Imm.,* 66(9):4193–4202, 1998.

Xiang et al., "Vaccination with a plasmid vector carrying the rabies virus glycoprotein gene induces protective immunity against rabies virus," *Virology,* 199:132–140, 1994.

Xu et al., "Role of a cytotoxic enterotoxin in Aeromonas–mediated infections: development of transposon and isogenic mutants," *Infect. Immun.* 66:3501–3509, 1998.

Yamada et al., "INcidence and clinical symptoms of Aeromonas–associated travellers' diarrhoea in Tokyo," *Epidemiol. & Infect.* 119:121–126, 1997.

Yasutomi et al., "Simian immunodeficiency virus–specific cytoxic T–lymphocyte induction through DNA vaccination of rhesus monkeys," *J. Virol.,* 70:678–681, 1996.

Yokoyama et al., "DNA immunization confers protection against lethal lymphocytic choriomeningitis virus infection," *J. Viool.,* 69(4):2684–2688, 1995.

Zemmour and Parham, "HLA class I neucleotide sequences, 1992," *Immunogenetics,* 37:239–250, 1993.

\* cited by examiner

SEQUENCE LISTING

<160> NUMBER OF SEQ ID NOS: 40

<210> SEQ ID NO 1
<211> LENGTH: 11
<212> TYPE: PRT
<213> ORGANISM: Human immunodeficiency virus type 1

<400> SEQUENCE: 1

Val Tyr Tyr Gly Val Pro Val Trp Lys Glu Ala
 1               5                  10

<210> SEQ ID NO 2
<211> LENGTH: 11
<212> TYPE: PRT
<213> ORGANISM: Human immunodeficiency virus type 1

<400> SEQUENCE: 2

Val Tyr Tyr Gly Val Pro Val Trp Lys Asp Ala
 1               5                  10

<210> SEQ ID NO 3
<211> LENGTH: 11
<212> TYPE: PRT
<213> ORGANISM: Human immunodeficiency virus type 1

<400> SEQUENCE: 3

Val Tyr Ser Gly Val Pro Val Trp Glu Asp Ala
 1               5                  10

<210> SEQ ID NO 4
<211> LENGTH: 13
<212> TYPE: PRT
<213> ORGANISM: Human immunodeficiency virus type 1

<400> SEQUENCE: 4

Leu Trp Asp Gln Ser Leu Lys Pro Cys Val Lys Leu Thr
 1               5                  10

<210> SEQ ID NO 5
<211> LENGTH: 13
<212> TYPE: PRT
<213> ORGANISM: Human immunodeficiency virus type 1

<400> SEQUENCE: 5

Leu Trp Asp Glu Ser Leu Lys Pro Cys Val Lys Leu Thr
 1               5                  10

<210> SEQ ID NO 6
<211> LENGTH: 13
<212> TYPE: PRT
<213> ORGANISM: Human immunodeficiency virus type 1

<400> SEQUENCE: 6

Leu Trp Asp Gln Ser Leu Lys Pro Cys Val Gln Met Thr
 1               5                  10

<210> SEQ ID NO 7
<211> LENGTH: 13
<212> TYPE: PRT
<213> ORGANISM: Human immunodeficiency virus type 1
<220> FEATURE:
<221> NAME/KEY: UNSURE
<222> LOCATION: (4)
<223> OTHER INFORMATION: X = any

<400> SEQUENCE: 7

Leu Trp Asp Xaa Ser Leu Lys Pro Cys Val Lys Leu Thr
 1               5                  10

<210> SEQ ID NO 8
<211> LENGTH: 13
<212> TYPE: PRT
<213> ORGANISM: Human immunodeficiency virus type 1

<400> SEQUENCE: 8

Ser Val Ile Thr Gln Ala Cys Ser Lys Val Ser Phe Glu
 1               5                  10

<210> SEQ ID NO 9
<211> LENGTH: 13
<212> TYPE: PRT
<213> ORGANISM: Human immunodeficiency virus type 1

<400> SEQUENCE: 9

Ser Ala Ile Thr Gln Ala Cys Ser Lys Val Ser Phe Glu
 1               5                  10

<210> SEQ ID NO 10
<211> LENGTH: 13
<212> TYPE: PRT
<213> ORGANISM: Human immunodeficiency virus type 1

<400> SEQUENCE: 10

Ser Ala Ile Thr Gln Ala Cys Ser Lys Val Ser Phe Asp
 1               5                  10

<210> SEQ ID NO 11
<211> LENGTH: 13
<212> TYPE: PRT
<213> ORGANISM: Human immunodeficiency virus type 1

<400> SEQUENCE: 11

Ser Val Ile Lys Gln Ala Cys Ser Lys Ile Ser Phe Asp
 1               5                  10

<210> SEQ ID NO 12
<211> LENGTH: 13
<212> TYPE: PRT
<213> ORGANISM: Human immunodeficiency virus type 1

<400> SEQUENCE: 12

Ser Thr Ile Thr Gln Ala Cys Ser Lys Val Ser Trp Asp
 1               5                  10

<210> SEQ ID NO 13
<211> LENGTH: 13
<212> TYPE: PRT
<213> ORGANISM: Human immunodeficiency virus type 1

<400> SEQUENCE: 13

Ser Thr Ile Lys Gln Ala Cys Ser Lys Val Asn Phe Asp
 1               5                  10

<210> SEQ ID NO 14
<211> LENGTH: 13
<212> TYPE: PRT
<213> ORGANISM: Human immunodeficiency virus type 1
<220> FEATURE:
<221> NAME/KEY: UNSURE

```
<222> LOCATION: (4)
<223> OTHER INFORMATION: X = any

<400> SEQUENCE: 14

Thr Thr Ile Xaa Gln Ala Cys Ser Lys Val Ser Phe Glu
 1               5                  10

<210> SEQ ID NO 15
<211> LENGTH: 13
<212> TYPE: PRT
<213> ORGANISM: Human immunodeficiency virus type 1
<220> FEATURE:
<221> NAME/KEY: UNSURE
<222> LOCATION: (2)
<223> OTHER INFORMATION: X = any

<400> SEQUENCE: 15

Ser Xaa Ile Lys Gln Ala Cys Ser Lys Val Ser Phe Glu
 1               5                  10

<210> SEQ ID NO 16
<211> LENGTH: 13
<212> TYPE: PRT
<213> ORGANISM: Human immunodeficiency virus type 1

<400> SEQUENCE: 16

Gly Thr Gly Pro Cys Thr Asn Val Ser Thr Val Gln Cys
 1               5                  10

<210> SEQ ID NO 17
<211> LENGTH: 13
<212> TYPE: PRT
<213> ORGANISM: Human immunodeficiency virus type 1

<400> SEQUENCE: 17

Gly Thr Gly Pro Cys Lys Asn Val Ser Thr Val Gln Cys
 1               5                  10

<210> SEQ ID NO 18
<211> LENGTH: 13
<212> TYPE: PRT
<213> ORGANISM: Human immunodeficiency virus type 1

<400> SEQUENCE: 18

Gly Thr Gly Pro Cys His Asn Val Ser Thr Val Gln Cys
 1               5                  10

<210> SEQ ID NO 19
<211> LENGTH: 13
<212> TYPE: PRT
<213> ORGANISM: Human immunodeficiency virus type 1
<220> FEATURE:
<221> NAME/KEY: UNSURE
<222> LOCATION: (6)
<223> OTHER INFORMATION: X = any

<400> SEQUENCE: 19

Gly Thr Gly Leu Cys Xaa Asn Ile Thr Val Val Thr Cys
 1               5                  10

<210> SEQ ID NO 20
<211> LENGTH: 25
<212> TYPE: PRT
<213> ORGANISM: Human immunodeficiency virus type 1

<400> SEQUENCE: 20
```

-continued

Phe Leu Gly Phe Leu Gly Ala Ala Gly Ser Thr Met Gly Ala Ala Ser
 1               5                  10                  15

Leu Thr Leu Thr Val Gln Ala Arg Gln
            20                  25

<210> SEQ ID NO 21
<211> LENGTH: 25
<212> TYPE: PRT
<213> ORGANISM: Human immunodeficiency virus type 1

<400> SEQUENCE: 21

Phe Leu Gly Phe Leu Gly Ala Ala Gly Ser Thr Met Gly Ala Ala Ser
 1               5                  10                  15

Ile Thr Leu Thr Val Gln Ala Arg Gln
            20                  25

<210> SEQ ID NO 22
<211> LENGTH: 25
<212> TYPE: PRT
<213> ORGANISM: Human immunodeficiency virus type 1
<220> FEATURE:
<221> NAME/KEY: UNSURE
<222> LOCATION: (17)
<223> OTHER INFORMATION: X = any

<400> SEQUENCE: 22

Phe Leu Gly Phe Leu Gly Ala Ala Gly Ser Thr Met Gly Ala Ala Ser
 1               5                  10                  15

Xaa Thr Leu Thr Val Gln Ala Arg Gln
            20                  25

<210> SEQ ID NO 23
<211> LENGTH: 25
<212> TYPE: PRT
<213> ORGANISM: Human immunodeficiency virus type 1

<400> SEQUENCE: 23

Ile Phe Gly Phe Leu Gly Ala Ala Gly Ser Thr Met Gly Ala Ala Ser
 1               5                  10                  15

Leu Thr Leu Thr Val Gln Ala Arg Gln
            20                  25

<210> SEQ ID NO 24
<211> LENGTH: 25
<212> TYPE: PRT
<213> ORGANISM: Human immunodeficiency virus type 1

<400> SEQUENCE: 24

Phe Leu Gly Phe Leu Gly Ala Ala Gly Ser Thr Met Gly Ala Ala Ala
 1               5                  10                  15

Thr Ala Leu Thr Val Gln Ala Arg Gln
            20                  25

<210> SEQ ID NO 25
<211> LENGTH: 25
<212> TYPE: PRT
<213> ORGANISM: Human immunodeficiency virus type 1
<220> FEATURE:
<221> NAME/KEY: UNSURE
<222> LOCATION: (17)..(18)
<223> OTHER INFORMATION: X = any

<400> SEQUENCE: 25

Phe Leu Gly Phe Leu Gly Ala Ala Gly Ser Thr Met Gly Ala Ala Ser

-continued

```
               1               5                  10                 15
Xaa Xaa Leu Thr Val Gln Ala Arg Gln
                   20                  25

<210> SEQ ID NO 26
<211> LENGTH: 12
<212> TYPE: PRT
<213> ORGANISM: Human immunodeficiency virus type 1

<400> SEQUENCE: 26

Tyr Leu Arg Asp Gln Gln Leu Leu Gly Ile Trp Gly
 1               5                  10

<210> SEQ ID NO 27
<211> LENGTH: 12
<212> TYPE: PRT
<213> ORGANISM: Human immunodeficiency virus type 1

<400> SEQUENCE: 27

Tyr Leu Lys Asp Gln Gln Leu Leu Gly Ile Trp Gly
 1               5                  10

<210> SEQ ID NO 28
<211> LENGTH: 12
<212> TYPE: PRT
<213> ORGANISM: Human immunodeficiency virus type 1

<400> SEQUENCE: 28

Tyr Leu Lys Asp Gln Lys Phe Leu Gly Leu Trp Gly
 1               5                  10

<210> SEQ ID NO 29
<211> LENGTH: 12
<212> TYPE: PRT
<213> ORGANISM: Human immunodeficiency virus type 1
<220> FEATURE:
<221> NAME/KEY: UNSURE
<222> LOCATION: (3)
<223> OTHER INFORMATION: X = any

<400> SEQUENCE: 29

Tyr Leu Xaa Asp Gln Gln Leu Leu Gly Leu Trp Gly
 1               5                  10

<210> SEQ ID NO 30
<211> LENGTH: 12
<212> TYPE: PRT
<213> ORGANISM: Human immunodeficiency virus type 1
<220> FEATURE:
<221> NAME/KEY: UNSURE
<222> LOCATION: (3)
<223> OTHER INFORMATION: X = any

<400> SEQUENCE: 30

Tyr Leu Xaa Asp Gln Gln Leu Leu Gly Ile Trp Gly
 1               5                  10

<210> SEQ ID NO 31
<211> LENGTH: 12
<212> TYPE: PRT
<213> ORGANISM: Human immunodeficiency virus type 1

<400> SEQUENCE: 31

Tyr Leu Arg Asp Gln Gln Leu Leu Gly Leu Trp Gly
 1               5                  10
```

```
<210> SEQ ID NO 32
<211> LENGTH: 12
<212> TYPE: PRT
<213> ORGANISM: Human immunodeficiency virus type 1

<400> SEQUENCE: 32

Tyr Leu Glu Ser Gln Gln Leu Leu Gly Leu Trp Gly
 1               5                  10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 33

Tyr Leu Arg Asp Gln Gln Leu Leu Gly Ile Trp Gly Cys
 1               5                  10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 34

Tyr Leu Lys Asp Gln Gln Leu Leu Gly Ile Trp Gly Cys
 1               5                  10

<210> SEQ ID NO 35
<211> LENGTH: 25
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 35

Phe Leu Gly Phe Leu Gly Ala Ala Gly Ser Thr Met Gly Ala Ala Ser
 1               5                  10                  15

Leu Thr Leu Thr Val Gln Ala Arg Cys
             20                  25

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 36

Cys Arg Ile Lys Gln Ile Ile Asn Met Trp Gln Gly Val Gly Lys Ala
 1               5                  10                  15

Met Tyr Ala

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence:  Synthetic
```

-continued

Peptide

<400> SEQUENCE: 37

Ser Thr Arg Thr Pro Glu Asp Ser Asn Ser Leu Gly Thr
 1               5                  10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 38

Ser Ala Ile Thr Gln Ala Cys Ser Lys Val Thr Phe Glu
 1               5                  10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 39

Gly Thr Gly Pro Cys Lys Asn Val Ser Ser Val Gln Cys
 1               5                  10

<210> SEQ ID NO 40
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 40

Phe Leu Gly Val Leu Ser Ala Ala Gly Ser Thr Met Gly Ala Ala Ser
 1               5                  10                  15

Leu Thr Leu Thr Val Gln Ala Arg Gln
            20                  25

HIV-SPECIFIC T-CELL INDUCTION

This application claims priority to U.S. provisional patent application Serial No. 60/108,563, filed on Nov. 16, 1998, and U.S. provisional patent application Serial No. 60/115,175, filed on Jan. 8, 1999, both of which are herein incorporated by reference.

BACKGROUND OF THE INVENTION

1. Field of the Invention

The present invention relates generally to the fields of diagnosis and treatment to prevent the onset of AIDS. More particularly, it concerns the use HIV peptides and HLA-restricted T-cell responses in both prediction of long-term non-progression of AIDS and prevention of AIDS.

2. Description of Related Art

During progressive human immunodeficiency virus type 1 (HIV-1) infection, the virus-specific immune responses of an infected subject gradually deteriorate, leading to the development of acquired immunodeficiency syndrome (AIDS). Most infected patients do not exhibit overt clinical manifestations of the disease for six to ten years following initial infection. Reports indicate, however, that approximately 5% of HIV-1 infected persons remain free of disease for ten or more years. (Haynes, 1996; Munoz, 1995; Rinaldo, 1995; Rowland-Jones, 1995; Rowland-Jones, 1993; Clerici, 1991; Lifson, 1991). Such a person, termed a long-term non-progressor (LTNP), exhibits lower viral loads and stable $CD4^+$ cell counts.

The induction of a cytotoxic T-lymphocyte (CTL) response constitutes a significant defense mechanism against viral infections; occasionally, a virus-specific CTL response can render full protection without a concomitant antibody response (Sastry 1992; Bevan, 1989; Lukacher, 1984). Recent studies suggest the importance of cell-mediated immunity (CMI) for maintenance of disease-free status in an LTNP and in individuals belonging to high-risk groups (Rosenberg, 1997; Haynes, 1996; Munoz, 1995; Rinaldo, 1995; Roos, 1995; Rowland-Jones, 1995; Koup, 1994; Pantaleo, 1994; Rowland-Jones, 1993; Picard, 1992; Clerici, 1991; Lifson, 1991). Importantly, a small number of apparently uninfected children born to HIV-infected mothers and HIV-exposed but uninfected Gambian women have demonstrated HIV-specific cytotoxic T lymphocyte (CTL) responses (Rowland-Jones, 1995; Rowland-Jones, 1993). Also, Rinaldo et al reported that both high levels of anti-HIV-1 memory CTL activity and low viral loads are associated with the lack of disease in HIV-1-infected LTNPs.

The immune system may effectively eliminate virus-infected cells during the clinical course of HIV-1 infection using virus-specific major histocompatibility complex (MHC) class-I restricted CTL activity (Koup, 1994). The above evidence suggests that HIV-1-specific CTL activity is important for controlling viral spread during the clinical course of HIV-1 infection (Klein, 1995; Koup, 1994), for maintaining low levels of viral load during the asymptomatic phase (Musey, 1997; Rinaldo, 1995; Koup, 1994; Walker, 1987), and possibly for complete elimination of virus-infected cells, as implied from the observation of HIV-exposed, but virus-negative, children and women (Rowland-Jones, 1995; Rowland-Jones, 1993). Furthermore, observations from cross-sectional studies have shown the absence, or severely decreased levels, of HIV-1-specific CTL responses during advanced stages of HIV-1 infection (Carmichael, 1993). Therefore, researchers have focused on identifying virus-specific CTL epitopes.

The induction of specific CTL responses in the context of human MHC class I antigens has been demonstrated by many investigators with respect to HLA-A and HLA-B. HLA-A and -B act as strong transplantation antigens and as restriction molecules for recognition of foreign antigens by CTLs (Dill, 1988; McMichael, 1977). In contrast, little is known about the functional properties of the third class I antigen, HLA-C. HLA-C antigens are encoded by a DNA sequence that is closely related to the sequences encoding HLA-A and -B and lies between them. HLA-C antigens are expressed on lymphoid cells, although to a lesser extent (approximately 10%) than either HLA-A or -B (Schendel, 1992; Gasson, 1987; Sodoyer, 1984).

Recent reports suggest that expression of HLA-C confers protection against lysis by natural killer (NK) cells and also by non-MHC-restricted effector T cells (Falk, 1995; Falk, 1993). In particular, expression of Cw7 was demonstrated to govern directly resistance to lysis against both these types of effector populations (Falk, 1995).

Typically, induction of virus-specific CTLs can be effected by infection with a virus or recombinant virus that expresses a viral gene product. The viral gene product is processed and presented as a peptide on the surface of infected cells in association with an MHC class I molecule for recognition by the CTL (Unanue, 1989; Branciale, 1987).

Additionally, research efforts have concentrated on identifying and characterizing HIV peptides that elicit a viral-specific CTL response. Townsend et al. illustrated the concept of using T-cell epitopes in proteins as vaccine candidates when their group demonstrated the use of short synthetic peptides from influenza nucleoprotein as epitopes for CTL responses. The inventors and others have reported using synthetic peptides to generate virus-specific CTLs in vivo (Kast, 1991; Aichele, 1990; Deres, 1989; Sastry, 1992; Sastry, 1994; Casement, 1995) against influenza, lymphocytic choriomenengitis, Sendai virus and HIV. HIV-infected patients or humans and mice immunized with HIV proteins exhibit a specific CTL response against various HIV gene products (Chenciner, 1989; Tsubota, 1989; Nixon, 1988; Walker, 1988; Plata, 1987; Walker, 1987).

The identification and characterization of additional HIV-specific HLA haplotypes and HIV peptides capable of inducing a specific CTL response would be useful for the diagnosis and treatment of AIDS, particularly if the haplotypes were related to the disease-free status of LTNPs and to peptides from highly conserved HIV sequences.

SUMMARY OF THE INVENTION

The invention generally relates to diagnostic, preventative, and treatment therapies of AIDS. The present invention provides a method of predicting long-term non-progression in an HIV-infected patient. The invention also provides a method of preventing AIDS in both infected and uninfected subjects. It is based on the observation that an HLA-C-specific CTL response can be demonstrated against some HIV envelope peptides.

The present invention first provides a method for predicting long-term non-progression in an HIV-infected patient by determining whether the patient demonstrates an HLA-Cw7 CTL response against a target cell. In one embodiment, the patient is infected with, or at risk of infection by, HIV-1. Methods of assaying for the existence of an HLA-Cw7-restricted CTL response comprise obtaining cells from a patient and exposing them to target cells that express the HLA-Cw7 haplotype. The invention is understood to include cells obtained from peripheral blood mononuclear cells (PMBC), mucosal lymphocytes, lymph node cells, and spleen cells. In another embodiment, the PMBCs are stimulated with phytohemagglutinin, anti-CD3 antibody, or HIV antigens prior to exposing them to target cells.

An HIV-infected subject may be tested for an HLA-Cw7-restricted CTL response or possession of the HLA-Cw7 haplotype. The CTL response also can include CD4- and CD8-expressing (CD4$^+$ and CD8$^+$) cells. The method for detecting an HLA-Cw7 restricted CTL response uses target cells that include cells from an autologous B cell line, dendritic cells, or MHC-matched cells.

The CTL response can be assayed by lysis of the target cell, which could be labeled using [$^{51}$Cr]sodium chromate, or by production of γ-interferon, or by tetramer assay.

In another embodiment, the method of the present invention provides a target cell that presents at least an HIV polypeptide, which includes the HIV envelope (env) polypeptide or the gag polypeptide, in addition to HIV polypeptide fragments thereof. In a preferred embodiment, the polypeptide is gp160, or fragments thereof. In further embodiments, the invention predicts long-term non-progression of AIDS by using a target cell that presents a synthetic peptide whose amino acid sequence is derived from an HIV gene product such as a synthetic peptide, which can be from 11 to 25 residues in length. In additional embodiments, the peptide sequences include YL(R/K)DQQLLGIWGC (SEQ ID NO:33 or SEQ ID NO:34), FLGFLGAAGSTMGAASLTLTVQARQ (SEQ ID NO:20), or VYYGVPVWKEA (SEQ ID NO:1).

Furthermore, the present invention includes the delivery of HIV peptides to the target cell by an expression construct that comprises a polynucleotide sequence encoding at least one HIV peptide under the transcriptional control of a promoter. In some embodiments, the expression vector is a viral vector. Such a viral vector can be from any virus selected from a group consisting of vaccinia virus, adenovirus, herpesvirus, retrovirus, adeno-associated virus and lentivirus.

The present invention next provides a method of preventing an HIV-infected subject from developing AIDS by determining whether the patient expresses HLA-Cw7 and demonstrates an HLA-Cw7-restricted, HIV-specific CTL response; if such a response is exhibited, the patient is administered a composition that contains an HIV polypeptide that is also an HIV CTL epitope. Alternatively, the methods of the invention can be practiced by determining whether the HIV-infected subject has an HLA-Cw7 haplotype. The method is understood to encompass patients who are infected with HIV-1. A composition of the claimed invention includes HIV polypeptides such as the env polypeptide, the gag polypeptide, and fragments of either. Furthermore, the HIV polypeptide of the claimed invention further is understood to include a synthetic peptide whose sequence is derived from HIV gene products. Such a synthetic peptide can be from 11 to 25 residues in length and could include sequences such as YL(R/K)DQQLLGIWGC (SEQ ID NO:33 or SEQ ID NO:34), FLGFLGAAGSTMGAASLTLTVQARQ (SEQ ID NO:20), or VYYGVPVWKEA (SEQ ID NO:1). The method also could include administering a plurality of HIV polypeptides. This plurality of HIV peptides could include 2 or more different peptides containing the sequences YL(R/K)DQQLLGIWGC (SEQ ID NO:33 or SEQ ID NO:34), FLGFLGAAGSTMGAASLTLTVQARQ (SEQ ID NO:20), or VYYGVPVWKEA (SEQ ID NO:1). Alternatively, the method could include administering one or more synthetic peptides from 11 to 25 residues in length that include sequences such as YL(R/K)DQQLLGIWGC (SEQ ID NO:33 or SEQ ID NO:34), FLGFLGAAGSTMGAASLTLTVQARQ (SEQ ID NO:20), VYYGVPVWKEA (SEQ ID NO:1), LWDQSLKPCVKLT (SEQ ID NO:4), SVITQACSKVSFE (SEQ ID NO:8), or GTGPCTNVSTVQC (SEQ ID NO:16). A plurality of peptides that comprises, two, three, four, five or all six of these sequences is included within the methods of the present invention. It is further contemplated that the sequences may also be included in peptides that have additional residues flanking one or more ends of the sequences. For example, the peptide FLGFLGAAGSTMGAASLTLTVQARC (SEQ ID NO:35) falls within the scope of the present invention.

The composition containing an HIV polypeptide may be administered with the HIV polypeptide coupled to a carrier molecule such as KLH or BSA. The composition could also include an adjuvant where the adjuvant is a lipid, a toxin, a cytokine, oligonucleotides or bacterial DNA.

A method of preventing an HIV-infected subject from developing AIDS also includes administering to the HIV-infected subject AZT or treating the HIV-infected subject with highly active retroviral therapy (HAART).

The present invention also provides a method for preventing an HIV-infected subject from developing AIDS when the subject does not exhibit an HLA-Cw7-restricted CTL response. In such a situation, the method includes first determining whether the subject has or expresses the HLA-Cw7 haplotype. Such a determination is understood to include conducting a serological assay using an antibody that recognizes HLA-Cw7 or performing a nucleic acid amplification reaction whereby an HLA-Cw7 region is amplified. If these tests reveal that the subject does express the HLA-Cw7 haplotype, a method of the claimed invention further provides that an HLA-Cw7 restricted CTL response be elicited. Ways of eliciting such a T-cell response include administering to the subject a therapeutically effective amount an interferon, particular α- or γ-interferon, so that expression levels of HLA-Cw7 haplotype increase. This method also comprises the additional step of stimulating HIV-specific T helper cell responses.

The present invention also includes a method of preventing HIV infections in an uninfected subject by first determining whether the subject has or expresses an HLA-Cw7-hapiotype and, if the subject does, then administering to the subject a composition containing an HIV polypeptide that also is a CTL epitope, optionally also providing a T helper epitope. This preventative method contemplates prevention of infection by HIV-1. If the subject who is uninfected can express an HLA-Cw7 haplotype, the invention is understood to include compositions of an HIV polypeptide encompassing HIV envelope polypeptide or gag polypeptide, or fragments thereof. A synthetic peptide whose sequence is derived from an HIV polypeptide also can be used. This HIV-derived synthetic peptide can be from 11 to 25 residues in length and include the sequence YL(R/K)DQQLLGIWGC (SEQ ID NO:33 or SEQ ID NO:34), FLGFLGAAGSTMGAASLTLTVQARQ (SEQ ID NO:20), or VYYGVPVWKEA (SEQ ID NO:1). As previously mentioned, the methods of the present invention also include peptides comprising one or more of the following sequences: LWDQSLKPCVKLT (SEQ ID NO:4), SVITQACSKVSFE (SEQ ID NO:8), or GTGPCTNVSTVQC (SEQ ID NO:16). Any combination of one, two, three, four, five, or six of these peptide sequences may be used with the methods of the present invention.

Furthermore, the HIV polypeptide can be coupled to a carrier such as KLH or BSA; and, it could also be administered with an adjuvant, where the adjuvant is a lipid, a toxin, cytokine synthetic oligonucleotide or bacterial DNA. In addition to administering to the uninfected subject an HIV polypeptide, the subject also can be treated with AZT or HAART.

As previously mentioned, the HIV peptides used in the methods of the present invention may be provided to a cell as an expression construct that comprises a polynucleotide encoding one or more HIV peptides. In some aspects of the present invention, different mini-gene constructs may be administered such that more than one type of peptide sequence is provided to a cell. In other aspects of the present invention, an expression construct may contain sequences that enable it to express more than one peptide sequence; for example, the expression construct may contain sequences that allow it to express both FLGFLGAAGSTM-GAASLTLTVQARQ (SEQ ID NO:20) and VYYGVPVWKEA (SEQ ID NO:1). The expression construct may thus be able to express one, two, three, four, five, six or more peptide sequences.

In addition, the present invention includes preventing HIV infection in an uninfected subject when the subject expresses or can express the HLA-Cw7 haplotype and by eliciting an HLA-Cw7-restricted CTL response. Alternatively, the subject could be given a therapeutically effective amount an interferon so that the expression levels of HLA-Cw7 haplotype increase.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
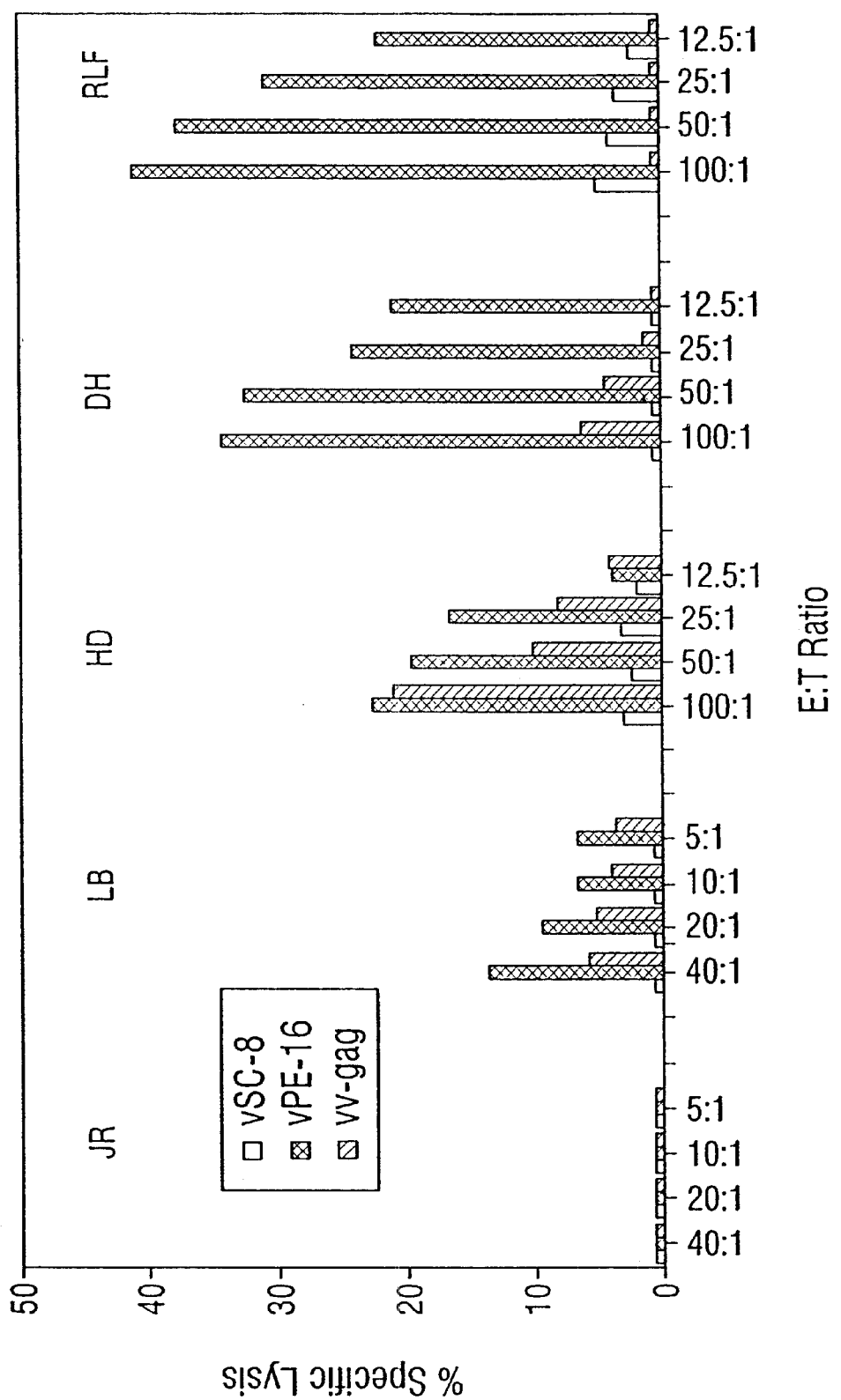
FIG. 1. HIV-1 envelope- and gag-Specific CTL Activity in HIV+ LTNPs. The PBMCs from one control (JR) and four HIV+ LTNPs (LB, HD, DH, and RLF) were assayed for CTL activity against autologous B-cell lines as target cells after infection with either control (vSC-8) or recombinant vaccinia virus expressing the envelope protein (vPE-16) or the gag protein (vv-gag).

Treatment and preventative therapies against AIDS in both infected and uninfected persons is critical because in 1995, more than 1.25 million cases of AIDS were reported to the World Health Organization. Obviously, therapies that treat and prevent the onset of AIDS are of critical importance. However, many treatment therapies including antiretroviral chemotherapy have been tested and implemented but they have yet to eliminate the disease. Also, vaccine strategies have not yet provided successful results. Because anti-HIV antibodies have been shown in vitro to enhance virus infection of both monocytes and lymphocytes, a vaccine that avoids evoking an antibody response, but that provokes a T-cell response, may be promising.

Interestingly, some patients infected with HIV maintain a disease-free state for ten years or more and do not develop AIDS; however, the reasons for this remain unknown. Recent evidence suggests a role for T-cells, particularly cytotoxic T lymphocytes (CTLs), in the establishment and maintenance of the disease-free status of long-term non-progressors (LTNPs) (Clerici, 1991; Haynes, 1996; Koup, 1994; Lifson, 1991;, Munoz, 1995; Pantaleo, 1994; Picard, 1992; Rinaldo, 1995; Roos, 1995; Rosenberg, 1997; Rowland-Jones, 1993, 1995). Because CTLs are activated in the context of MHC surface molecules, a genetic element corresponding to CTL restriction could contribute to long term non-progression. Identification of such a genetic element could be used to diagnose HIV-infected patients to determine whether they possess a genetic composition that is compatible with LTNPs. Furthermore, the genetic element can be used as a marker for determining which patients, both infected and uninfected, could benefit from a treatment for prevention against the development of AIDS using T-cell responses and HIV polypeptides and peptides. In this situation, a subject could be tested for presence of the genetic element, and if the subject possessed the element, the subject could be treated to prevent the onset of AIDS.

The present invention, in fact, provides such a genetic element that can be used to identify possible LTNPs and that can be used to implement treatment therapies against the development of AIDS. HLA-Cw7, an HLA genetic element in LTNPs, has been linked with long term non-progression. HIV-1-seropositive LTNPs exhibit an envelope-specific CTL response that is HLA-Cw7-restricted. Therefore, HLA-Cw7 restriction can be used as a diagnostic tool to determine whether an HIV-infected patient may be an LTNP.

The invention also demonstrates that HIV-envelope-specific CTLs recognize epitopes from highly conserved regions in the HIV envelope protein, particularly three peptides derived from gp160. Thus, the invention provides a method of treatment that provokes an HLA-Cw7-restricted CTL response against HIV polypeptides. In some methods of the invention, the three peptides can be used individually or in combination to provoke the response. Additionally, an HIV polypeptide, peptide or the corresponding polynucleotide can be coupled to a carrier molecule, such as KLH or BSA, or it can be used in conjunction with an adjuvant, such as a lipid, toxin, cytokine, oligonucleotide or bacterial DNA. Methods to augment this response include the use of alpha- or gamma-interferon to increase the level of HLA-Cw7 haplotype expression in those individuals who are candidate LTNPs.

The diagnostic and treatment methods disclosed herein take advantage of the identification of a novel HIV-specific HLA haplotype.

A. HIV and Immunity
1. Human Immunodeficiency Virus

HIV is classified as a retrovirus because it contains reverse transcriptase. Infection of cells with HIV usually results in cell death. HIV presents two major serotypes, HIV-1 and HIV-2, that are readily distinguishable by differences in antibody reactivity to the envelope glycoprotein. HIV-1 and HIV-2 share about 40% homology. HIV-1 has been shown by some that to more efficient at causing AIDS than HIV-2.

Most HIV-infected patients ultimately develop full-blown AIDS. Generally, a patient is formally diagnosed with AIDS when the patient's CD4+ T cell count falls below 200 cells/mm3, or when the patient exhibits a first AIDS-defining opportunistic infection or neoplasm. Only a small number of HIV-infected individuals, approximately 10%, do not exhibit the diseased state after ten or more years of infection. Long-term non-progressors (LTNPs) are patients who have been infected with HIV-1 but who have not exhibited progression of AIDS after ten or more years following infection. The cause of non-progression is not known.

The first step of HIV infection is the high affinity binding of gp120 glycoprotein to the CD4 receptor, present on the surface of many cell types including T4 cells, monocyte-macrophages, dendritic cells and cells of the central nervous system. The high affinity of the HIV envelope glycoprotein to the CD4 receptor is a crucial step in the pathogenesis of HIV since the major cells that express CD4 are the target cells (Maddon, 1986; Dalgleish, 1984; Klatzmann, 1984).

2. Major Histocompatibility Complex

The present invention identifies an HIV-specific MHC class I molecule that is present in HIV-infected LTNPs. The invention discloses different diagnostic, preventative, and treatment methods that take advantage of this genetic marker to identify and treat those individuals who can exhibit an HLA-Cw7-restricted CTL response.

The human major histocompatibility complex (MHC) contains within a two megabase telomeric segment six HLA class I genes (Trowsdale, 1993). Among these, HLA-A, -B, and -C encode highly polymorphic, ubiquitously expressed, membrane bound glycoproteins, noncovalently associated with $\beta_2$-microglobulin (Bjorkman and Parham, 1990; Klein, 1986). They present short peptide ligands derived from endogenously-synthesized proteins to the $\alpha\beta$ T-cell receptor (TCR) of CD8+ T lymphocytes, enabling these cytotoxic T cells to eliminate the virally-infected host cell (Townsend and Bodmer, 1989).

Cells can be classified according to which HLA molecules are expressed on their surface; one of skill in the art is well aware of methods of "HLA typing" such as, for example, the method of Olerum and Zetterquist (Olerum, 1992).

Evidence of a role for HLA-C antigens in the presentation of foreign antigens to CTLs is sparse (Bogedain, 1995; van den Eynde, 1995; Johnson, 1993; Littaua, 1991), in contrast to the vast literature on HLA-A and -B. The importance of HIV-specific cell-mediated immunity (CMI), including both proliferative and CTL responses, for the successful control of virus replication has been realized in studies (reviewed by Haynes), using cohorts of LTNPs and high-risk individuals (Haynes, 1996). In this regard, Rosenberg et al. (Rosenberg, 1997) recently reported that HIV-infected individuals who control viremia do so because of high levels of HIV-specific CMI, measured in terms of CD4+ T cell proliferative responses directed against the envelope and p24 proteins of HIV. More recently, Musey et al., (Musey, 1997) reported that in early stages of HIV infection, induction of HIV-envelope-specific CTL memory response helps in controlling virus replication and delaying progression to HIV-induced AIDS.

With regard to HIV-1 infection, HIV-1-specific CTLs have been directly detected using peripheral blood mononuclear cells (PBMC) from HIV-1-infected subjects (Haynes, 1996; Falk, 1993; Johnson, 1993; Jassoy 1992; Dadaglio, 1991; Gasson, 1987; Dai, 1992). Therefore, investigators have focused their attention on identifying HLA haplotypes that are involved in HIV-induced CTL responses. Studies by Littaua et al. and Johnson et al. report that CTL clones established from seropositive asymptomatic individuals recognized highly conserved epitopes from the gag and envelope proteins restricted by HLA-Cw4 and -Cw3. Other researchers have identified CD8+ CTL epitopes on gp41 that were restricted by HLA-A3.1 (Takahashi, 1991) and HLA-A24 (Dai, 1992). The HLA-24-restricted CTL epitope was localized to amino acids 584 to 591 of gp141. A mutation at amino acid 585 eliminates the CTL induction response (Dai, 1992).

B. Diagnostic Test for Long-term Non-progression of AIDS

A diagnostic test according to the present invention can evaluate whether an HIV-infected person is a candidate for long-term non-progression by assaying for an HLA-Cw7-restricted CTL response against a target cell. Another diagnostic test encompassed by the present invention can evaluate whether a subject is a candidate for a treatment method that prevents the development of AIDS.

In one embodiment, the present invention includes a diagnostic test that determines whether a subject can exhibit an HLA-Cw7-restricted CTL response. Such a test generally comprises obtaining a T-cell population from a subject and determining whether those cells are capable of responding to a target cell expressing the HLA-Cw7 determinant. In another embodiment, a diagnostic test is employed to determine whether a subject expresses the HLA-Cw7 haplotype. If the subject does, the present invention includes eliciting an HLA-Cw7-restricted CTL response. In further embodiments that are discussed below, a subject who either exhibits or can exhibit an HLA-Cw7-restricted CTL response is administered a treatment method to prevent the development of AIDS.

1. Target Cells

In one embodiment of the present invention, a target cell is used to assay whether an HIV-infected patient can exhibit a restricted T-cell response. A target cell is any cell that expresses class I MHC molecules. Most somatic cells have MHC class I expression, but the levels vary by cell type. Generally, lymphocytes express the highest levels of class I molecules, with approximately $5 \times 10^5$ molecules expressed per cell. A single cell can express a multitude of class I MHC molecules that present a peptide in their peptide-binding cleft. A normal, healthy cell will display self peptides derived from common intracellular protein fragments. MHC class I molecules of a virus-infected cell, however, will display viral peptides in addition to self peptides. Specific class I molecules will display specific viral peptides, while other types of class I molecules will display other viral peptides. Furthermore, allelic differences in the peptide-binding clefts of various individuals leads to different sets of viral peptides being displayed. In the present invention, the T-cell response being assayed is restricted to the MHC class I molecule HLA-Cw7. The invention demonstrates that HLA-Cw7 is a haplotype that displays HIV envelope-derived peptides based on T-cell response assays.

Target cells that are useful in assaying a T-cell response include cells from an autologous B-cell line (B-LCL), dendritic cells, or MHC matched cells. The term "autologous" is used to refer to cells derived from a subject from whom the effector cells are also derived. An autologous B-LCL can be prepared using peripheral blood mononuclear cells (PBMCs) from the subject who will be diagnosed or treated and transforming them. In a preferred embodiment, an autologous B-LCL is made from the HIV-infected subject and used as a target cell in a T-cell response assay to predict long-term non-progression in the B-LCL donor.

Dendritic (DC) cells act as antigen presenting cells and play a key role in T-cell activation. They are unique among antigen presenting cells (APC) by virtue of their potent capacity to activate immunologically naive T cells (Steinman, 1991). DC express constitutively, or after maturation, several molecules that mediate physical interaction with and deliver activation signals to responding T cells. These include class I and class II MHC molecules, CD80 (B7-1) and CD86 (B7-2), CD40, CD11a/CD18 (LFA-1), and CD54 (ICAM-1) (Steinman, 1995; Steinman, 1991). DC can present antigen to both CD8+ and CD4+ T lymphocytes. DC also secrete, upon stimulation, several T cell-stimulatory cytokines, including IL-1β, IL-6, IL-8, macrophage-inflammatory protein-1α (MIP-1α) and MIP-1γ (Mohamadzadeh, 1996; Ariizumi, 1995; Kitajima, 1995; Caux, 1994; Enk, 1992; Heufler, 1992; Matsue, 1992; Schreiber, 1992). Both of these properties, adhesion molecule expression and cytokine production, are shared by other APC (e.g., activated macrophages and B cells), which are substantially less competent in activating naive T cells.

Furthermore, peptide-pulsed DC have been used successfully without the use of any adjuvants to induce protective CMI responses in both animal models and limited human clinical trials.

Target cells of the present invention include any MHC-matched cell, which is a cell that bears the proper MHC or HLA haplotype on its surface so as to be recognized by the effector cell being employed in producing a CTL response.

In some embodiments, the target cells can be tested for an HIV-specific T-cell response by introducing a viral vector expressing an HIV polypeptide or by introducing HIV peptides into the cell. In other embodiments of the present invention, viral polypeptide and peptides are derived from the HIV envelope gene product, particularly gp160.

2. Effector Cells

An embodiment of the present diagnostic method assays for an HLA-Cw7-restricted CTL response by utilizing effector cells that demonstrate cytotoxic responses. Generally, effector cells are T cells derived from antigen-activated memory cells that have cytotoxic or delayed type hypersensitivity activity. With their lytic capabilities, effector cells are important for recognition and removal of altered self-cells, which includes virus-infected cells. They are produced by the activation of T cytotoxic (Tc) cells.

T-cell activation is an important step in the protective immunity against pathogenic microorganisms (e.g., viruses, bacteria, and parasites) and foreign proteins, and particularly those that reside inside affected cells. T cells express receptors on their surface (i.e., T-cell receptors), which recognize antigens presented on the surface of antigen-presenting cells. During a normal immune response, binding of these antigens to the T cell receptor initiates intracellular changes leading to T-cell activation. DC express several different adhesion (and costimulatory) molecules, which mediate their interaction with T cells. The combinations of receptors (on DC) and counter-receptors (on T cells) that are known to play this role include: a) class I MHC and CD8, b) class II MHC and CD4, c) CD54 (ICAM-1) and CD11a/CD18 (LFA-1), d) ICAM-3 and CD11a/CD18, e) LFA-3 and CD2, f) CD80 (B7-1) and CD28 (and CTLA4), g) CD86 (B7-2) and CD28 (and CTLA4), and h) CD40 and CD40L (Steinman, 1995). Importantly, not only does ligation of these molecules promote physical binding between DC and T cells, it also transduces activation signals.

In addition to specific activation, T cells also can be nonspecifically induced to divide through contact with mitogens. Lectins are plant-derived, mitogenic proteins that bind to sugars. Lectins that activate B and T cells include such as phytohemagglutinin, Concanavalin A, or Pokeweed mitogen.

More particularly, the claimed invention relates to predicting long-term non-progression by looking at HLA-Cw7-restricted CTL responses. CTLs are cytotoxic T cells. CTLs constitute a subset of effector T cells that is defined by the ability to mediate membrane damage, which results in cell lysis. Cytokines released by T helper cells ($T_H$) induce a T cytotoxic cell ($T_C$) to proliferate and differentiate when the $T_C$ cell recognizes an antigen-MHC class I molecule complex. CTLs generally express CD8.

3. T-cell or T Lymphocyte Response

Some methods of the claimed invention take advantage of T-cell responses by using them as a diagnostic indicator of long-term non-progression or as a preventative therapy against the development of AIDS. More particularly, the methods assay for the existence of HLA-Cw7-restricted CTL responses.

Most viral infections in immune competent mammals result in a cell-mediated immune response against the virus infected cells, the net effect being lysis of the cells. During viral infections, viral proteins are synthesized in the cell for inclusion into new viral particles. Some of those endogenous viral proteins also are degraded and transported into the class I antigen presentation pathway, where the foreign antigens associate with a class I MHC molecule. This peptide-MHC complex then is transported to the surface of the cells where the foreign peptide is presented, in the context of self MHC, to cytotoxic T cells (CTLs).

CTLs are antigen-specific effector cells. Most are CD8+ T cells that recognize antigen that is presented by MHC class I molecules; but a few are CD4+ T cells that tend to recognize antigens presented by MHC class II molecules. Lymphocyte surface marker studies can be used to assay for the presence of such T-cell surface markers using various procedures that are known to one of ordinary skill in the art, including the use of immunofluorescence and flow cytometry.

Upon recognition of the antigen as foreign, the CTLs lyse the target cell either through molecular interactions that induce apoptosis, or through secretion of pore forming enzymes that create holes in the plasma membrane disrupting its integrity. Thus, the CTL-mediated immune response plays a significant role in the clearance of virally-infected cells.

The ability of CTL effector cells to lyse virus-infected target cells is regulated by genetic and antigenic restrictions. Target cells must carry a viral antigen that is the same or equivalent to that which originally induced the CTLs. The target cell and the induced CTL must also bear the same MHC class I molecule.

In particular, the development of MHC-restricted virus specific CD8+ CTL and CD4+ helper ($T_H$) T cell responses correlate with the resolution of acute viral infections (Ada and Jones, 1986; Howes, 1979). In individuals infected with HIV, CD8+ T lymphocytes contribute to the control of HIV replication by direct lysis of infected cells and by suppressing viral replication (Walker, 1987; Walker, 1986). Although CD8+ MHC restricted HIV-specific $T_C$ responses are elicited in healthy HIV seropositive individuals as demonstrated by analysis of peripheral blood lymphocytes, these responses are decreased or absent in AIDS patients (Paltaleo, 1990). The present invention provides the identification of an MHC class I molecule that restricts a T-cell response against HIV polypeptides. HLA-Cw7 is a haplotype that restricts a T lymphocyte response against the envelope polypeptide. Long-term non-progressor HIV-infected patients exhibited this restricted response, and consequently, the demonstration of such a response can be a predictor of long-term non-progression.

The identity of a restricting haplotype can be revealed through the use of a variety of techniques, including antibody inhibition studies, which involve class I-specific antibodies and genetic means such as PCR analysis.

Furthermore, the onset of AIDS can be prevented by eliciting an HIV-specific HLA-Cw7-restricted CTL response in both infected and uninfected subjects using HIV polypeptides or peptides.

4. Response Assays

As stated above, one aspect of the present invention involves assaying for a restricted T-cell response. In one embodiment, demonstration of an HLA-Cw7-restricted CTL response can be used to predict long-term non-progression and to identify individuals for whom treatment may be beneficial. T-cell responses can be measured by a variety of protocols that are known to one of ordinary skill in the art. Some of these assays are described in fuller detail below.

a. Lysis Using $^{51}[Cr]$

Cell-mediated lympholysis (CML) can be used as an indication of T-cell response. Target cells can be labeled with radioactive chromium-51 ($^{51}[Cr]$) prior to exposure to effector cells. The amount of $^{51}[Cr]$ released into the media is proportional to the level of cell-mediated lysis. In the preferred embodiment of the present invention, autologous B-lymphocyte cell lines are cultured and then exposed to $^{51}[Cr]$ sodium chromate for two hours before they are incubated with cells possessing cytotoxic activity.

b. γ-Interferon Production

Interferon gamma (γ-interferon), also called type II or immune interferon, is produced by T cells and NK cells. It is critical for the development of helper T cells. Because it is the primary macrophage-activating factor, it is a strong cytokine in cell-mediated immunity. γ-interferon increases the levels of MHC class I and MHC class II expression, which improves antigen presentation and other cognitive reactions. Furthermore, it amplifies the effects of TNF-α and raises expression levels of adhesion molecules on the surface of vascular endothelial cells, which leads to T cell adhesion and extravasation. Finally, as part of the claimed invention, γ-interferon is secreted by CTLs, enabling the level of γ-interferon to act as an indicator of CTL activity and thus of a CTL response. Determining γ-interferon levels is performed using standard assay methods.

c. Tetramer Assay

Tetramer assays are well known to those of skill in the art. See Altman, 1996.

d. Cytokine Production

Cytokines are proteins that play important roles in the regulation of immune responses as well as in the differentiation pathways of different cell types. They have a critical function in T cell regulation and development, and these include γ-interferon, interleukin I (IL-1), IL-2, IL-4, IL-5, IL-6, IL-7, IL-10, IL-12, IL-13, IL-14, IL-15, lymphotoxin, MIF, TGF-β, TNF-α, and other chemotactic cytokines. Assays for cytokines are well known in the art.

5. Expression of HLA-Cw7

In addition to providing methods directed at determining whether a subject exhibits an HLA-Cw7-restricted CTL response, the present invention includes methods of determining whether a subject expresses or can express the HLA-Cw7 haplotype. Because the HLA-Cw7 haplotype provides a marker to identify individuals who may respond to a treatment to prevent the onset of AIDS, a method of the present invention includes testing for either HLA-Cw7 expression or the ability to express HLA-Cw7 in HIV-infected and uninfected subjects who do not exhibit an HLA-Cw7-restricted CTL response. There are numerous assays available to qualify and quantify expression levels of a molecule, and these can involve detecting DNA sequences that signify a particular haplotype or measuring protein or mRNA expression levels. These assays are well known by one of ordinary skill in the art. Some examples are provided below.

a. Serological Assay

The present invention includes the implementation of serological assays to evaluate the expression levels of HLA-Cw7. These assays take advantage of antigen-antibody interactions to quantify and qualify antigen levels. There are many types of assays that can be implemented, which one of ordinary skill in the art would know how to implement in the scope of the present invention.

i. ELISAs, Immunoassay and Immunohistological Assay.

Immunoassays encompassed by the present invention include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain preferred immunoassays are the various types of enzyme linked immunosorbent assays (ELISAs) and radioimmunoassays (RIA) known in the art. Immunohistochemical detection using tissue sections is also particularly useful.

In one exemplary ELISA, the antibodies are immobilized on a selected surface, such as a well in a polystyrene microtiter plate, dipstick, or column support. Then, a test composition suspected of containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is known as a "sandwich ELISA". Detection also may be achieved by the addition of a second antibody specific for the desired antigen, followed by the addition of a third antibody that has binding affinity for the second antibody, with the third antibody being linked to a detectable label.

Variations on ELISA techniques are known to those of skill in the art. In one such variation, the samples suspected of containing the desired antigen are immobilized onto the well surface and then contacted with the antibodies of the invention. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

In ELISAs, it is more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 250 to 27° C., or may be overnight at about 4° C. or so.

After all incubation steps in an ELISA are followed, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase, or hydrogen peroxidase-conjugated antibody for a period of time and under conditions that favor the development of further immune complex formation, e.g., incubation for 2 hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Alternatively, the label may be a chemiluminescent one. The use of such labels is described in U.S. Pat. Nos. 5,310,687, 5,238,808 and 5,221,605.

Assays for the presence of an HLA haplotype may be performed directly on tissue samples. Methods for in vitro situ analysis are well known and involve assessing binding of antigen-specific antibodies to tissues, cells, or cell extracts. These are conventional techniques well within the grasp of those skilled in the art.

b. Nucleic Acid Amplification Reaction

Nucleic acid molecules can be detected using a variety of techniques, including amplification reactions. The present invention contemplates using these amplification reactions to detect whether the HLA-Cw7 gene is or can be expressed in a subject patient. In one method, an amplification reaction is used to detect DNA rearrangements that indicate a subject can or does express the HLA-Cw7 haplotype.

i. Polymerase Chain Reaction (PCR™)

Nucleic acid used as a template for amplification is isolated from cells contained in the biological sample, according to standard methodologies (Sambrook, 1989). The nucleic acid may be genomic DNA or fractionated or whole cell RNA. Where RNA is used, it may be desired to convert the RNA to a cDNA.

Pairs of primers that selectively hybridize to nucleic acids corresponding to a KATP channel protein or a mutant thereof are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ (RT-PCR™) amplification procedure may be performed in order to quantify the amount of mRNA amplified or to prepare cDNA from the desired mRNA. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

ii. Other Nucleic Acid Amplification Reactions

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids that involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al (EPA No. 329 822, incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one, end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al. (PCT Application WO 89/06700, incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990, incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

iii. Analysis of Amplification Products

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook, 1989.

Alternatively, chromatographic techniques may be employed to effect separation. There are many kinds of chromatography that may be used in the present invention: adsorption, partition, ion-exchange and molecular sieve, and many specialized techniques for using them including column, paper, thin-layer, and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe derived from the HLA-Cw7 gene sequence. The techniques involved in Southern blotting are well known to those of skill in the art and can be found in many standard books on molecular protocols. See Sambrook, 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

6. Eliciting a Restricted T-cell Response

The present invention discloses methods of preventing AIDS in patients who exhibit an HLA-Cw7-restricted CTL response or who can express the HLA-Cw7 haplotype. With subjects who can express the haplotype but do not exhibit an HLA-Cw7-restricted CTL response, a response can be elicited from them by increasing the level of HLA-Cw7 haplotype expression. This can be accomplished by administering a therapeutically effective amount of γ-interferon. A description of 7-interferon is discussed above.

7. HIV Polypeptides and Peptides

In some embodiments, methods of the present invention involve the presentation of HIV polypeptides or peptides either to assay for a virus-specific T-cell response or as a method of eliciting a virus-specific T cell response.

a. HIV Polypeptides and Fragments Thereof

It is clear from a number of reports in recent years that DNA-based vaccination strategy is effective in priming specific CTL responses, particularly against viral antigens (Ulmer, 1993; Xiang, 1994; Sedegah, 1994; Fuller, 1994; Lu, 1995; Yokoyama, 1995; Yasutomi, 1996). Additionally, successful attempts have been made for inducing CTL responses by introducing the peptide sequences as nucleic acids, either as direct DNA vaccines or recombinant vaccinia virus-based polyepitope vaccine (Thomson, 1996; An, 1997; Sastry, 1992; Nehete, 1994; Nehete, 1995; Ciernik, 1996; Wang, 1998). The rationale for DNA vaccines based on CTL epitopes instead of the whole protein antigens of HIV is the perceived need for avoiding unwanted immune responses such as infection enhancing antibodies (Levy, 1993).

Therefore, aspects of the present invention concern the use of isolated DNA segments and recombinant vectors encoding wild-type, polymorphic, or mutant HIV polypeptides, and fragments thereof (such as peptides), and the use of recombinant host cells through the application of DNA technology that express wild-type, polymorphic, truncated, or mutant HIV polypeptide. Preferred embodiments of the claimed methods include the use of the envelope and gag polypeptides of HIV. Even more preferred is the use of gp160 polypeptide. Finally, another preferred embodiment utilizes HIV peptides, particularly peptides derived from gp160.

The present invention concerns DNA segments, isolatable from mammalian and human cells, that are free from total genomic DNA and that are capable of expressing a protein or polypeptide that is derived from HIV, particularly HIV-1.

As used herein, the term "DNA segment" refers to a DNA molecule that has been isolated free of total genomic DNA of a particular species. Therefore, a DNA segment encoding an HIV polypeptide refers to a DNA segment that contains wild-type, polymorphic, truncated, or mutant HIV polypeptide coding sequences yet is isolated away from, or purified free from, total mammalian or human genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified wild-type, polymorphic, truncated, or mutant HIV polypeptide gene refers to a DNA segment including wild-type, polymorphic, or mutant HIV polypeptide coding sequences and, in certain aspects, regulatory sequences, isolated substantially away from other naturally occurring genes or protein encoding sequences. In this respect, the term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. Similarly, the term "mini-gene" is used throughout this application to refer specifically to smaller gene segments that express, or may be adapted to express, portions of proteins or polypeptides, such as peptides, domains, fusion proteins, and mutants.

"Isolated substantially away from other coding sequences" means that the gene of interest, in this case the wild-type, polymorphic, or mutant HIV polypeptide gene, forms a significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by human manipulation.

In particular embodiments, the invention concerns isolated DNA segments and recombinant vectors incorporating DNA sequences that encode a wild-type, polymorphic, truncated, or mutant HIV polypeptide or peptide that includes within its amino acid sequence a contiguous amino acid sequence in accordance with, or essentially corresponding to wild-type, polymorphic, truncated, or mutant HIV polypeptides.

In other embodiments, the invention concerns isolated DNA segments and recombinant vectors incorporating DNA sequences that encode a HIV polypeptide or peptide that includes within its amino acid sequence a contiguous amino acid sequence in accordance with, or essentially corresponding to the HIV env or gag polypeptide. For example, the invention concerns the use of a mini-gene as a vehicle for effecting an immune response against the amino acid product of the mini-gene. A mini-gene may encode a peptide that can elicit a T-cell specific response, particularly an HLA-Cw7 response.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of HIV env or gag polypeptides provided the biological activity of the protein is maintained.

The term "functionally equivalent codon" is used herein to refer to codons that encode the same amino acid, such as the six codons for arginine or serine, and also refers to codons that encode biologically equivalent amino acids (see TABLE 1, below).

TABLE 1

CODON TABLE

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |

TABLE 1-continued

CODON TABLE

| Amino Acids | | | Codons | | | | | |
|---|---|---|---|---|---|---|---|---|
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments used in the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

The DNA segments used in the present invention encompass biologically functional equivalent HIV env and HIV gag proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine DNA binding activity at the molecular level.

One also may prepare fusion proteins and peptides, e.g., where the HIV polypeptide coding regions are aligned within the same expression unit with other proteins or peptides having desired functions, such as for purification or immunodetection purposes (e.g., proteins that may be purified by affinity chromatography and enzyme label coding regions, respectively).

Encompassed by the invention are DNA segments encoding relatively small peptides, such as, for example, peptides of from about 15 to about 50 amino acids in length, and more preferably, of from about 15 to about 30 amino acids in length; and also larger polypeptides up to and including proteins corresponding to the full-length sequences of the HIV env or HIV gag polypeptides.

i. In Vitro Protein Production

Following transduction with a viral vector according to some embodiments of the present invention, primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production and/or presentation of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Another embodiment of the present invention uses autologous B lymphocyte cell lines, which are transfected with a viral vector that expresses HIV envelope protein. Other examples of mammalian host cell lines include Vero and HeLa cells, other B- and T- cell lines, such as CEM, 721.221, H9, Jurkat, Raji, etc., as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection: for dhfr, which confers resistance to; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

ii. Biological Functional Equivalents

As will be understood by those of skill in the art, modification and changes may be made in the structure of a HIV polypeptide or peptide and still produce molecule having like or otherwise desirable characteristics. For example, certain amino acids may be substituted for other amino acids in a protein structure without appreciable loss of interactive binding capacity with structures such as, for example, antigen-binding regions of antibodies or binding sites on molecules such as Tat and RNA polymerase II. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. It is thus contemplated by the inventors that various changes may be made in the sequence of HIV polypeptides or peptides (or underlying DNA) without appreciable loss of their biological utility or activity.

In terms of functional equivalents, the skilled artisan also understands it is also well understood by the skilled artisan that inherent in the definition of a biologically-functional equivalent protein or peptide, is the concept of a limit to the number of changes that may be made within a defined portion of a molecule that still result in a molecule with an acceptable level of equivalent biological activity. Biologically-functional equivalent peptides are thus defined herein as those peptides in which certain, not most or all, of the amino acids may be substituted. In particular, where small peptides are concerned, less amino acids may be changed. Of course, a plurality of distinct proteins/peptides with different substitutions may easily be made and used in accordance with the invention.

It is also well understood that where certain residues are shown to be particularly important to the biological or structural properties of a protein or peptide, e.g., residues in the active site of an enzyme, or in the RNA polymerase II binding region, such residues may not generally be exchanged. This is the case in the present invention, where residues shown to be necessary for a CTL induction response should not generally be changed.

Amino acid substitutions are generally based on the relative similarity of the amino acid side-chain substituents, for example, their hydrophobicity, hydrophilicity, charge, size, and the like. An analysis of the size, shape, and type of the amino acid side-chain substituents reveals that arginine, lysine, and histidine are all positively charged residues; that alanine, glycine, and serine are all a similar size; and that phenylalanine, tryptophan, and tyrosine all have a generally similar shape. Therefore, based upon these considerations, the following subsets are defined herein as biologically functional equivalents: arginine, lysine, and histidine; alanine, glycine, and serine; and phenylalanine, tryptophan, and tyrosine.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA, taking into consideration also that the genetic code is degenerate and that two or more codons may encode the same amino acid. A table of amino acids and their codons is presented hereinabove for use in such embodiments, as well as for other uses, such as in the design of probes and primers and the like.

b. Synthetic Peptides

The present invention also describes HIV env peptides for use in various embodiments of the present invention. The sequences of these peptides are found throughout the provided examples, for instance in TABLES 2 and 8. It is contemplated that the methods of the present invention may employ a peptide that comprises one of these sequences or different peptides encoding a variety of these sequences. For example, a peptide comprising the sequence of peptide #61 may be used in combination with peptide #63 and/or with peptide #104 (see TABLE 2). Thus it is contemplated that any variety of permutations with the disclosed peptide sequences is included within the present invention. Peptides #61, #63, #104, #111, #113, and #116 have been used together, however, peptides including one or more of these sequences may be omitted from a cocktail according to the methods of the present invention. Alternatively, other sequences may be included in combination of peptide sequences. Accordingly, peptides with other sequences may be included in a cocktail, which may include, for example, #61 and/or #63 and/or #104 and/or #111 and/or #113 and/or #116.

Furthermore, the various consensus sequences for HIV envelope peptides are also within the scope of the invention (see Table 2). Table 2 shows a comparison of amino acid sequences of HIV envelope peptides (used in the examples, as indicated in Table 8) with corresponding consensus sequences from HIV-1 strains representing different clades. The consensus sequences were obtained from the 1995 Los Alamos National Laboratory data-base for amino acid sequences for clades A–U.

TABLE 2

| Peptide Sequeaces | | |
|---|---|---|
| Peptide 104 | V Y Y G V P V W K E A | SEQ ID NO:1 |
| Consensus-A | V Y Y G V P V W K D A | SEQ ID NO:2 |
| Consensus-B | V Y Y G V P V W K E A | SEQ ID NO:1 |
| Consensus-C | V Y Y G V P V W K E A | SEQ ID NO:1 |
| Consensus-D | V Y Y G V P V W K E A | SEQ ID NO:1 |
| Consensus-E | V Y Y G V P V W R D A | SEQ ID NO:2 |
| Consensus-F | V Y Y G Y P V W K E A | SEQ ID NO:1 |
| Consensus-G | V Y Y G Y P V W E D A | SEQ ID NO:2 |
| Consensus-O | V Y S G V P V W E D A | SEQ ID NO:3 |
| Consensus-U | V Y Y G V P V W K D A | SEQ ID NO:2 |
| Peptide 111 | L W D Q S L K P C V K L T | SEQ ID NO:4 |
| Consensus-A | L W D Q S L K P C V K L T | SEQ ID NO:4 |
| Consensus-B | L W D Q S L K P C V K L T | SEQ ID NO:4 |
| Consensus-C | L W D Q S L K P C V K L T | SEQ ID NO:4 |
| Consensus-D | L W D Q S L K P C V K L T | SEQ ID NO:4 |
| Consensus-E | L W D Q S L K P C V K L T | SEQ ID NO:4 |
| Consensus-F | L W D Q S L K P C V K L T | SEQ ID NO:4 |
| Consensus-G | L W D E S L K P C V K L T | SEQ ID NO:5 |
| Consensus-O | L W D Q S L K P C V Q M T | SEQ ID NO:6 |
| Consensus-U | L W D ? S L K P C V K L T | SEQ ID NO:7 |
| Peptide 113 | S V I T Q A C S K V S F E | SEQ ID NO:8 |
| Consensus-A | S A I T Q A C S K V S F E | SEQ ID NO:9 |
| Consensus-B | S V I T Q A C S K V S F E | SEQ ID NO:8 |
| Concensus-C | S A I T Q A C S K V S F D | SEQ ID NO:10 |
| Consensus-D | S A I T Q A C S K V T F E | SEQ ID NO:38 |
| Concensus-E | S V I K Q A C S K I S F D | SEQ ID NO:11 |
| Consensus-F | S T I T Q A C S K V S W D | SEQ ID NO:12 |
| Consensus-G | S T I K Q A C S K V N F D | SEQ ID NO:13 |
| Consensus-O | T T I ? Q A C S K V S F E | SEQ ID NO:14 |
| Consensus-U | S ? I K Q A C S K V S F E | SEQ ID NO:15 |
| Peptide 116 | G T G P C T N V S T V Q C | SEQ ID NO:16 |
| Consensus-A | G T G P C K N V S T V Q C | SEQ ID NO:17 |
| Consensus-B | G T G P C T N V S T V Q C | SEQ ID NO:16 |
| Consensus-C | G T G P C H N V S T V Q C | SEQ ID NO:18 |
| Consensus-D | G T G P C K N V S T V Q C | SEQ ID NO:17 |

TABLE 2-continued

Peptide Sequeaces

| | | |
|---|---|---|
| Consensus-E | G T G P C K N V S S V Q C | SEQ ID NO:39 |
| Consensus-F | G T G P C K N V S T V Q C | SEQ ID NO:17 |
| Consensus-G | G T G P C K N V S T V Q C | SEQ ID NO:17 |
| Consensus-O | G T G L C ? N I T V V T C | SEQ ID NO:19 |
| Consensus-U | G T G P C K N V S T V Q C | SEQ ID NO:17 |
| Peptide 63 | F L G F L G A A G S T M O A A S L T L T V Q A R Q | SEQ ID NO.20 |
| Consensus-A | F L G F L G A A G S T M G A A S I T L T V Q A R Q | SEQ ID NO:21 |
| Consensus-B | F L G F L G A A G S T M G A A S ? T L T V Q A R Q | SEQ ID NO:22 |
| Consensus-C | F L G F L G A A G S T M G A A S L T L T V Q A R Q | SEQ ID NO:20 |
| Consensus-D | F L G F L G A A G S T M G A A S ? T L T V Q A R Q | SEQ ID NO:22 |
| Consensus-E | I F G F L G A A G S T M G A A S L T L T V Q A R Q | SEQ ID NO:23 |
| Consensus-F | F L G F L G A A G S T M G A A S L T L T V Q A R Q | SEQ ID NO:20 |
| Consensus-G | F L G F L G A A G S T M G A A A T A L T V Q A R Q | SEQ ID NO:24 |
| Consensus-O | F L G V L S A A G S T M G A A S L T L T V Q A R Q | SEQ ID NO:40 |
| Consensus-U | F L G F L G A A G S T M G A A S ? ? L T V Q A R Q | SEQ ID NO:25 |
| Peptide 61 | Y L R D Q Q L L G T W G | SEQ ID NO:26 |
| Consensus-A | Y L R D Q Q L L G I W G | SEQ ID NO:26 |
| Consensus-B | Y L K D Q Q L L G I W G | SEQ ID NO:27 |
| Consensus-C | Y L K D Q Q L L G I W G | SEQ ID NO:27 |
| Cousensus-D | Y L K D Q Q L L G I W G | SEQ ID NO:27 |
| Consensus-E | Y L K D Q K F L G L W G | SEQ ID NO:28 |
| Consensus-F | Y L ? D Q Q L L G L W G | SE9 ID NO:29 |
| Consensus-G | Y L ? D Q Q L L G I W G | SEQ ID NO:30 |
| Consensus-O | Y L R D Q Q L L G L W G | SEQ ID NO:31 |
| Consensus-U | Y L E S Q Q L L G L W G | SEQ ID NO:32 |

Specific peptides were assayed for their abilities to elicit a specific T-cell response using AIDS-infected human PBMCs. Previous experiments had also examined HIV peptides, but in those studies, a series of peptides from the HIV envelope protein gp160 were tested for their ability to induce a murine T cell proliferative response, but not an antibody response (Sastry, 1991; incorporated by reference). Seven of 19 peptides (61, 63, 103, 104, 111, 113, and 116) induced relatively good T-cell proliferation responses in two F1 hybrid mouse strains (B6C3 F1 and A.SW×Balb/c F1). Peptides 61, 63, 103, 104, and 113 did not produce antibodies that could recognize recombinant gp160, but they induced a T-cell response against both the immunizing peptide and the HIV Env protein. Peptides 103–112 were from the first conserved region and peptides 113–117 were from the second conserved region. Peptides 61 and 63 were respectively from the immunodominant region and the membrane fusion domain.

A cocktail using some of the peptides identified in mice that induced a T-cell proliferative response was tested in monkeys for the ability to induce an HIV-specific T cell response (Nehete, 1993; incorporated by reference). Peptides 104, 111, and 63 produced a good response with PMBCs from all three monkeys tested, whereas peptides 113 and 116 produced weak responses. PMBCs from two of the monkeys showed good proliferative responses against peptide 61, while no responses were elicited using peptide 105 and R15K.

Moreover, specific peptide sequences from HIV-1 gene products that produce an in vivo CTL response have been identified using both a modified peptide (Berzofsky, 1991) and an unmodified, free synthetic peptide (Sastry, 1992; incorporated by reference). A synthetic peptide, R15K, from the immunodominant V3-loop (aa 315–329) of the HIV envelope protein gp120, induced CD8+ HIV-env-specific CTLs in mice.

Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

The compositions of the invention may include a peptide modified to render it biologically protected. Biologically protected peptides have certain advantages over unprotected peptides when administered to human subjects and, as disclosed in U.S. Pat. No. 5,028,592, incorporated herein by reference, protected peptides often exhibit increased pharmacological activity.

Compositions for use in the present invention may also comprise peptides which include all L-amino acids, all D-amino acids, or a mixture thereof. The use of D-amino acids may confer additional resistance to proteases naturally found within the human body and are less immunogenic and can therefore be expected to have longer biological half lives.

8. Delivery Systems

To test for a virus-specific T cell response, in some embodiments of the claimed invention, HIV polypeptides or peptides are delivered to target cells to express fragments of the viral protein on their surfaces for the purpose of eliciting a T-cell response. There are various methods of delivery including perfusion, transfection of an expression construct, viral vectors, and other means disclosed below.

a. Transfer by Perfusion

An embodiment of the claimed invention transfers peptides or a combination of peptides into cells via perfusion. Continuous perfusion of an expression construct or a viral construct also is contemplated. The amount of construct or peptide delivered in continuous perfusion can be determined by the amount of uptake that is desirable. The present invention discloses an example of perfusion whereby a cell culture with an initial concentration of $10^6$ cells/ml can first be labeled, washed, and then incubated with 100 µg of synthetic peptide for two hours.

b. Expression Vectors

In alternative embodiments, HIV polypeptides and peptides are delivered to target cells through, the use of expression constructs. Throughout this application, the term "expression construct" is meant to include any type of genetic construct containing a nucleic acid coding for an HIV polypeptide. A "viral vector" refers to an expression construct that is derived primarily from viral sequences. In order for the construct to effect expression, the polynucleotide encoding the HIV polynucleotide will be under the transcriptional control of a promoter. A "promoter" refers to a DNA sequence recognized by the synthetic machinery of the host cell, or by introduced synthetic machinery, that is required to initiate the specific transcription of a gene. The phrase "under transcriptional control" means that the promoter is in the correct location in relation to the polynucleotide to control RNA polymerase initiation and expression of the polynucleotide.

The term promoter will be used herein to refer to a group of transcriptional control modules that are clustered around the initiation site for RNA polymerase 11. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of an HIV polynucleotide is not believed to be critical, so long as it is capable of expressing the polynucleotide in the targeted cell. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, and the Rous sarcoma virus long terminal repeat can be used to obtain high-level expression of the HIV polynucleotide. The use of other viral or mammalian cellular or bacterial phage promoters, which are well-known in the art, to achieve expression of polynucleotides is contemplated as well, provided that the levels of expression are sufficient to induce a T-cell response.

By employing a promoter with well-known properties, the level and pattern of expression of a polynucleotide following transfection can be optimized. For example, selection of a promoter that is active in specific cells, such as tyrosinase (melanoma), alpha-fetoprotein and albumin (liver tumors), CC10 (lung tumor) and prostate-specific antigen (prostate tumor) will permit tissue-specific expression of HIV polynucleotides. Further, selection of a promoter that is regulated in response to specific physiologic signals can permit inducible expression of the HIV polypeptide construct.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are frequently overlapping and contiguous, often seeming to have a very similar modular organization.

Additionally any promoter/enhancer combination (as per the Eukaryotic Promoter Data Base EPDB) could also be used to drive expression of an HIV polynucleotide construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

In certain embodiments of the invention, the delivery of an expression vector in a cell may be identified in vitro or in vivo by including a marker in the expression vector. The marker would result in an identifiable change to the transfected cell permitting identification of expression. Usually, the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed along with the polynucleotide encoding an HIV polypeptide. Further examples of selectable markers are well known to one of skill in the art.

One will typically include a polyadenylation signal to effect proper polyadenylation of the transcript. The nature of the polyadenylation signal is not believed to be crucial to the successful practice of the invention, and any such sequence may be employed. The inventor has employed the SV40 polyadenylation signal in that it was convenient and known to function well in the target cells employed. Also contemplated as an element of the expression construct is a terminator. These elements can serve to enhance message levels and to minimize read through from the construct into other sequences.

c. Viral Vectors

In some embodiments of the present invention, an expression construct comprises a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes (discussed below), expression vectors need not be viral but, instead, may be any plasmid, cosmid, or phage construct that is capable of supporting expression of encoded genes in mammalian cells, such as pUC or Bluescript™ plasmid series.

i. Retroviruses

The retrovirus class is subdivided into three major groups: oncoviruses, such as murine leukemia virus; lentiviruses, which include HIV-1 and HIV-2; and foamy viruses (spumaviruses). Retroviruses are single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants.

The retroviral genome contains three genes—gag, pol, and env—that encode capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

The present invention encompasses the use of a lentivirus-derived vector to deliver an HIV polypeptide to a target cell. Lentiviruses include the immunodeficiency viruses HIV-1, HIV-2, SIV and FIV. It is well known that the human lentivirus HIV-1 is the causative agent of AIDS. Since AIDS was first recognized in the United States, the number of cases has been increasing at a dramatic pace and several million AIDS infections have now been reported. Once significant immunosuppressive symptoms appear in an infected individual, the expected outcome of the infection is death. There is currently no known treatment that can indefinitely delay or prevent the fatal consequences of the disease. Although the disease first manifested itself in homosexual or bisexual males and intravenous drug abusers, it has now spread to others by means such as intimate sexual contact with or receipt of blood products from a carrier of the virus.

In a similar manner, feline immunodeficiency virus, FIV, and simian immunodeficiency virus, SIV, are responsible for AIDS-like symptoms in cats and primates other than humans. FIV was first isolated from immunodeficient cats in California and has since been found in cats throughout the world. HIV-2 and SIV particularly infect primates such as macaques. As FIV, HIV-2 and SIV have biological and pathogenic features in common with HIV-1, they are valuable tools with which to investigate anti-AIDS strategies. HIV can itself be used as a vector (Dull, 1998; Naldini, 1996).

The primary event in the infection of target cells by lentiviruses is the interaction between the external envelope glycoprotein of the virus and its cellular receptor, as represented by gp120 and CD4 in the case of HIV-1 infection of human T cells. It has recently been reported that CD26 may also be required for HIV-1 entry into $CD4^+$ cells (Callebaut, 1993).

Although the envelope protein interaction with the target cell is essential for lentivirus entry, this knowledge has yet to lead to the development of an effective strategy to prevent viral infection. Certain peptides from gp120 V3 function to inhibit HIV infection (Nehete, 1993). However, De Rossi (1991) reported that V3-derived synthetic peptides actually enhanced HIV-1 infection of cells through a CD4-dependent mechanism.

In order to construct a retroviral vector, a nucleic acid encoding an HIV polypeptide is inserted into the viral genome in the place of certain viral sequences to produce a virus that is replication-defective. Alternatively, a mutated HIV virus that is incapable of leading to AIDS can be used. In order to produce virions, a packaging cell line containing the gag, pol and env genes but without the LTR and Ψ components is constructed (Mann, 1983). When a recombinant plasmid containing a human cDNA, together with the retroviral LTR and Ψ sequences, is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann, 1983). The media containing the recombinant retroviruses is then collected, optionally concentrated, and used for gene transfer. Retroviral vectors are able to infect a broad variety of cell types. However, integration and stable expression require the division of host cells (Paskind, 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux, 1989). Using antibodies against major histocompatibility complex class I and class II antigens, they demonstrated the infection of a variety of human cells that bore those surface antigens with an ecotropic virus in vitro (Roux, 1989).

ii. Adenoviruses

Human adenoviruses are double-stranded DNA tumor viruses with genome sizes of approximate 36 kb (Tooze, 1981). As a model system for eukaryotic gene expression, adenoviruses have been widely studied and well characterized, which makes them an attractive system for development of adenovirus as a gene transfer system. This group of viruses is relatively simple to grow and manipulate, and exhibits a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B, which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by CTLs and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991).

As only a small portion of the viral genome appears to be required in cis (Tooza, 1981), adenovirus-derived vectors offer excellent potential for the substitution of large DNA fragments when used in connection with cell lines such as 293 cells. Ad5-transformed human embryonic kidney cell lines (Graham, 1977) have been developed to provide the essential viral proteins in trans. The characteristics of adenoviruses render them good candidates for use in targeting cells in vivo (Grunhaus and Horwitz, 1992).

Particular advantages of an adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

In general, adenovirus gene transfer systems are based upon recombinant, engineered adenovirus that is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 kilobases of foreign DNA and can be grown to high titers in 293 cells (Stratford-Perricaudet and Perricaudet, 1991). Surprisingly persistent expression of transgenes following adenoviral infection has also been reported.

iii. AAV Vectors

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Lebkowski, 1988; McLaughlin, 1988; Laughlin, 1986; Tratschin, 1984). Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt, 1994; Shelling and Smith, 1994; Yoder, 1994; Zhou, 1994; Samulski, 1989; Lebkowski, 1988; McLaughlin, 1988; Tratschin, 1985; Hermonat and Muzyczka, 1984) and genes involved in human diseases (Luo, 1994; Walsh, 1994; Wei, 1994; Flotte, 1992; Ohi; 1990). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Samulski, 1991; Kotin, 1990). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Muzyczka, 1992; Kotin, 1990; Samulski, 1989; McLaughlin, 1988).

Typically, recombinant AAV (rAAV) virus is made by cotransfecting a plasmid containing the gene of interest flanked by the two AAV terminal repeats (McLaughlin, 1988; Samulski, 1989; each incorporated herein by reference) and an expression plasmid containing the wild type AAV coding sequences without the terminal repeats, for example pIM45, (McCarty, 1991; incorporated herein by reference). The cells are also infected or transfected with adenovirus or plasmids carrying the adenovirus genes required for AAV helper function rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Clark, 1995; Yang, 1994). Cell lines carrying the rAAV DNA as an integrated provirus can also be used (Flotte, 1995).

iv. Other Viral Vectors as Expression Constructs

Other viral vectors may be employed as expression constructs in the present invention. Vectors derived from viruses such as vaccinia virus (Coupar, 1988; Ridgeway, 1988; Baichwal and Sugden, 1986), and herpes viruses may also be employed. These viruses offer several attractive features for various mammalian cells (Horwich, 1990; Friedmann, 1989; Coupar, 1988; Ridgeway, 1988; Baichwal and Sugden, 1986).

With the recent recognition of defective hepatitis B viruses, new insight was gained into the structure-function relationship of different viral sequences in vitro studies showed that the virus could retain the ability for helper-dependent packaging and reverse transcription despite the deletion of up to 80% of its genome (Horwich, 1990). This suggested that large portions of the genome could be replaced with foreign genetic material. The hepatotropism and persistence (integration) were particularly attractive properties for liver-directed gene transfer. Chang (1991) recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang, 1991).

d. Non-viral Transfer Methods

Several non-viral methods for the transfer of expression vectors into cultured mammalian cells also are contemplated by the present invention. These include calcium phosphate precipitation (Graham and Van Der Eb, 1973; Chen and Okayama, 1987; Rippe, 1990) DEAE-dextran (Gopal, 1985), electroporation (Tur-Kaspa, 1986; Potter, 1984), direct microinjection (Harland and Weintraub, 1985), DNA-loaded liposomes (Nicolau and Sene, 1982; Fraley, 1979) and lipofectamine-DNA complexes, cell sonication (Fechheimer, 1987), gene bombardment using high velocity microprojectiles (Yang, 1990), polycations (Boussif, 1995), and receptor-mediated transfection (Wu and Wu, 1988; Wu and Wu, 1987). Some of these techniques may be successfully adapted for in vivo or ex vivo use.

C. Treatment to Prevent the Development of AIDS

A method of the present invention includes treatment to prevent either an HIV-infected or an uninfected subject from developing AIDS. The subject first can be evaluated for the ability to demonstrate an HLA-Cw7-restricted CTL response. According to the present invention, a positive result in the HIV-infected or uninfected patient suggests a method of treatment that can be administered to prevent the onset of AIDS.

A method of treating subjects includes the administration of HIV polypeptides or peptides. In some embodiments, the treatment includes the administration of HIV env-derived peptides individually or in combination. In other embodiments, the treatment is administered in the presence of adjuvants or carriers. While in others, the use of peptide-pulsed dendritic cells is also contemplated. Furthermore, in some examples, treatment comprises administration of HIV peptides or polypeptides and other AIDS treatment such as AZT and HAART.

1. HLA-Cw7-restricted CTL Response

A method of preventing the development of AIDS is provided by the present invention. It involves testing a subject for the ability to exhibit an HLA-Cw7-restricted CTL response, which is an HIV-specific response that was not known prior to this invention. HLA-Cw7 provides a genetic marker to identify patients who may respond favorably to treatment that will prevent the onset of AIDS. The target and effector cells used to determine this type of T-cell response are discussed in the previous section.

In addition to directly stimulating the CTL response with an HIV CTL epitope, it may prove useful to enhance this response by stimulating related helper T cell responses. Helper cells recognize an antigen-MHC class II complex, become activated and secrete various cytokines, which then activate other specific and nonspecific effector cells of the immune system including CTLs. Helper cells usually express CD4 on their surface and are stimulated by IL-2, IL-10, IL-12, TNF-α, α- and γ-interferon.

2. Polypeptides and Epitopic Core Sequences

The present invention contemplates the administration of HIV polypeptides or peptides that contain an HIV-specific CTL epitope to effect a treatment therapy to prevent the development of AIDS. Methods for preparing a polypeptide are previously described herein. Procedures for peptide production are also discussed in the "Diagnostics" section herein, and further descriptions are provided below.

Peptides corresponding to one or more antigenic determinants, or "epitopic core regions," of HIV polypeptides or HIV polypeptide fragments of the present invention can also be prepared. Such peptides should generally be at least five or six amino acid residues in length, will preferably be about 10, 15, 20, 25 or about 30 amino acid residues in length, and may contain up to about 35–50 residues or so.

In some methods of the present invention three peptides (#61, 63, and 104) are administered individually or combinatorially to a subject (see earlier discussion, infra). The peptides encode conserved regions within the envelope protein of HIV-1 (TABLE 4). Peptide 104 (aa 45–55) is from amino end of surface env protein gp120. Peptides 63 and 61 (aa 519–543, aa 586–598) are from the transmembrane protein gp41.

In a previous study, 19 synthetic peptides from the env protein gp160 of HIV-1 were tested for their ability to elicit an antibody response and to elicit T-cell proliferation in mice (Sastry, 1991). Five peptides (104, 106, 107, 113, and 63) induced proliferative responses to both the immunizing peptide and the recombinant HIV Env protein gp160. Moreover, peptides 61, 63, 103, 104, and 113 did not produce antibodies that could recognize recombinant gp160, but exclusively induced T-cell proliferation against the immunizing peptide and the HIV Env protein in mice strains representing four MHC haplotypes.

In another study, a mixture of peptides were used for immunization of monkeys (Nehete, 1993). Results demonstrated a good proliferative response by PBMCs to peptides 104, 111, and 63. Two of three monkeys showed good responses also to peptide 61. In both of these studies, however, only proliferative response was assayed.

Furthermore, a 15-amino acid peptide (aa 315–329) from the V3 loop of gp120 (peptide R15K) caused a rapid induction of peptide-specific and gp160-specific CD8+ CTLs as determined in mice using a lysis assay (Sastry & Arlinghaus, 1992).

Two of the three peptides that are encompassed by the present invention overlap with CTL epitopes that have been reported to be presented by different HLA class I molecules (Dupuis, 1995; Dai, 1992; Jassoy, 1992; Johnson, 1992; Dadaglio, 1991). A 25 amino acid peptide from the transmembrane portion of the envelope protein, gp41, recognized as a HLA-B14-restricted CTL epitope (Dupuis, 1995), overlaps with peptide 61, a composition encompassed by some methods of this invention (see TABLE 4).

Further, the CTL clone recognizing this 25 amino acid peptide was also described to be group-specific because target cells expressing envelope variants, exhibiting minor amino acid substitutions within the region covered by peptide 61, were efficiently lysed (Jassoy, 1992). Johnson et al. (1992) reported that a truncated version of peptide 61, comprising the first 11 amino acids (586–596), was recognized as an HLA-B8-restricted CTL epitope, while another overlapping peptide comprising 9 amino acids (584–592) was identified as an HLA-B14-restricted epitope by cloned CTLs from HIV-positive individuals.

A third report, by Dai et al. (1992) described an HLA-A24-restricted CTL clone that failed to recognize a peptide identical to the first 8 amino acids of peptide 61 because of a single amino acid substitution (lysine to argenine) at position 2. Thus, the region comprising peptide 61 in gp41 seems to be highly immunogenic in that there are epitopes recognized by CTLs in the context of multiple HLA molecules, and single amino acid changes could potentially lead to immune escape mechanisms.

The peptide 104 is part of a 22 amino acid sequence recognized by HLA-A2-restricted CTLs from HIV-seropositive individuals (Dadaglio, 1991). More recently, Dupuis et al. (1995) identified a 9 amino acid peptide, overlapping at its carboxyl terminus with the first 5 amino acids of peptide 104, as the minimal epitope recognized by CTLs in the context of HLA-A*0201. Peptide 104 has tyrosine, valine and tryptophan at positions 2, 5 and 7, respectively.

Peptide 61 has tyrosine, aspartic acid and leucine at positions 1, 4 and 8, respectively. Many of these residues seem to coincide with the specifications described by Falk et al. (1993) for binding to HLA-Cw7.

Synthetic peptides generally will be about 35 residues long, which is the approximate upper length limit of automated peptide synthesis machines, such as those available from Applied Biosystems (Foster City, Calif.). Longer peptides may also be prepared, e.g., by recombinant means.

U.S. Pat. No. 4,554,101, (Hopp) incorporated herein by reference, teaches the identification and preparation of epitopes from primary amino acid sequences on the basis of hydrophilicity. Through the methods disclosed in Hopp, one of skill in the art would be able to identify epitopes from within an amino acid sequence such as the HIV env polypeptide.

Numerous scientific publications have also been devoted to the prediction of secondary structure and to the identification of epitopes, from analyses of amino acid sequences (Chou & Fasman, 1974a,b; 1978a,b, 1979). Any of these may be used, if desired, to supplement the teachings of Hopp in U.S. Pat. No. 4,554,101.

Moreover, computer programs are currently available to assist with predicting antigenic portions and epitopic core regions of proteins. Examples include those programs based upon the Jameson-Wolf analysis (Jameson & Wolf, 1998; Wolf, 1988), the program PepPlot® (Brutlag, 1990; Weinberger, 1985), and other new programs for protein tertiary structure prediction (Fetrow & Bryant, 1993). Further commercially available software capable of carrying out such analyses is termed MacVector® (IBI, New Haven, Conn.).

In further embodiments, major antigenic determinants of a polypeptide may be identified by an empirical approach in which portions of the gene encoding the polypeptide are expressed in a recombinant host, and the resulting proteins tested for their ability to elicit an immune response. For example, PCR™ can be used to prepare a range of peptides lacking successively longer fragments of the C-terminus of the protein. The immunoactivity of each of these peptides is determined to identify those fragments or domains of the polypeptide that are immunodominant. Further studies in which only a small number of amino acids are removed at each iteration then allows the location of the antigenic determinants of the polypeptide to be more precisely determined.

Once one or more such analyses are completed, polypeptides are prepared that contain at least the essential features of one or more antigenic determinants. Minigenes or gene fusions encoding these determinants can also be constructed and inserted into expression vectors by, standard methods, for example, using PCR™ cloning methodology.

The use of such small peptides for vaccination typically requires conjugation of the peptide to an immunogenic carrier protein, such as hepatitis B surface antigen, keyhole limpet hemocyanin or bovine serum albumin. Methods for performing this conjugation are well known in the art.

3. Pharmaceutical Compositions and Routes of Administration

The present invention contemplates a diagnostic method and a method of preventing the development of AIDS. In some embodiments, pharmaceutical compositions are administered to a subject. Different aspects of the present invention involve administering an effective amount of an aqueous compositions. For example, to raise the level of HLA-Cw7 haplotype expressed, a patient can be given a composition comprising γ-interferon. In another embodiment of the present invention, HIV polypeptides or peptides may be administered to the patient to prevent the development of AIDS. Alternatively, an expression vector encoding such polypeptides or peptides may be given to a patient as a preventative treatment. Additionally, such compounds can be administered in combination with treatment by HAART or by administration of AZT, or both. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention can be formulated for parenteral administration, e.g., formulated for injection via the intravenous, intramuscular, subcutaneous, or even intraperitoneal routes. The preparation of an aqueous composition that contains a compound or compounds that increase the expression of an MHC class I molecule will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils.

The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

In certain cases, the therapeutic formulations of the invention also may be prepared in forms suitable for topical administration, such as in cremes and lotions. These forms may be used for treating skin-associated diseases, such as various sarcomas.

Administration of therapeutic compositions according to the present invention will be via any common route so long as the target tissue is available via that route. This includes oral, nasal, buccal, rectal, vaginal, mucosal, or topical. Alternatively, administration will be by orthotopic, intradermal subcutaneous, intramuscular, intraperitoneal, intravaginal, intranasal, or intravenous injection. Such compositions would normally be administered as pharmaceutically acceptable compositions that include physiologically acceptable carriers, buffers or other excipients. For treatment of conditions of the lungs, aerosol delivery to the lung is contemplated. Volume of the aerosol is between about 0.01 ml and 0.5 ml. Similarly, a preferred method for treatment of colon-associated disease would be via enema. Volume of the enema is between about 1 ml and 100 ml.

In certain embodiments, it may be desirable to provide a continuous supply of therapeutic compositions for a period of time to the patient. The time frame includes administration for one or more hours, one or more days, one or more weeks, or one or more months, with a possible hiatus during that time period. For intravenous or intraarterial routes, this is accomplished by drip system. For topical applications, repeated application would be employed. For various approaches, delayed release formulations could be used that provided limited but constant amounts of the therapeutic agent over and extended period of time. For internal application, continuous perfusion, for example with a synthetic HIV peptide, of the region of interest may be preferred. This could be accomplished by catheterization, post-operatively in some cases, followed by continuous administration of the therapeutic agent. The time period for perfusion would be selected by the clinician for the particular patient and situation, but times could range from about 1–2 hours, to 2–6 hours, to about 6–10 hours, to about 10–24 hours, to about 1–2 days, to about 1–2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, Remington's Pharmaceutical: Sciences, 1990). Some variation in dosage will necessarily occur depending on the condition of the subject being treated. The person responsible for administration will, in any event, determine the appropriate dose for the individual subject.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular therapeutic substance.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

a. In Vitro, Ex Vivo, In Vivo Administration

As used herein, the term in vitro administration refers to manipulations performed on cells removed from an animal, including, but not limited to, cells in culture. The term ex vivo administration refers to cells which have been manipulated in, vitro, and are subsequently administered to a living animal. The term in vivo administration includes all manipulations performed on cells within an animal.

In certain aspects of the present invention, the compositions may be administered either in vitro, ex vivo, or in vivo. In certain in vitro embodiments, autologous B-lymphocyte cell lines are incubated with a vaccinia virus vector of the instant invention for 24 to 48 hours or with synthetic HIV peptides for two hours. The transduced cells can then be used for in vitro analysis, or alternatively for in vivo administration.

U.S. Pat. Nos. 4,690,915 and 5,199,942, both incorporated herein by reference, disclose methods for ex vivo manipulation of blood mononuclear cells and bone marrow cells for use in therapeutic applications.

In vivo administration of the compositions of the present invention are also contemplated. Examples include, but are not limited to, transduction of bladder epithelium by administration of the transducing compositions of the present invention through intravesicle catheterization into the bladder (Bass, 1995), and transduction of liver cells by infusion of appropriate transducing compositions through the portal vein via a catheter (Bao, 1996). Additional examples include direct injection of tumors with the instant transducing compositions, and either intranasal or intratracheal (Dong, 1996) instillation of transducing compositions to effect transduction of lung cells.

b. Vaccines

The present invention includes methods for preventing the development of AIDS in both infected and uninfected persons who have an HLA-Cw7 haplotype. As such, the invention contemplates vaccines for use in both active and passive immunization embodiments. Immunogenic compositions, proposed to be suitable for use as a vaccine, may be prepared most readily directly from immunogenic HIV peptides prepared in a manner disclosed herein. Preferably the antigenic material is extensively dialyzed to remove undesired small molecular weight molecules and/or lyophilized for more ready. formulation into a desired vehicle.

Alternatively, other viable and important options for a peptide-based vaccine involve introducing the peptide sequences as nucleic acids, either as direct DNA vaccines or recombinant vaccinia virus-based polyepitope vaccine. In this regard, recent reports described construction of recombinant vaccinia viruses expressing either 10 contiguous minimal CTL epitopes (Thomson, 1996) or a combination of B cell, CTL, and $T_H$ epitopes from several microbes (An, 1997), and successful use of such constructs to immunize mice for priming protective immune responses. Thus, there is ample evidence in the literature for successful utilization of peptides, peptide-pulsed APCs, and peptide-encoding constructs for efficient in vivo priming of protective immune responses, in particular, CMI.

In case of HIV, an immunodominant CTL epitope sequence from the V3 loop region, that we and others reported to induce CTL responses in mice (Sastry, 1991; Nehete, 1994; Nehete, 1995), has been reported to prime CTL immunity when administered as a DNA vaccine that expressed the peptide as a minigene construct (Ciernik, 1996). Methods of the present invention involve the preparation and use of DNA vaccine constructs encoding the six different peptides from the highly conserved HIV envelope sequences as minigene products. In this regard, Wang et al. recently reported successful induction of $CD8^+$ T cell responses in rhesus monkeys immunized intramuscularly with a mixture of DNA plasmids encoding four different proteins of *Plasmodium falciparum*. The use of nucleic acid sequences as vaccines is described in U.S. Pat. Nos. 5,958, 895 and 5,620,896.

The preparation of vaccines that contain HIV peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

Imaoka et al. reported the induction of antigen-specific $CD4^+$ and $CD8^+$ cell responses in the systemic and mucosal compartments of rhesus macaques immunized by the intranasal route with p55gag of SIV mixed with the mucosal adjuvant, cholera toxin (CT). Also, it has recently been reported that mucosal immunization of mice by the intranasal or intravaginal routes with an herpes virus antigen resulted in induction of anti-viral CTL response at the mucosal sites that lasted for over 18 months (Gallichan, 1996).

*Cholera* toxin (CT), an ADP-ribosylating enzyme, produced by *Vibrio cholera*, is a potent, non-replicating oral immunogen that induces vigorous systemic and; mucosal immunity (Pierce, 1984). The immune response to CT has an extended memory (Lycke, 1986) and is T-cell dependent. It has also been shown that CT enhances the costimulatory activity of antigen presenting cells by differentially up-regulating B7.2 expression, an effect that appears to be important for its mucosal adjuvancity and immunogenicity (Cong, 1997). CT also has been shown to induce CTL responses when administered intranasally with HIV-1 gp120 encoding CTL epitope (Porgador, 1997).

Because of negative physiological effects, a mutated CT, (CT-2*) lacking adenosine diphosphate ribose (ADP-ribose) transferase activity has been purified, with no biological activity in animals. In such a CT mutant, $Arg^7$ and $Glu^{112}$ have been replaced by site-directed mutagenesis to Lys and Gln, respectively which abrogated CT's ability to increase cAMP levels in eukaryotic cells and to evoke fluid secretory responses in animals (Peterson, 1999). In addition, the B-subunits purified from native CT and CT-2* both stimulated the release of $[^3H]$-AA from S49 cyc$^-$ cells and murine monocyte/macrophage cells (RAW 264.7), suggesting a receptor-mediated cell activation process of potential importance in enhancing immune responses to vaccine components. The present invention includes methods of employing HIV peptides when used in conjunction with native CT for intranasal immunization.

Another bacterial toxin Aeromonas cytotoxic enterotoxin (Act) can be employed as a mucosal adjuvant in conjunction with the methods of the present invention. Aeromonas is an emerging human pathogen, which causes septicemia and gastroenteritis (Merino, 1995; Yamada, 1997). Gastroenteritis due to Aeromonas infections could be caused by two categories of enterotoxins—cytotonic and cytotoxic (Keusch, 1975). These unique enterotoxins have been purified to homogeneity and extensively studied (Chopra, 1996; Chopra, 1994; Ferguson, 1997; Xu, 1998).

Substitution of some aa residues e.g., $Tyr^{256}$ to Ser reduced cytotoxic activity, but had no effect on the hemolytic and enterotoxic activity of Act (Ferguson, 1995). Replacement of $His^{209}$ to Asn affected the cytotoxic and enterotoxic activities but the hemolytic activity remained unchanged. Interestingly, replacement of $Asn^{177,178}$ to Thr and $Asp^{179}$ to Glu reduced hemolytic and cytotoxic activity, but the enterotoxic activity was not affected. Similar results were noted when $His^{355}$ was changed to Asn. Some of the aa residues (e.g., $Tip^{270}$, $Gly^{274}$, $Trp^{394}$, and $His^{144}$) appeared important for all three biological activities (Ferguson, 1995). Such mutated Act molecules may be coadministered, for example, as a vaccine, in the methods of the present invention to enhance a CTL response to the HIV peptides and polypeptides disclosed herein.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The HIV-derived peptides and HIV-encoded DNA constructs of the present invention may be formulated into the vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin, mixture with bacterial cells such as C. parvum or endotoxins or lipopolysaccharide components of Gram-negative bacteria, emulsion in physiologically acceptable oil vehicles such as mannide monooleate (Aracel A), or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

c. Viruses as Therapeutic Compositions

The engineered viruses of the present invention may be administered directly into animals, or alternatively, administered to cells that are subsequently administered to animals. The viruses can be combined with the various β-interferon inhibiting formulations to produce transducing formulations with greater transduction efficiencies. A discussion of suitable viruses is presented above.

d. Treatment Additives i. Carrier Molecules

As is well known in the art, a given composition may vary in its immunogenicity. It is often necessary therefore to boost the host immune system, as may be achieved by coupling the HIV peptide or polypeptide immunogen to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

ii. Adjuvants

As is also well known in the art, the immunogenicity of HIV polypeptide or peptide composition can be enhanced by the use of non-specific stimulators of the immune response, known as adjuvants. Suitable adjuvants include all acceptable immunostimulatory compounds, such as cytokines, toxins, or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-12 or genes encoding proteins involved in immune helper functions, such as B-7.

T-helper peptides may also be coadministered with the HIV polypeptides, peptides, or their corresponding nucleic acid sequences of the present invention to improve CTL induction (Del Guercio et al., 1997; Mortara et al., 1999). For example, a lipopeptide that include a promiscuous human helper T cell (Th) epitope from a tetanus toxoid peptide increased a CTL induction response to various SIV peptides (Mortara et al., 1999). The sequence of this peptide (aa 830–aa 846) had the following sequence: QYIKANSKFIGITELKK, with a lipid moiety attached at one end. Other T-helper promiscuous peptides can be used in the methods of the invention such as PADRE epitopes, which have been characterized as binding to different HLA-DR entities (Del Guercio, et al., 1997).

e. Combination Therapies

Of course it is understood that the method of the present invention, particularly administration of HIV polypeptides or peptides to a patient, may also be used in combination with the administration of traditional therapies. Some such therapies are described below.

i. AZT

A well-known, traditional therapy for the treatment of AIDS involves zovidovudine (AZT™ available from Burroughs Wellcome). This is one of a class of nucleoside analogues known as dideoxynucleosides which block HIV replication by inhibiting HIV reverse transcriptase. The anti-AIDS drug zidovudine (also known as AZT) may also be used in limited circumstances, mostly in combination with rifampin, as described by Burger et al. (1993).

The compositions and methods disclosed herein will be particularly effective in conjunction with other forms of therapy, such as AZT and/or protease inhibitors that are designed to inhibit viral replication, by maintaining desirable levels of white blood cells. This, in effect, buys the patient the time necessary for the anti-viral therapies to work.

ii. HAART

New combination drug therapy has shown promising results in the treatment of HIV-infected patients. Treatment with potent anti-HIV drug combinations is referred to as "highly active antiretroviral therapy" (HAART), and it has provided clinical improvement, longer survival, and improved quality of life for people infected with HIV during all four stages of HIV disease. Examples of HAART include a protease inhibitor (indinavir, nelfinavir, ritonavir, ritonavir/saquinavir, or saquinavir) combined with two nucleoside analogs (AZT/ddI, d4T/ddI, AZT/ddC, AZT/3TC, or d4T/3TC).

D. EXAMPLES

Example 1

Materials and Methods

1. Patient Population

Blood samples were obtained from three volunteers who have been HIV-seropositive for more than 11 years and have not developed AIDS (designated as LTNPs), and from one individual infected in 1991 who remains asymptomatic. The details on the clinical status of the patients are included in TABLE 2. Blood samples collected from an HIV-seronegative volunteer were used as a control in many experiments.

TABLE 3

Clinical Status of Subjects

| Volunteer | HLA haplotypes A | B | C | Infection (date) | Clinical status | AZT treatment | CD4 (per mm$^3$) | p24 (pg/ml) |
|---|---|---|---|---|---|---|---|---|
| LB | A1 | B2/B13 | Cw7/C*15 | 1985 | LTNP | + | 617 | 4.9 |
| DH | A3 | B7/B55 | Cw3/Cw7 | 1985 | LTNP | – | 375 | UD |
| HD | A2/A3 | B7/B14 | Cw7/Cw8 | 1985 | LTNP | + | 154 | 9.5 |
| RLF | A2 | B7/B14 | Cw7/Cw8 | 1991 | AS | – | 464 | UD |

LTNP = Long-term nonprogressor
AS = Asymptomatic
UD = Undetectable

2. Peptide Synthesis.

Synthetic peptides corresponding to highly conserved sequences in the envelope protein of HIV-1 were employed in the present investigation. The peptides were synthesized as described earlier (Sastry, 1991) by the solid-phase method of Merrifield (Merrifield, 1963) either on a modified Vega 250 automatic peptide synthesizer (Vega Biochemicals, Tucson, Ariz.) or by the "Bag" method as described by Houghten (Houghten, 1985). In most of the experiments, the purity of the peptides used was approximately 70–80%, and in limited experiments peptides exhibiting >95% purity were used with identical results.

3. Lymphocyte Surface Marker Studies

Peripheral blood mononuclear cells (PBMCs) were assayed for the presence of T-cell surface markers using a whole blood staining procedure and samples were analyzed by flow cytometry (Epics-Profile, Coulter Corporation, Hialeah, Fla.). The relative percentages of the CD4$^+$ and CD8$^+$ lymphocyte populations were enumerated using direct immunofluorescence with phycoerythrin-conjugated mouse monoclonal antibodies Leu3A and Leu2A (Becton Dickinson, Mountain View, Calif.). Calculations of the absolute numbers of cell subpopulations were based on a complete blood cell count and a differential test done from Wright-Giemsa-stained blood smears. In certain experiments to determine the phenotype of the HIV-specific CTL effectors, freshly isolated PBMCs were subjected to fluorescent cell sorting, and populations of CD4$^+$ and CD8$^+$ cells were isolated and tested for CTL activity.

4. HLA Typing

Lymphocytes from all the donors used in this study were typed for HLA-A, -B, and -C antigens on unfractionated PBMCs by the Tissue Typing Laboratory at the Methodist Hospital, Baylor College of Medicine, Houston, Tex. Identification of the HLA alleles was further confirmed by PCR-SSP typing according to the method of Olerun and Zetterquist (Olerum, 1992).

5. Cytotoxic T Lymphocyte (CTL) Assay

The CTL assays were performed in round-bottom 96-well plates as described earlier (Sastry, 1992). Various concentrations of effector cells in 0.1 ml of RPMI-1640 medium containing 10% fetal calf serum (FCS) were added to 0.1 ml of a [$^{51}$Cr]-labeled target cell suspension [with $10^4$ cells/ml in the wells to give the described effector:target (E:T) ratios]. After a 6 hour incubation at 37° C., the supernatant was harvested from each well and the radioactivity was measured in a gamma counter (Wallac Inc., Gaithersburg, Md.). The assays were performed in triplicate wells, and the percentage of specific cell lysis was calculated by the formula 100×(mean experimental release−mean spontaneous release)/(mean maximum release−mean spontaneous release). Maximum release was determined from supernatants of cells that were lysed by adding 5% Triton X-100. Spontaneous release was determined from target cells incubated without added effector cells. All the results presented have a standard deviation value of less than 10%.

6. Target Cell Lines

Autologous B-lymphocyte cell lines (B-LCLs) were prepared by incubation of PBMCs with supernatant from the EBV-producing marmoset cell line B95.8 (ATCC: CRL-1612). All transformed cell lines were maintained in RPMI 1640 medium with 10% fetal calf serum (FCS). Recombinant vaccinia viruses expressing gp160 or gag of HIV-1 IIIB, and control vaccinia virus were obtained from the AIDS Research and Reference Reagent Program (Rockville, Md.; donated by Dr. B. Moss). Stock vaccinia virus preparations were produced by growth in HeLa cells and were titered by the standard plaque assay. Target B-LCLs were infected with either recombinant or control vaccinia viruses at a multiplicity of infection of 10 by culturing for 2 h at a concentration of $10^7$ cells/ml at 37° C. in 5% $CO_2$ in air (Sastry, 1992). Cultures were then diluted to a concentration of $10^6$ cells/ml., and cultured for an additional 16 hours and labeled with [$^{51}$Cr]sodium chromate for 2 h, washed thrice, and resuspended to give the appropriate concentration for use as target cells in the cytotoxicity assay. The peptide-pulsed targets were prepared by incubating the B-LCLs with [$^{51}$Cr] sodium chromate for 2 hours, and subsequently with 100 μg of synthetic peptide for another 2 hours.

7. Antibody Inhibition Studies

To determine the HLA class I specificity of the CTL response, the effector PBMCs were treated with a 1:100 dilution of W6/32, the class I-specific antibody, from the hybridoma culture supernatants (ATCC: HB95).

Example 2

HIV-seropositive Long-term Non-progressors Exhibit Envelope-specific CTL Responses Individuals designated as LTNPs were tested for the ability to exhibit an HIV envelope-specific T-cell response. Three of the four individuals in the study were classified as LTNPs because HIV infection established 12 years ago in these individuals did not result in symptomatic infection, despite some fluctuation in $CD4^+$ cell counts. The fourth individual was diagnosed to be HIV-positive relatively recently (since 1991) and was asymptomatic (TABLE 3). Blood samples collected from an HIV-seronegative volunteer (JR) served as control in all the experiments. The HLA profile of the control individual JR was determined to be HLA-A2/A28, -B35/B38, and -Cw4. Only in two of the four $HIV^+$ individuals we observed low plasma levels of p24 antigen (4.9 and 9.5 pg/ml, in LB and HD, respectively) by the acid-dissociation ELISA method using the Coulter ICD-Prep Kit.

The PBMCs isolated from freshly obtained heparinized blood samples from these individuals were used as effector cells to determine the HIV-specific CTL activity against autologous target B-LCLs infected with different recombinant vaccinia viruses expressing the envelope or gag proteins of HIV-1. Each of the four $HIV^+$ individuals exhibited CTL activity directed against the HIV-1 envelope protein as evidenced by the significant specific lysis values compared to that in the control HIV-individual (FIG. 1). The magnitude of CTL responses varied between the four individuals, with DH and RLF exhibiting relatively the higher envelope-specific CTL responses compared to HD and LB. It was possible to obtain blood samples over a two year period from these individuals for repeated analysis of CTL responses, and in all cases HIV-1 envelope-specific CTL activity was observed in the four $HIV^+$ individuals.

In two separate experiments, purified populations of $CD4^+$ and $CD8^+$ cells were also used and observed that the CTL activity was specific to the $CD8^+$ population. One of the individuals (HD) also exhibited significant gag-specific CTL responses. This patient, despite fluctuations in CD4 cell counts (154 and 670/mm$^3$, at two different time points) showed no significant changes in the CTL responses (compare data in FIGS. 1 and 2). Repeat samples from the other three subjects did not show appreciable differences in either $CD4^+$ cell counts or the nature and magnitude of the CTL responses.

Example 3

The HIV-envelope-specific CTL Response is HLA-Cw7 Restricted

Figure 2:
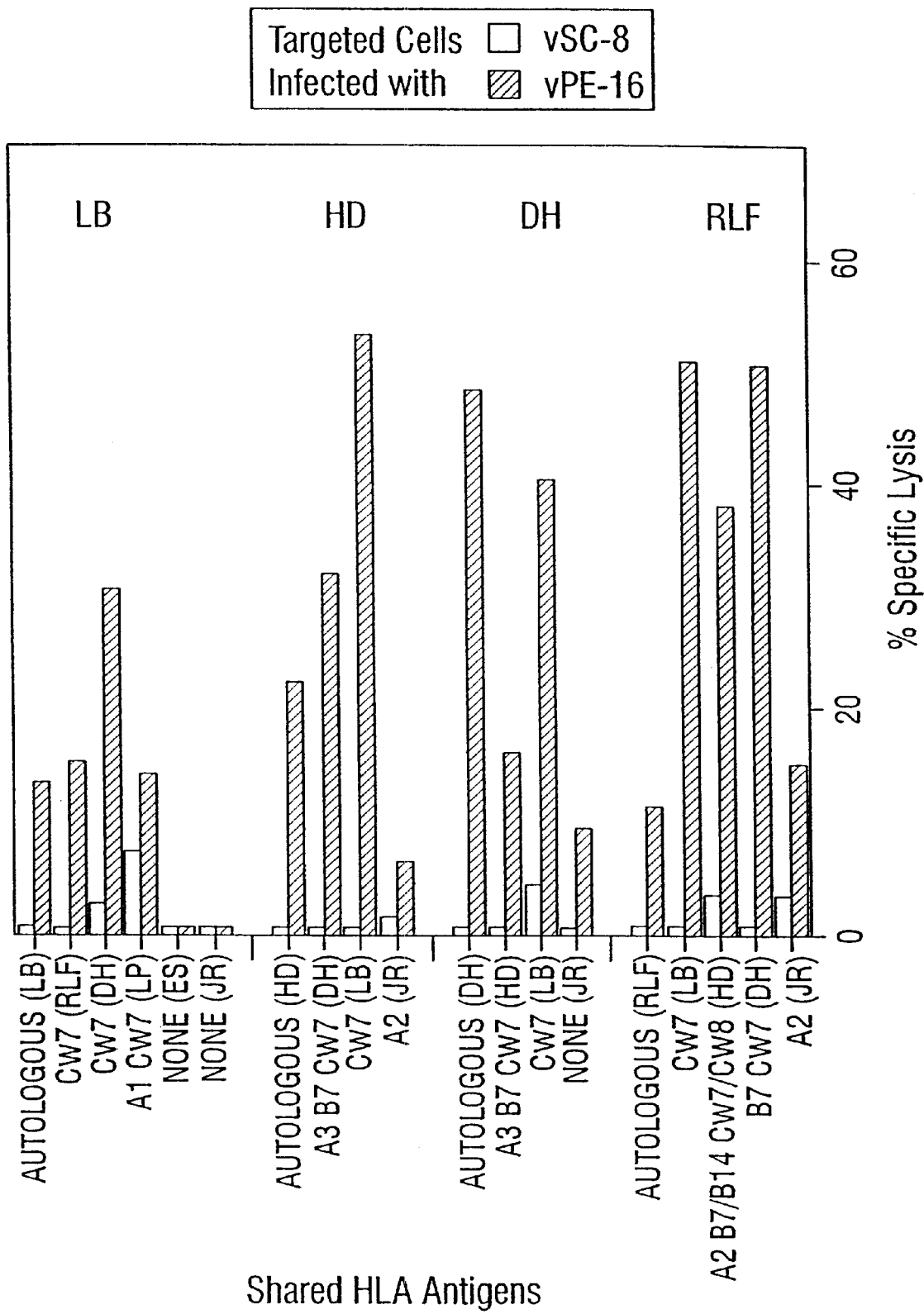
FIG. 2. Restriction by HLA-Cw7 of CTL Activity in HIV+ LTNPs. The PBMCs from four HIV+ LTNPs (LB, HD, DH, and RLF) were assayed for CTL activity against target cells comprised of both autologous and heterologous B-cell lines that share different HLA antigens as indicated to the left of the figure. The target cells in each case were infected with either control (vSC-8) or recombinant vaccinia virus expressing the envelope protein (vPE-16). The percent specific lysis values at an E:T ratio of 40:1 are shown.
Figure 3A:
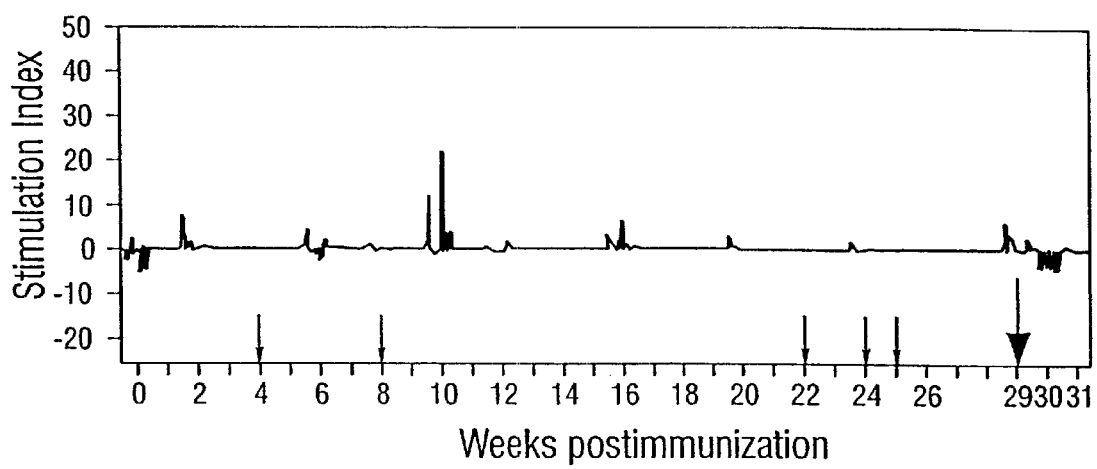
FIG. 3. Proliferative responses in control and vaccinated monkeys. Peripheral blood mononuclear cells (PBMC) from each of the five monkeys in the study were collected at various intervals as shown and tested for proliferative responses to various peptides and to heat-inactivated SHIV as antigens using the standard [$^3$H]thymidine incorporation assay. The results are expressed as stimulation index (SI) values calculated as fold-increases in proliferation with the test antigen compared to medium control. Also, the values were adjusted to an unrelated control peptide used (a helper T cell epitope peptide form the E7 oncoprotein of HPV-16).
Figure 3B:
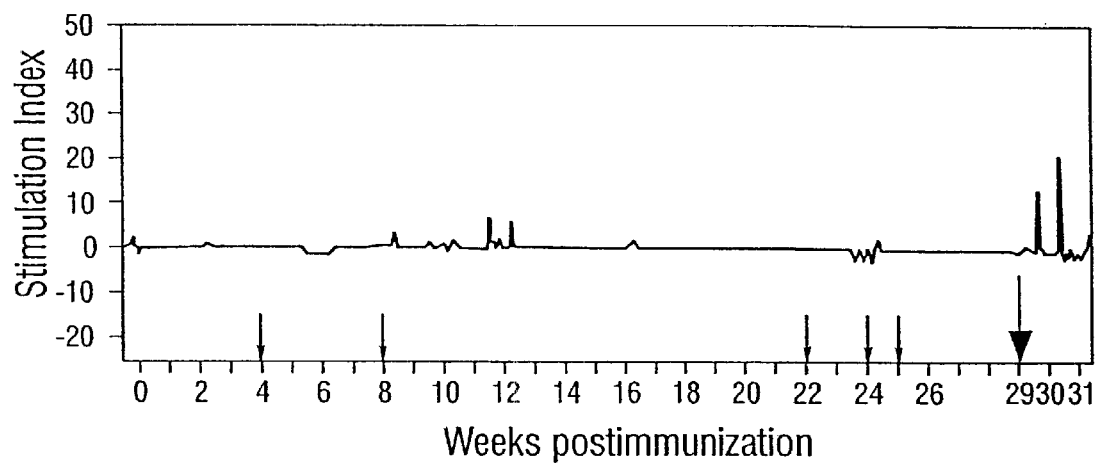
Figure 3C:
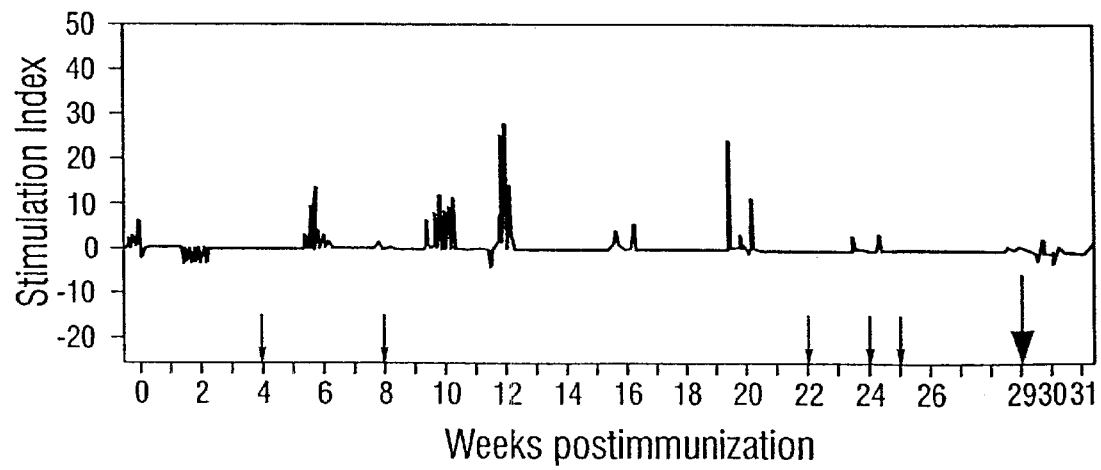
Figure 3D:
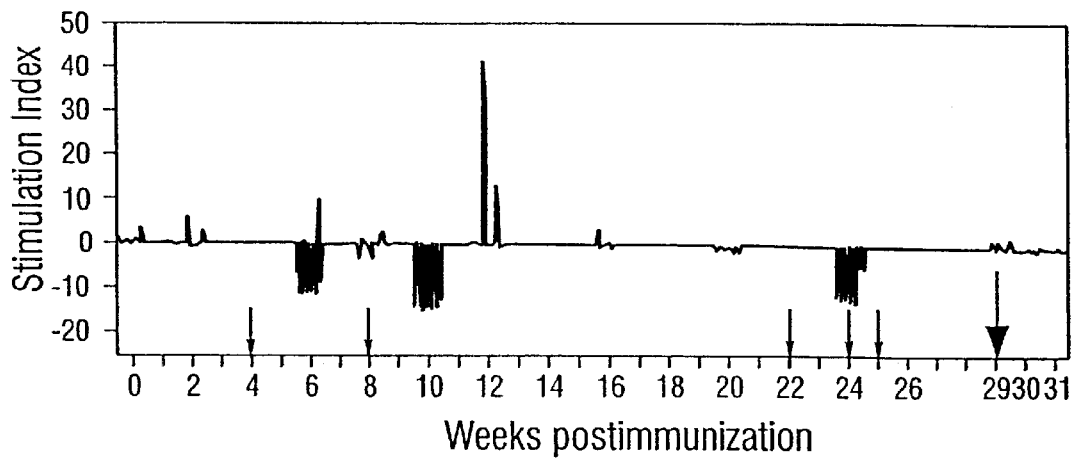
Figure 3E:
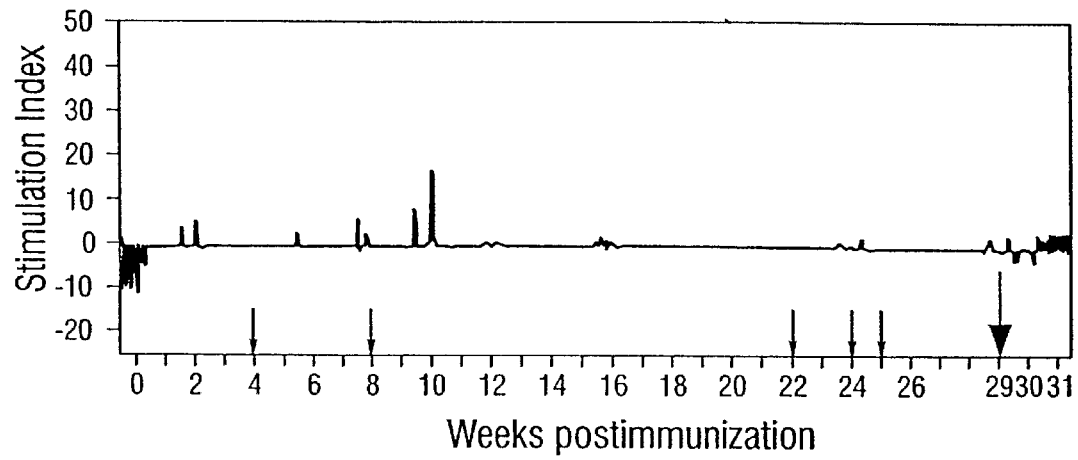
Figure 4A:
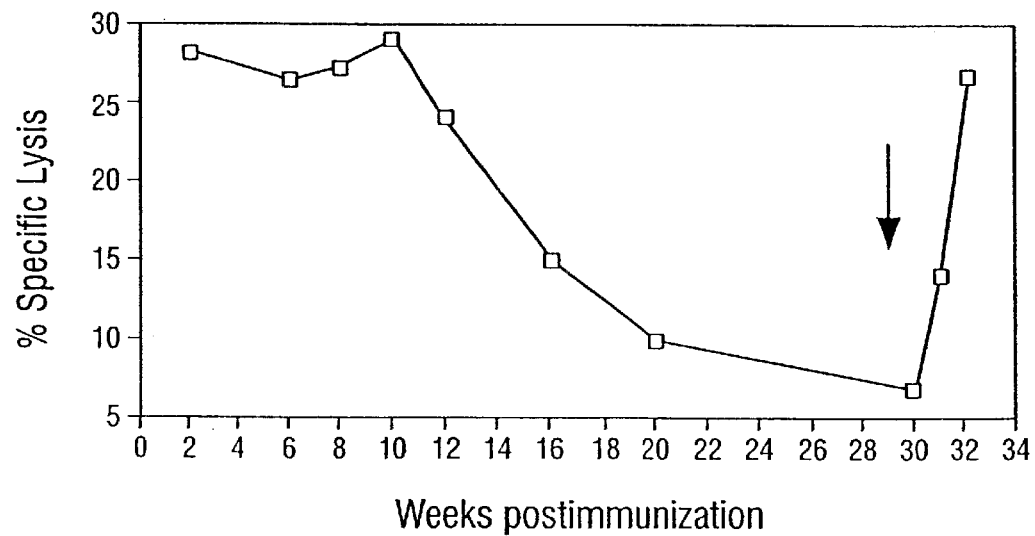
FIG. 4. NK activity of PBMC from the control and vaccinated monkeys. Freshly isolated PBMC from the monkeys were tested at various time points after immunization for NK activity against $^{51}$Cr-labelled K-562 target cells.
Figure 4B:
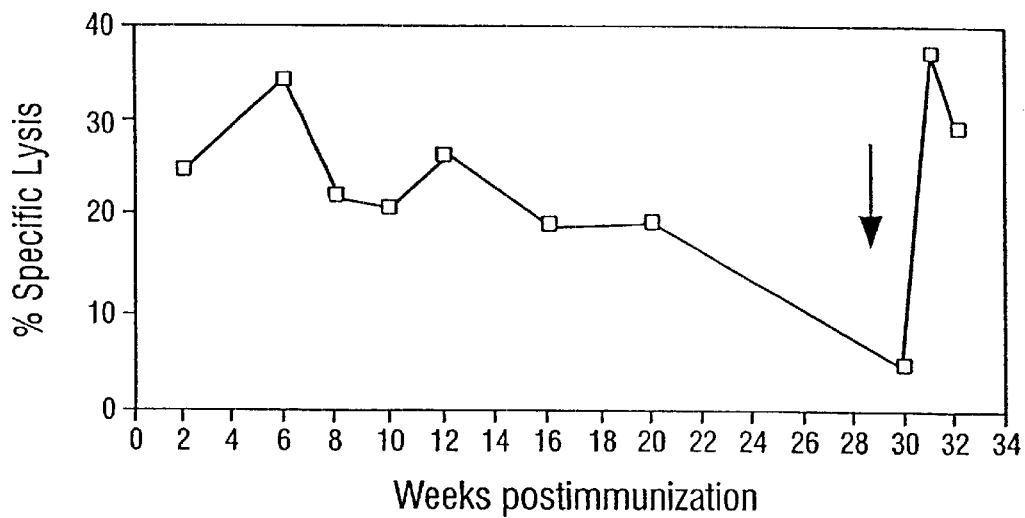
Figure 4C:
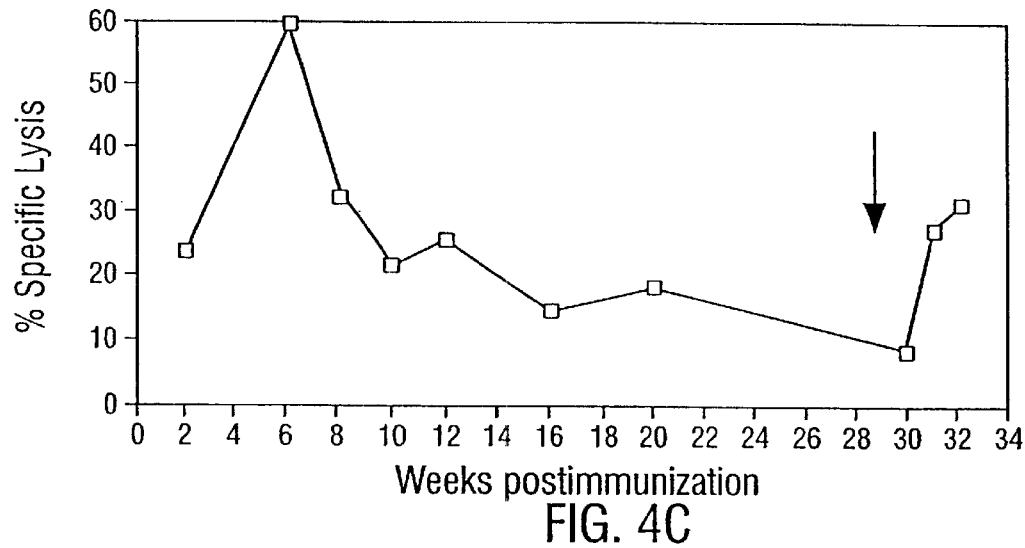
Figure 4D:
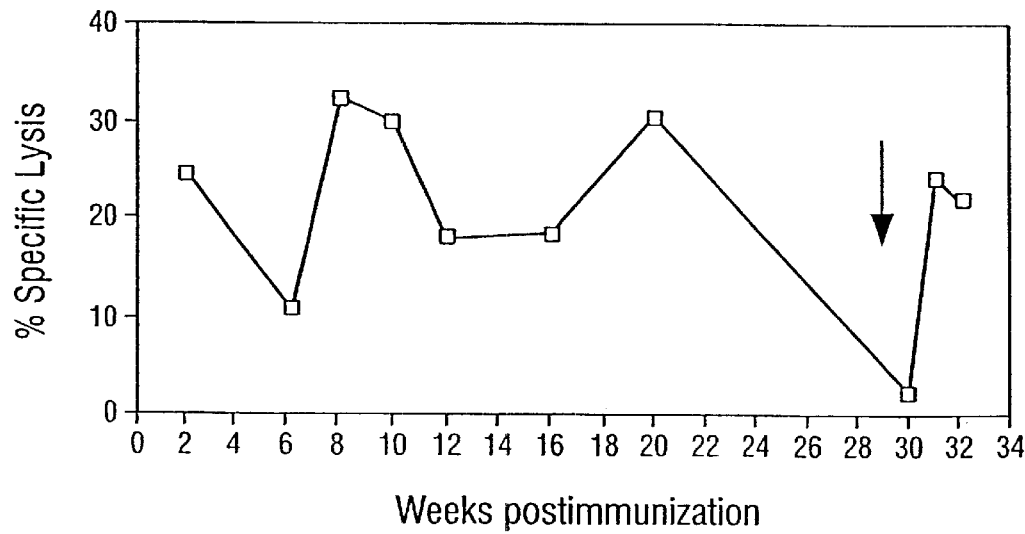
Figure 4E:
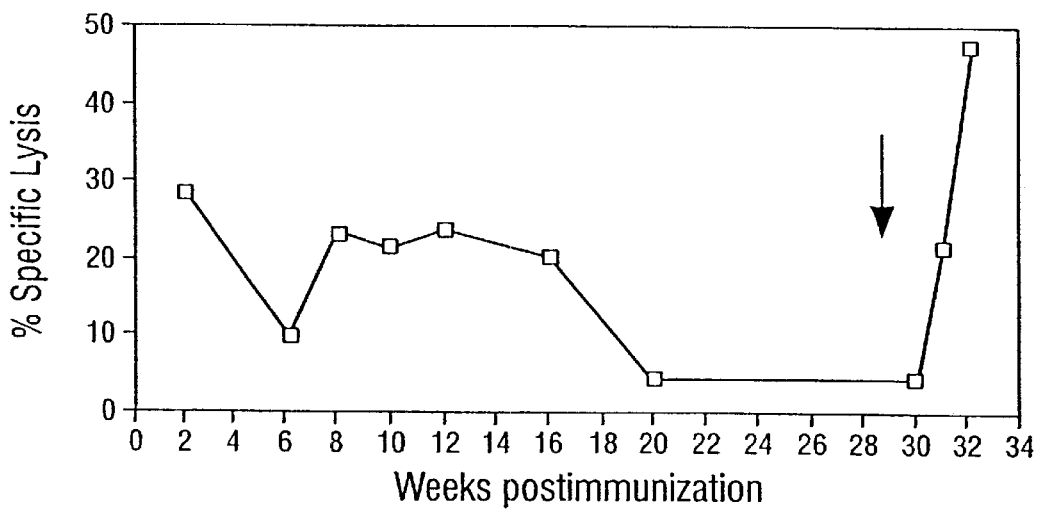
Figure 5A:
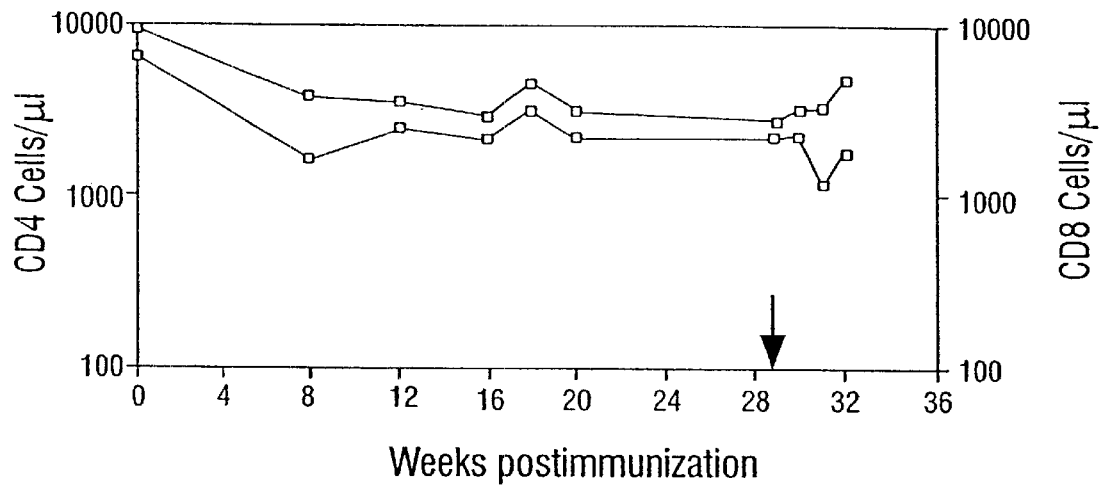
FIG. 5. Flow-cytometric analysis of CD4+ and CD8+ cells from the control and vaccinated monkeys. Freshly obtained blood samples from the monkeys were processed at various time points after immunization by flow-cytometry using specific anti-CD4 and anti-CD8 antibodies conjugated to PE and FITC, respectively.
Figure 5B:
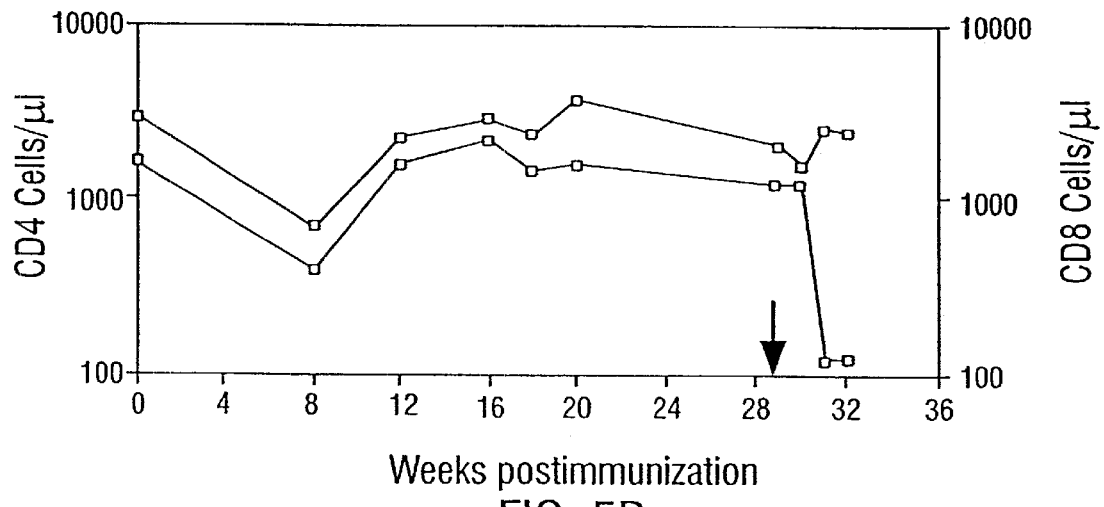
Figure 5C:
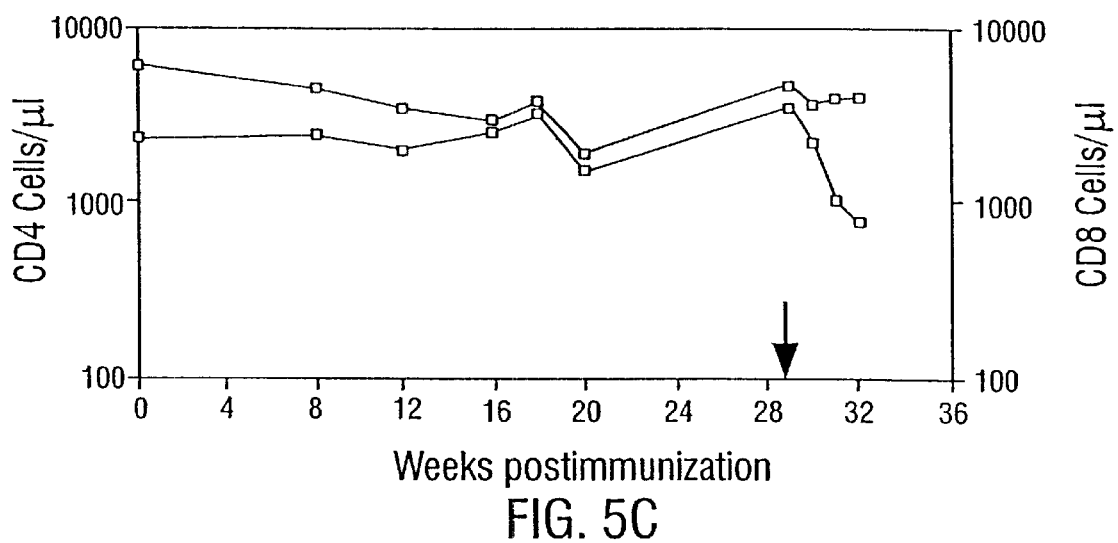
Figure 5D:
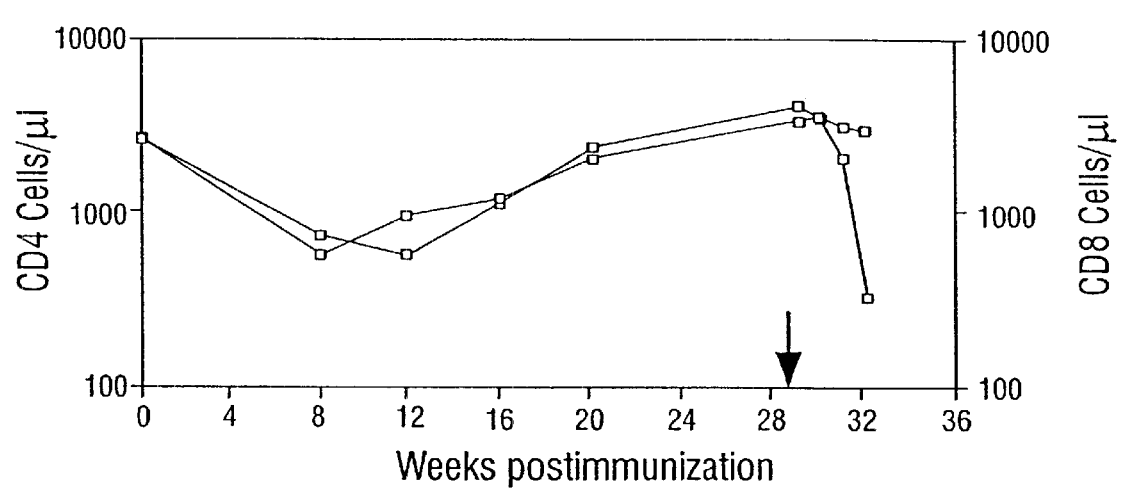
Figure 5E:
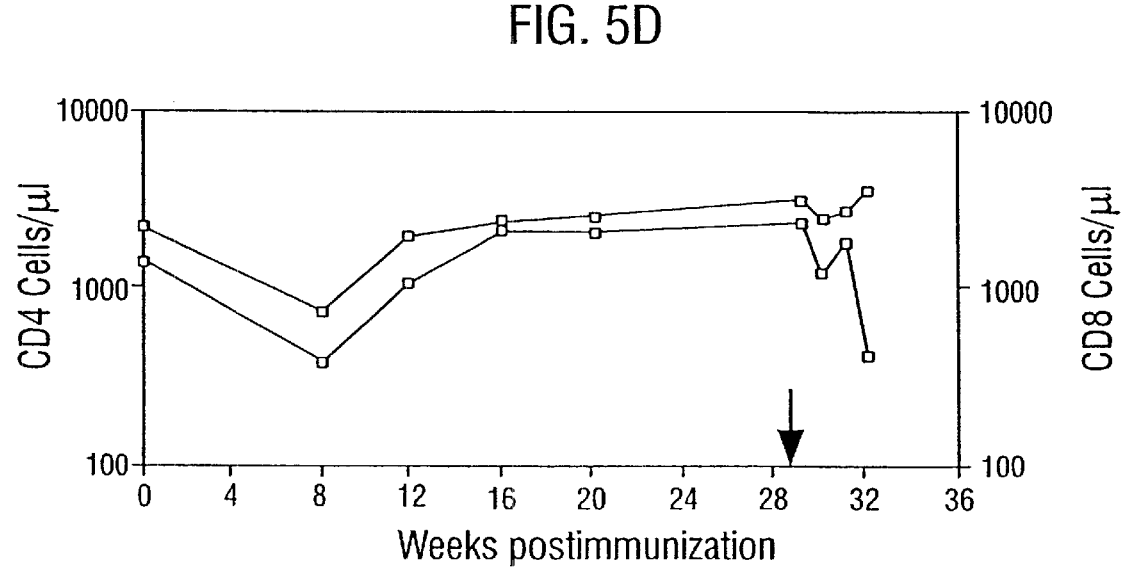
Figure 6A:
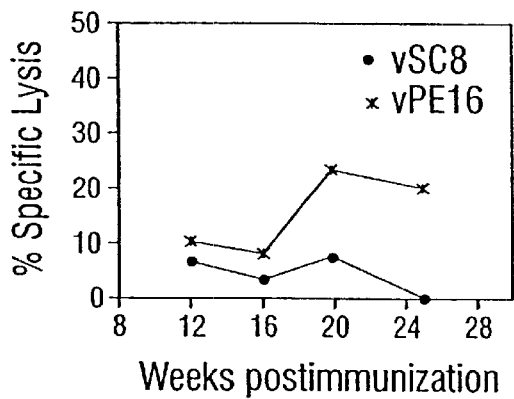
FIG. 6. HIV envelope-specific CTL activity in control and peptide-vaccinated monkeys. PBMC from two vaccinated monkeys (J13 and L889) and two controls (L913 and L933) were restimulated in vitro with peptide-pulsed DC for 14 days before testing for lysis of autologous $^{51}$Cr-labelled B-LCL target cells that were infected with either control or recombinant vaccinia virus-expressing HIV envelope protein (vSC8 and vPE16, respectively). PBMC were isolated from blood samples collected at different time points after vaccination, stimulated in vitro for two weeks with peptide-pulsed DC, and assayed by the standard chromium-release assays using autologous B-LCL targets infected with either control (vSC8) or recombinant vaccinia virus-expressing HIV envelope gp160 (vPE16). The CTL activity at an E:T ratio of 50:1 is shown.
Figure 6B:
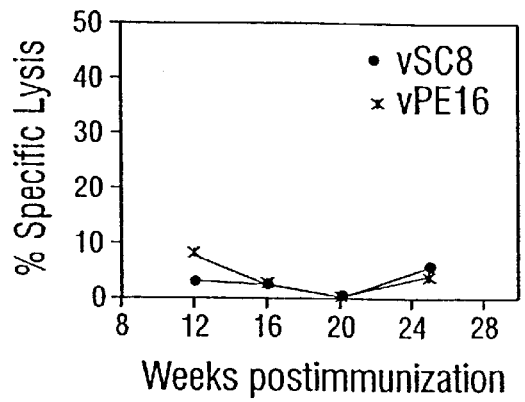
Figure 6C:
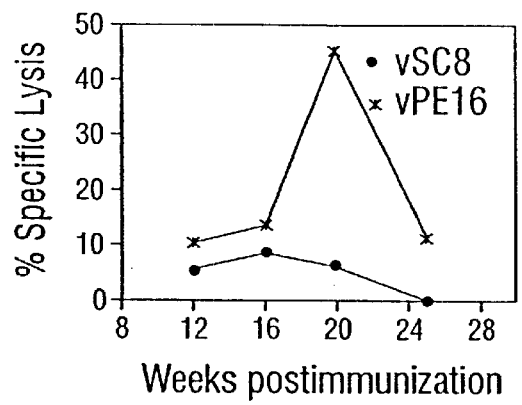
Figure 6D:
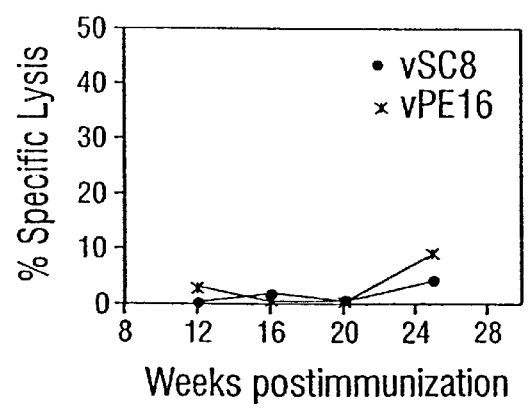

The HLA class I restriction of the CTL response in these individuals was confirmed by specific reduction in CTL activity in the presence of anti class I-specific antibody, W6/32. We used a 1:4 dilution of the culture supernatant from the W6/32-secreting hybridoma cells and observed a 73% reduction in HIV-1 envelope-specific CTL activity (specific lysis value decreasing from 23.2% to 6.2%, at an E:T ratio of 25:1) with PBMCs from LB as effector cells. To identify the class I locus involved in the CTL response of these individuals, we employed a number of target cell lines that shared different HLA-A, -B, and -C locus antigens with the effector CTLs. Since the CTL activity directed against the HIV-1 envelope was observed to be common in all four $HIV^+$ individuals, we used target cells infected with recombinant vaccinia viruses expressing the envelope protein for these studies. The data in FIG. 2 show that the HLA-Cw7 antigen serves as the restriction element for the HIV-1 envelope-specific CTL activity in the four $HIV^+$ individuals. The HLA-A1, -A2, -A3, and -B7 antigens were less frequently shared among the target cells lysed by the CTLs from all four individuals.

Example 4

The HIV-envelope-specific CTLs Recognize Epitopes From Highly Conserved Regions in the Envelope Protein Four HIV-derived peptides that consistently seemed to be T-cell epitopes in animal models (Nehete, 1993; Sastry, 1991) were selected for use in studies to test their capacity to sensitize autologous target cells for lysis by the HIV-specific CTLs in the LTNPs. PBMCs from one of the LTNPs (HD) were used as effector cells after restimulation for 7 days in vitro in the presence of the mitogen phytohemagglutinin (PHA).

Results showed significant CTL activity against autologous B-LCLs pulsed with three of the peptides (TABLE 4). These included peptide 104 (aa 45–55) from the amino-terminal portion of the surface envelope protein gp120, and peptides 63 and 61 (aa 519–543, and aa 586–598, respectively) from the trans-membrane protein gp41. Another peptide (#113, aa 204–216) from gp120 did not serve as a CTL epitope in these experiments. Specific lysis of target cells pulsed with peptides 104, 63, and 61 was also observed when PBMCs freshly isolated from the patient were used as CTL effectors, although to a lesser extent than that observed with the restimulated PBMCs.

When unstimulated PBMCs were used as effector cells they efficiently lysed autologous B-LCLs infected with recombinant vaccinia virus expressing gp160 (TABLE 4). Even though PHA-stimulated PBMCs also efficiently lysed the autologous target cells expressing gp160, they showed high levels of background lysis of autologous B-LCL targets infected with the control recombinant vaccinia virus, vSC-8. The background lysis was not due to EBV-specific CTL because uninfected B-LCL did not show any specific lysis.

to time by PCR analysis. The uninfected chimpanzees were housed at a location different than the location housing the infected chimpanzees. Even though blood samples were obtained from 5–8 animals, those from two of the uninfected chimpanzees (#CH40 and #CH73) are included in all the analyses as controls.

2. Patients

Heparinized blood samples were obtained from 17 HIV-infected volunteers to study the proliferative responses specific to peptides from conserved regions in the HIV-1 envelope protein. The patient population was comprised of both symptomatic and asymptomatic individuals with the majority undergoing anti-retroviral treatment. Details of their CD4+ cell counts, anti-retroviral medications, and clinical conditions were available for some of the individuals only. The HIV-positivity in all patients was confirmed by Western blot analysis and p24-antigen capture ELISA. Blood samples also were obtained from approximately ten normal HIV-seronegative volunteers, two of which were consistently analyzed in all the experiments as controls.

TABLE 4

Peptide-Specificity of CTL Response in an HIV-Seropositive LTNP

| Peptide No. | Residues | Peptide amino acid sequence[2] | % Specific lysis at various E:T ratios[3] | | | |
|---|---|---|---|---|---|---|
| | | | 100:1 | 50:1 | 25:1 | 12.5:1 |
| 61 | 586–598 | YLRDQQLLGIWGC (SEQ ID NO:33) | 15.0 | 14.5 | 4.0 | 4.0 |
| 63 | 519–543 | FLGFLGAAGSTMGAASLTLTVQ ARQ (SEQ ID NO:20) | 17.6 | 8.8 | 7.9 | 0 |
| 104 | 44–55 | VYYGVPVWKAE (SEQ ID NO:1) | 12.2 | 9.3 | 3.7 | 1.5 |
| 113 | 204–216 | SVITQACSKVSFE (SEQ ID NO:8) | 0 | 0 | 0 | 0 |
| | | Medium | | | | |
| | | vSC-8[4] | 2.9 | 2.2 | 3.0 | 1.6 |
| | | vPE-16[5] | 22.4 | 19.5 | 16.4 | 3.5 |

[1]The CTL activity was assayed using PBMCs from patient volunteer HD.
[2]The amino acid sequence of peptides was according to Modrow et al., J. Virol., 61:570–578, 1987.
[3]CTL activity of PBMCs restimulated for 7 days by growth in phytohemagglutinin medium was assayed against peptide-pulsed autologous EBV-transformed B cells (B-LCL).
[4]Freshly isolated PBMCs were assayed for CTL activity against B-LCL infected with control vaccinia virus.
[5]Freshly isolated PBMCs were assayed for CTL activity against B-LCL infected with recombinant vaccinia virus expressing gp160 from HIV-I HIB.

Example 5

Materials and Methods

1. Chimpanzees

Heparinized blood samples were obtained from HIV-infected and uninfected chimpanzees to determine the envelope peptide-specific proliferative responses. The nine HIV-infected animals were housed individually under conditions meeting animal biosafety requirements. Of the nine infected chimpanzees, six (#62, 100, 139, 175, 247 and 310) were infected with HIV-1 IIIB, two (#69 and 80) were infected with HIV-1 LAV (closely related to IIIB), and one chimpanzee (#99) was infected sequentially with HIV-1 strains NY-5 and IIIB.

The chimpanzees were between 11 years and 25 years of age and were HIV+ for 7–11 years as determined from time 3. Peptides Peptide sequences used in the present study are listed in TABLE 5 below.

TABLE 5

Amino acid sequence of synthetic peptides from conserved regions in the HIV-1 envelope protein

| Peptide no. | Amino acid residues | Amino acid sequence* |
|---|---|---|
| 104 | 45–55 | VYYGVPVWKEA (SEQ ID NO:1) |
| 113 | 204–216 | SVITQACSKVSFE (SEQ ID NO:8) |
| 120 | 586–598 | YLRDQQLLGIWG (SEQ ID NO:33) |
| 121 | 519–543 | FLGFLGAAGSTMGAASLTLTVQARQ (SEQ ID NO:20) |
| 122 | 417–435 | CRIKQIINMWQGVGKAMYA (SEQ ID NO:36) |

*The amino acid sequence of peptides was according to Modrow et al.

These peptides corresponding to conserved regions in the envelope protein of HIV-1 were identified as T-cell epitopes in mice and rhesus monkeys in our previous studies (Nehete, 1993; Sasty, 1991). Peptides were synthesized as described before (Sastry, 1991) using the Merrifield solid-phase method (Merrifield, 1963) either on a modified Vega 250 automatic peptide synthesizer (Vega Biochemical, Tucson, Ariz.) or by the "bag" method as described by Houghten (Houghten, 1985). In most of the experiments, the purity of the peptides used was approximately 70–80%, and in limited experiments, peptides exhibiting >95% purity were used with identical results. In addition to the conserved envelope peptides, a peptide from the c-mos proto-onogene (aa 158–170, STRTPEDSNSLGT (SEQ ID NO:37)) was used as a control in all the experiments. Additional control peptides used in majority of the experiments included: a peptide from the c-abl protooncogene, peptides from E6 and E7 oncoproteins of HPV-16, a peptide corresponding to the V3-loop region in gp120 but with a scrambled amino acid sequence, and peptides from the pol and gag regions of HIV-1. In all these cases, the amount of proliferative responses to the controls was consistently and significantly less than the amount of response the test peptides from the HIV envelope protein. In all these cases, the level of proliferative responses to the to the control peptide was consistently and significantly less than the level of response to the HIV envelope protein. The c-mos peptide was consistently used in all the experiments as a control. Stock solutions of peptides were prepared in phosphate buffered saline (PBS) (pH 7.0) and filter sterilized.

4. T-cell Proliferation Assay

Heparinized blood was collected by venipuncture from both control and HIV-infected chimpanzees and human volunteers. HIV-positivity of samples was confirmed either by the standard serum p24-antigen capture assay, western blotting, or PCR analysis. Peripheral blood mononuclear cells (PBMCs) were isolated by centrifilgation on a Ficoll-Hypaque density gradient (Histopaque-1073; Sigma Chemical Co., St. Louis, Mo.). The proliferative responses of PBMCs from different samples was determined by the standard [$^3$H]thymidine incorporation assay as described earlier (Nehete, 1996; Nehete, 1995), against different concentrations of phytohemagglutinin (PHA), control peptide, or the conserved envelope peptides. Each sample was seeded in triplicate wells of 96-well U-bottom microtiter plates. The proliferative responses in case of chimpanzees were from experiments performed using samples collected at three different time points. Data from humans also includes analysis done at least at two different time points for majority of samples. The specific radioactivity of cells treated with various additions was calculated in each case by subtracting the counts per minute (cpm) values obtained with cells cultured in medium alone. The significance of T-cell proliferative responses (in terms of stimulation index [SI]) to the envelope peptides was calculated as the fold-increase of [$^3$H]thymidine incorporation by cells exposed to envelope peptide over those cells to which no peptide was added. An SI value of >3.0 was considered significant, while an SI value <3.0 but >2.0, to at least one concentration of the peptide was considered to be a positive response. Similar criterion were reported by others for describing significant proliferative responses (Pontessili, 1995; Schrier, 1989). In all the experiments, data from triplicate samples were comparable with a standard error of <10%.

5. Analysis of Anti-peptide Antibodies

Serum samples collected from both control and HIV-infected chimpanzees and human volunteers were analyzed as described earlier (Nehete, 1993, Sastry, 1991) by ELISA for antibodies against each of the five envelope-derived peptides, and a control peptide used in the study. Briefly, peptides diluted in 0.05 M bicarbonate buffer (pH 9.6) were coated onto 96-well microtest-II flexible plates (Falcon, Los Angeles, Calif.) at 5 μg/well by incubating for 20 hours at 37° C. Subsequently, the plates were incubated with blocking solution (5% w/v non-fat dry milk) and washed twice with phosphate-buffered saline containing 0.5% Tween 20. Serial two-fold dilutions (1:20 to 1:2560) of serum samples (in 0.01 M sodium phosphate buffer, pH 7.4, containing 0.075 M NaCl, 2.5% non-fat dry milk, and 0.5% Tween 20) were assayed using horseradish peroxidase-conjugated second antibody. Unless otherwise mentioned, an antibody titer of 1:100 or higher against the peptide was considered a positive response.

6. Statistical Analysis

Data showing SI values, representing HIV-peptide-specific proliferation responses in both the HIV-positive chimpanzees and human volunteers, were analyzed using a 2 (×6) mixed factors analysis of variance (ANOVA). Since the overall ANOVA revealed that there were significant differences in proliferative responses of HIV-infected chimpanzees and HIV+ individuals across the different peptides, several planned comparisons were performed. These included: (a) all five envelope peptides versus the control peptide, (b) peptide 104 versus the control peptide, and (c) peptide 104 versus other conserved envelope peptides. Similar analyses were performed with values for the anti-peptide antibody titers.

Example 6

Synthetic Peptide From the First Conserved Region in the Envelope Protein gp160 is a T-cell Epitope in HIV-infected Chimpanzees and Humans 1. Proliferative Responses to Peptide 104 in HIV-infected Chimpanzees Freshly isolated PBMCs from two control uninfected chimpanzees and from nine HIV-infected chimpanzees were tested for proliferation against PHA (a non-specific T-cell mitogen), control peptide, and peptide 104 from the amino-terminal conserved region of gp120.

Standard [$^3$H]thymidine incorporation assays reveal that seven of the nine HIV-infected chimpanzees exhibited positive proliferative responses (SI values ranging between 2 and 11) against peptide 104. Proliferative responses to peptide 104 in HIV-infected chimpanzees were significantly higher than responses to the control peptide [$F(1,8)=6.59$, $p<0.05$]. In three chimpanzees, the SI values were above 5.1, indicating significant levels of proliferative responses to peptide 104. Chimpanzee 175 showed a higher background level of proliferation with the control peptide (SI 2.7); however, proliferation with peptide 104 was considerably above this level, indicating a positive response. The two control chimpanzees showed no positive proliferative responses with any of the HIV peptides or the control peptide tested, but significant proliferation was observed in both the chimpanzees with PHA (cpm and SI values ranged between 15832–20504 and 34–49.5, respectively). The cpm values for the medium control in individual chimpanzees ranged between 147±15 and 2819±298. Similarly, all nine HIV-infected chimpanzees showed high levels of proliferation with PHA.

2. Proliferative Responses to Peptide 104 in HIV+ Humans

Results from proliferation assays indicated that eight of the 17 HIV+ individuals tested showed positive proliferative responses with peptide 104; in six of these eight individuals, the SI values were above 4.1. On the other hand, none of the HIV+ individuals tested exhibited proliferative responses specific to the control peptide. The cpm values for the medium control in human subjects were between 123±11 and 1529±163.

Overall, in the 17 HIV+ individuals, the proliferative responses to peptide 104 were significantly higher than those to control peptide [F(1,16)=12.30, p<0.01]. The PBMCs isolated from control HIV-seronegative individuals exhibited no specific proliferative responses to any peptide tested. However, proliferative responses directed against the non-specific mitogen PHA were observed in all the HIV+ individuals (cpm and SI values ranged from 108361–127640 and 20.3–23.3, respectively). The corresponding range of values for the normal subjects were 32137 to 99557 cpm, and SI were 131–183.

3. Proliferative Responses Against Four Different Conserved Peptides From the HIV Envelope Protein gp160 in HIV-infected Chimpanzees and Humans Also investigated were proliferative responses of PBMCs from the chimpanzees to synthetic peptides 113, 120, 121, and 122, which are derived from conserved regions in the HIV envelope protein. While no proliferation was observed with PBMCs from the control normal chimpanzees with any of the peptides, five of the nine HIV-infected chimpanzees showed positive response with at least three of the four conserved- peptides. Positive proliferative responses (SI>2.0) were observed against peptides 113 and 121 in five animals each, while chimpanzees 69, 80, and 100 showed positive responses with all the four peptides tested. Among the four peptides, proliferative responses to peptide 120 were comparatively lower than that for the other three peptides even though the differences were not significant. Statistically, the combined responses to peptides 113, 120, 121, and 122 were significantly higher than those to the control c-mos peptide [F(1,8)=12.08, p<0.01]. Additionally, none of the chimpanzees showed positive proliferative responses to other control peptides.

PBMCs from the 17 HIV+ individuals also were tested for proliferative responses against the four conserved HIV peptides, 113, 120, 121, and 122. A maximum of seven individuals exhibited positive proliferative responses against peptide 122, while five individuals were positive for each of the other three peptides. Efficient proliferative responses (SI values >3.0) were observed for all four conserved peptides in patient RB. In all the 17 HIV+ individuals, the SI values for the four different conserved peptides were significantly higher than those for the control peptide [F(1,16)=9.98, p<0.01]. None of the patients showed positive proliferation with either the c-mos peptide, or any of the other control peptides tested. Also, PBMCs from none of the control normal subjects exhibited appreciable proliferation with any of the peptides tested. In the 17 HIV+ individuals, despite a wide range of CD4+ cell counts (146–656/mm3), significant differences in the levels of proliferation to the test peptides were not observed.

Statistical analysis of the SI values in the nine HIV-infected chimpanzees revealed that the overall proliferative responses to the five conserved HIV peptides (104, 113, 120, 121, and 122) combined were significantly higher than those responses to the control peptide, [F(1,8)=24.5, p<0.001]. However, a comparison of proliferative responses to the five individual peptides showed no significant differences [F(1, 8)=1.49, p>0.05]. Overall, in the nine HIV-infected chimpanzees the rank order of proliferative responses to the peptides was 104>121>113>122>120. In the case of HIV+ individuals, not only were the overall proliferative responses to the five conserved HIV envelope peptides significantly higher than those responses to the control peptide [F(1,16)= 13.72, p,<0.01], but also, the proliferative responses to peptide 104 were higher than those to the other four conserved peptides 113, 120, 121, and 122[F(1,16)=3.75, p<0.07].

4. Antibody Response to the Conserved Peptides in HIV-infected Chimpanzees and Humans In contrast to the proliferative responses, no antibody response directed against any of the conserved HIV peptides was observed in the HIV-infected chimpanzees (ELISA titers <1:20). Data in TABLE 6 below show the positive and negative results for both proliferation and antibody responses. Serum samples from the two control uninfected animals also showed no anti-peptide antibody responses.

TABLE 6

T and B cell responses of PBMCs from control and HIV-1 infected chimpanzees to various synthetic peptides from conserved regions in the HIV-1 envelope protein

| Chimpanzee | Immune response* | \multicolumn{6}{c}{Peptides} |
|---|---|---|---|---|---|---|---|
| | | 104 | 113 | 120 | 121 | 122 | Control** |
| Control Normal: | | | | | | | |
| 40 | T | – | – | – | – | – | – |
| | B | – | – | – | – | – | – |
| 73 | T | – | – | – | – | – | – |
| | B | – | – | – | – | – | – |
| HIV-infected: | | | | | | | |
| 62 | T | + | + | + | + | – | – |
| | B | – | – | – | – | – | – |
| 69 | T | + | + | + | + | + | – |
| | B | – | – | – | – | – | – |
| 80 | T | + | + | + | + | + | – |
| | B | – | – | – | – | – | – |
| 99 | T | + | – | – | – | – | – |
| | B | – | – | – | – | – | – |
| 100 | T | – | + | + | + | + | – |
| | B | – | – | – | – | – | – |
| 139 | T | + | – | – | – | – | – |
| | B | – | – | – | – | – | – |
| 175 | T | + | + | – | + | + | + |
| | B | – | – | – | – | – | – |
| 247 | T | – | – | – | – | – | – |
| | B | – | – | – | – | – | – |
| 310 | T | + | – | – | – | – | – |
| | B | – | – | – | – | – | – |

*T T-cell proliferative response: +, Positive (Stimulation Index [SI] > 2.0); –, Negative (SI < 2.0).
*B Anti-peptide antibody response: +, Positive (Titer > 1:100); –, Negative (Titer < 1:100).
**The control is a 15 amino acid peptide from the mouse c-mos protooncogene product.

Low level antibody responses directed against the conserved peptides were observed in some of the HIV-infected individuals (see TABLE 7 below). The end-point dilution analysis of serum samples by ELISA from two of the 17 subjects showed antibody titers of 1:160 and 1:320, respectively, against the control peptide. Therefore, the antibody titers for the conserved peptides were normalized against the highest value for the control peptide (1:320). Based on these calculations, positive antibody titers (<1:1280) were observed in three individuals for peptide 104, in two persons for peptide 120, and one person each for peptides 113 and 121. None of the HIV+ individuals showed positive antibody titers to peptide 122. Overall, there were only low levels of antibody (ELISA titers <1:1280) responses directed against the five conserved peptides in a total of six HIV+ individuals studied. Planned comparisons revealed that antibody titers also did not differ significantly for any of the five conserved HIV synthetic peptides versus control, peptide 104 versus control, and peptide 104 versus the other four conserved peptides [$F(1,16)=2.67$, $F(1,16)=2.40$, $F(1,16)=0.22$; all p values >0.05]. The control HIV-seronegative subjects showed no antibody response to any of the peptides tested. Synthetic peptides with overlapping amino acid sequences to peptides 104, 120, and 122 used in the present study have been reported in the literature to be immunogenic in certain animal models and also to react with antisera from HIV+ individuals (Clerget-Raslain, 1991; and reviewed in Bjorling, 1996).

TABLE 7

T and B cell responses of PBMCs from normal and HIV-positive individuals to various synthetic peptides from conserved regions in the HIV-1 envelope protein

| Patient | Immune response* | Peptides | | | | | Control |
|---|---|---|---|---|---|---|---|
| | | 104 | 113 | 120 | 121 | 122 | (c-mos) |
| CS | T | + | + | + | + | – | – |
| | B | + | + | – | – | – | – |
| BH | T | + | – | – | + | + | – |
| | B | – | – | – | – | – | – |
| MH | T | + | – | + | – | + | – |
| | B | – | – | – | + | – | – |
| RR | T | + | + | – | – | – | – |
| | B | – | – | – | – | – | – |
| ER | T | + | – | + | – | – | – |
| | B | – | – | + | – | – | – |
| MB | T | + | – | – | – | – | – |
| | B | + | – | – | – | – | – |
| RC | T | – | – | – | + | + | – |
| | B | – | – | – | – | – | – |
| JH | T | – | – | – | – | – | – |
| | B | – | – | – | – | – | – |
| RT | T | – | – | – | – | – | – |
| | B | + | – | – | – | – | – |
| RB | T | + | + | + | + | + | – |
| | B | – | – | – | – | – | – |
| WC | T | – | + | – | + | + | – |
| | B | – | – | – | – | – | – |
| DN | T | + | – | – | – | + | – |
| | B | – | – | – | – | – | – |
| ST | T | – | + | + | – | – | – |
| | B | – | – | – | – | – | – |
| JW | T | – | – | – | – | + | – |
| | B | – | – | + | – | – | – |
| MSm | T | – | – | – | – | – | – |
| | B | – | – | – | – | – | – |
| MSf | T | – | – | – | – | – | – |
| | B | – | – | – | – | – | – |
| BT | T | – | – | – | – | – | – |
| | B | – | – | – | – | – | – |
| Normal-1 | T | – | – | – | – | – | – |
| | B | – | – | – | – | – | – |
| Normal-2 | T | – | – | – | – | – | – |
| | B | – | – | – | – | – | – |

*T T-cell proliferative: +, Positive (Stimulation Index [SI] > 2.0); –, Negative (SI < 2.0).
*B Anti-peptide antibody: +, Positive (titer above control); –, Negative (titer below control).

Example 7

Vaccination of Monkeys With a Cocktail of Synthetic Peptides From the Envelope Protein gp160 Induces Proliferative and CTL Responses Because proliferative responses to several HIV-envelope-derived peptides were observed in several animal models including HIV-infected chimpanzees and HIV-infected humans, monkeys not yet infected with the virus were given a cocktail of env peptides to evaluate their T lymphocyte responses to the mixture.

Five monkeys were involved in this study; three received an HIV envelope peptide mixture vaccine (TABLE 8) while the other two served as controls. The vaccination protocol consisted of a primary immunization with the peptide mixture in complete Freund's adjuvant, followed by two booster doses of the peptide mixture in incomplete Freund's adjuvant at monthly intervals (by the subcutaneous route). The control monkeys were immunized with the adjuvant preparation without the peptide mixture. Subsequently, the vaccine monkeys received three weekly intravenous doses of autologous dendritic cells (DC) pulsed with the peptide mixture, while the control monkeys received only DC. All five monkeys were challenged with simian HIV (SHIV) 29 weeks post primary-immunization.

TABLE 8

Conserved HIV envelope peptides used in the vaccine study

| Peptide no. | Amino acid residues | Amino acid sequence |
|---|---|---|
| 61 | 586–597 | YLRDQQLLGIWG (SEQ ID NO:33) |
| 63 | 519–543 | FLGFLGAAGSTMGAASLTLTVQARQ (SEQ ID NO:20) |
| 104 | 45–55 | VYYGVPVWKEA (SEQ ID NO:1) |
| 111 | 118–130 | LWDQSLKPCVKLT (SEQ ID NO:4) |
| 113 | 204–216 | SVITQACSKVSFE (SEQ ID NO:8) |
| 116 | 540–552 | GTGPCTNVSTVQC (SEQ ID NO:16) |

The monkeys were monitored at regular intervals for various immune responses specific to the peptides, and the HIV envelope protein. The amino acid sequences of various peptides included in the vaccine preparation are shown in TABLE 8. Data presented in FIG. 3 show peptide and HIV-specific proliferative responses in the peripheral blood samples collected over a period of 32 weeks. Two monkeys vaccinated with the peptide mixture, J13 and L889, showed significant proliferative responses throughout the 32-week period, while the third vaccine monkey (L993) and the two control monkeys (L913 and L933) did not show consistent responses.

Importantly, two of the vaccinated monkeys tested showed HIV-envelope-specific CTL responses while the control monkeys did not (FIG. 6). The natural killer cell (NK) activity in the five monkeys was not significantly different (FIG. 4). Prior to challenging the monkeys with SHIV, the susceptibility of PBMC from each of the monkeys to SHIV infection was tested in vitro. HIV infection was monitored after an 18-hour period by nested PCR analysis; compared to the control monkeys the PBMC from vaccinated monkeys are less susceptible to SHIV infection. However, PBMC from both vaccine and control monkeys prior to peptide vaccination were equally susceptible to SHIV infection in vitro.

Figures 1, 7A:
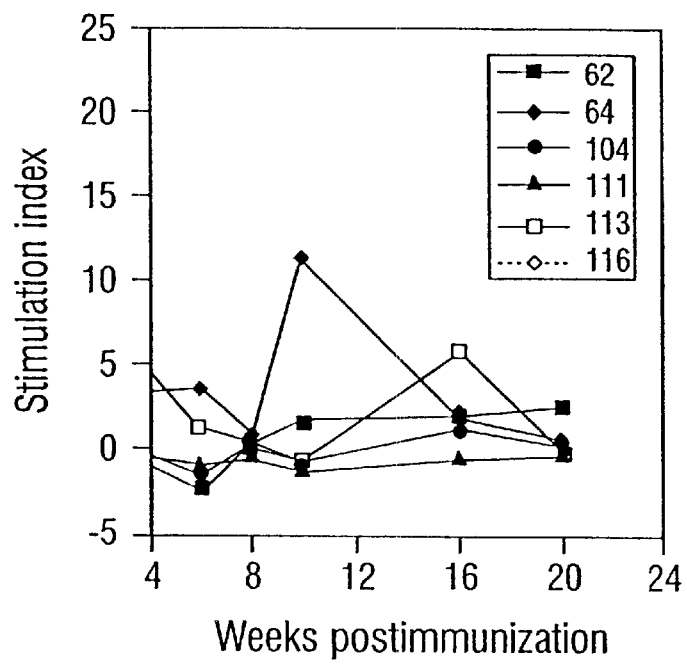
FIGS. 7A–B. A. Peptide-specific proliferative responses prior to DC infusions in vaccinated and control monkeys. Equal amounts (100 μg) of each of the six conserved HIV envelope peptides were emulsified in complete Freunds adjuvant (CFA) and injected subcutaneously into three monkeys while two controls received only CFA. At 4 and 8 weeks, booster doses of peptide mixture in incomplete Freunds adjuvant (IFA) were given (the controls received only IFA). Proliferative responses specific to the six individual peptides were estimated by the standard [$^3$H] thymidine incorporation assays. Peptide-specific responses (above the medium background and a control peptide) were observed only in the vaccinated monkeys but not in the controls. In majority of cases, by week 20 the responses decreased to background levels. This is when the peptide-pulsed DC infusions were given to the vaccinated monkeys to boost the responses, while the control monkeys received un-pulsed DC. B. Peptide-specific proliferative responses after DC infusion in vaccinated and control monkeys. Autologous monocyte-derived dendritic cells (DC) were prepared from PBMC and pulsed with the mixture of six synthetic peptides for 24 hours before intravenous infusion into the monkeys that were vaccinated earlier with the same peptide mixture in Freund's adjuvant. A total of three infusions were given at weeks 22, 24, and 25. The control monkeys received autologous DC without peptide pulsing. In the vaccinated monkeys, the peptides with an increase in proliferative response (above the background and a control peptide) subsequent to DC infusion were marked with an asterisk (*).
Figures 2, 7A:
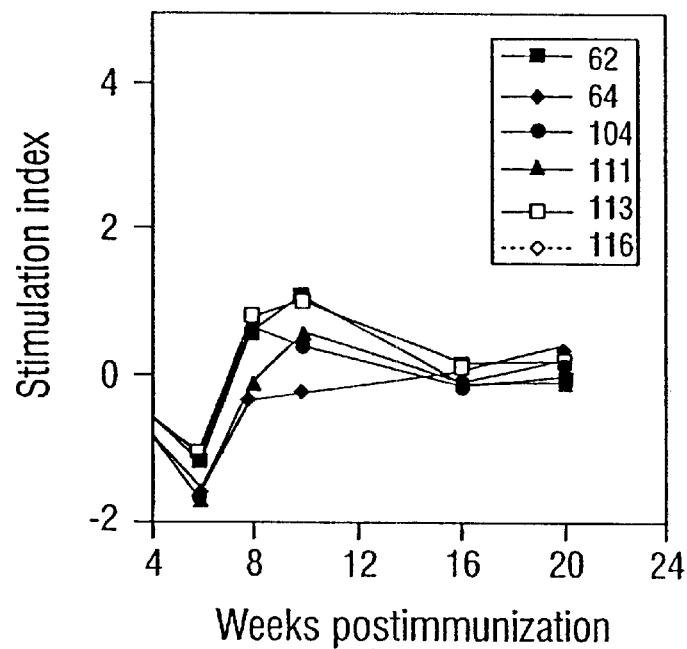
Figures 3, 7A:
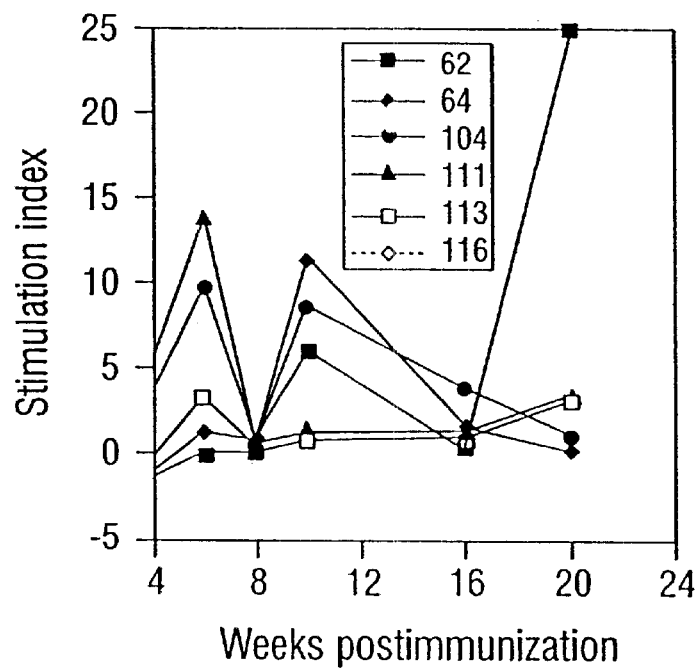
Figures 4, 7A:
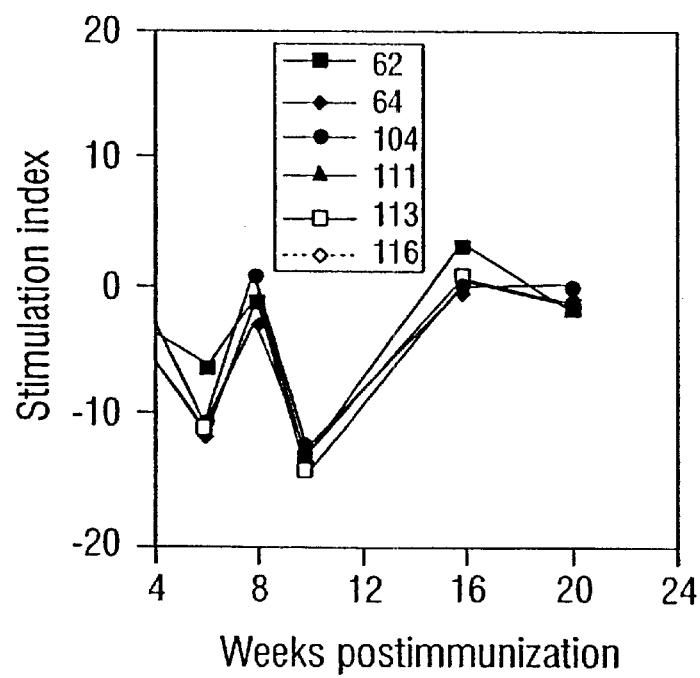
Figures 5, 7A:
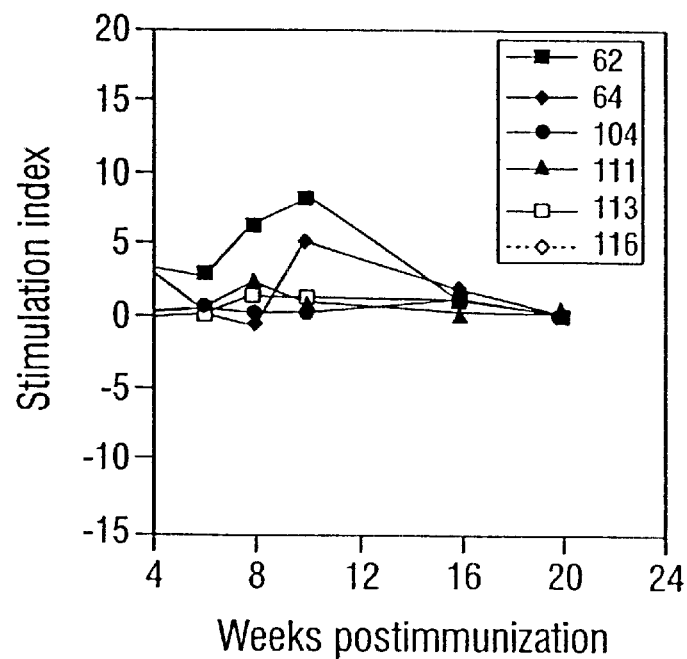

Most significantly, analyses of CD4+ and CD8+ cells of the five monkeys showed that the two control monkeys exhibited drastic drops in CD4+ cell numbers by two weeks post-challenge (FIG. 5). Published reports indicate that the primary, and also the most significant, indication of infection by SHIV in rhesus monkeys is the subtotal loss of CD4+ cells. The CD4+ cell loss is known to be followed by other typical signs of AIDS such as opportunistic infections and weight loss, which are similar to the typical symptoms of HIV-induced AIDS in humans. Interestingly, the precipitous drop in CD4+ cell numbers in the control monkeys paralleled high virus load in plasma as well as high in virus infected cells in circulation (TABLE 9).

TABLE 9

| | Post-challenge analyses | | | |
|---|---|---|---|---|
| Measurement | Monkey # | Week 1 | Week 2 | Week 3 |
| CD4+ cells | J13 | 2259 | 1194 | 1831 |
| (#/μl) | L889 | 2282 | 1072 | 825 |
| | L993 | 1257 | 1839 | 423 |
| | L913 | 1290 | 121 | 126 |
| | L933 | 4055 | 2339 | 373 |
| Infected cells | J13 | 100 | 100 | 100 |
| (#/10⁶ PBMC) | L889 | 100,000 | 100,000 | 100,000 |
| | L993 | 10,000 | 10,000 | 10,000 |
| | L913 | 100,000 | 100,000 | 100,000 |
| | L933 | 100,000 | 100,000 | 100,000 |
| Plasma virus titer* | J13 | ND | ND | 1:25 |
| | L889 | ND | ND | 1:5 |
| | L993 | ND | ND | 1:5 |
| | L913 | ND | ND | 1:625 |
| | L933 | ND | ND | 1:625 |

*The last plasma dilution at which infectious virus was observed (measured as cytopathic effects (CPE) in C1866 cells).
ND = not determined Ongoing experiments following the vaccination of the monkeys with the peptide cocktail or with a control indicated significant CTL and proliferative responses specific to the HIV envelope in the peptide-vaccinated monkeys but not in the controls (FIG. 6).

Figures 1, 7B:
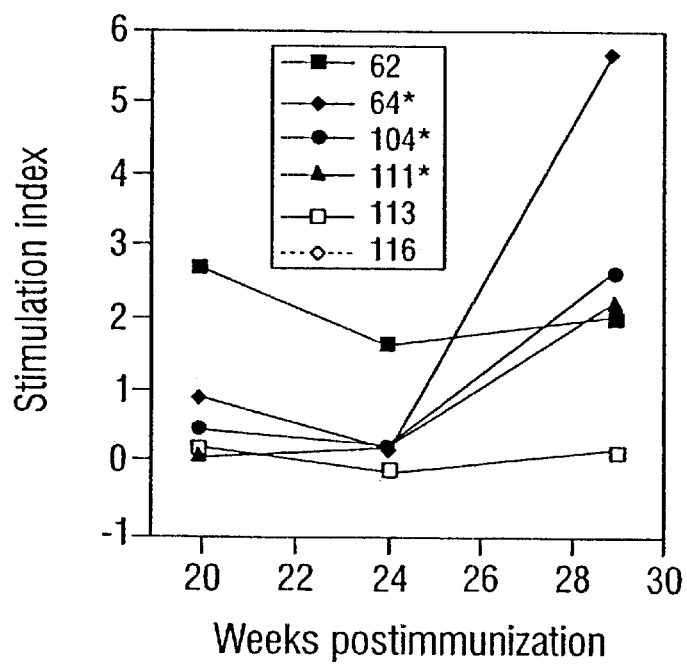
Figures 2, 7B:
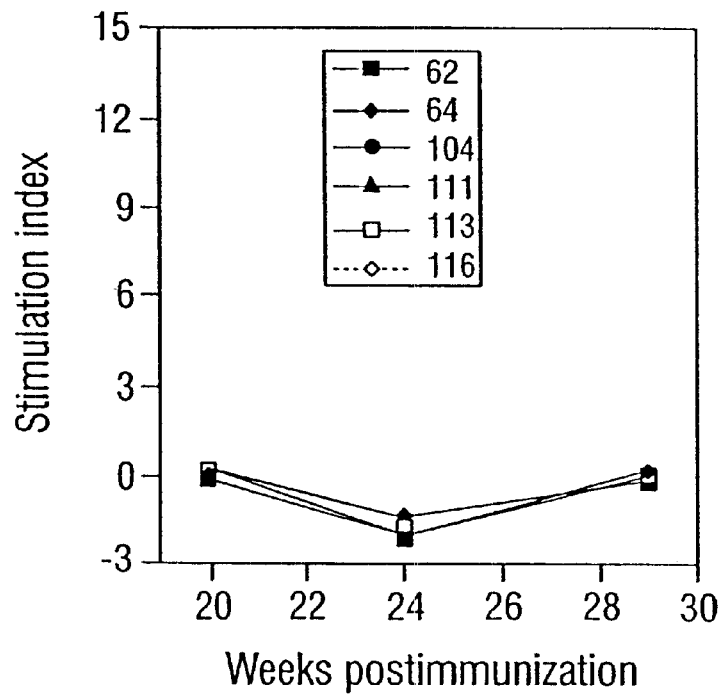
Figures 3, 7B:
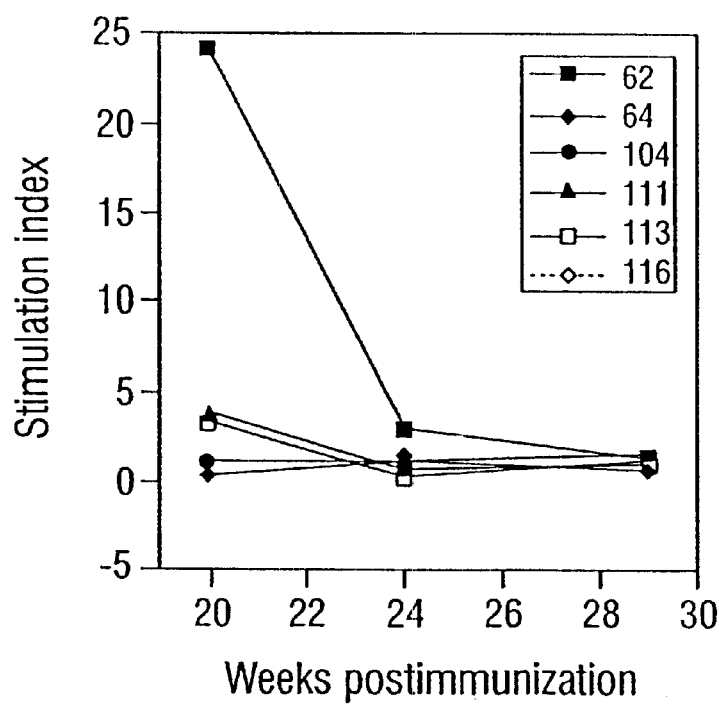
Figures 4, 7B:
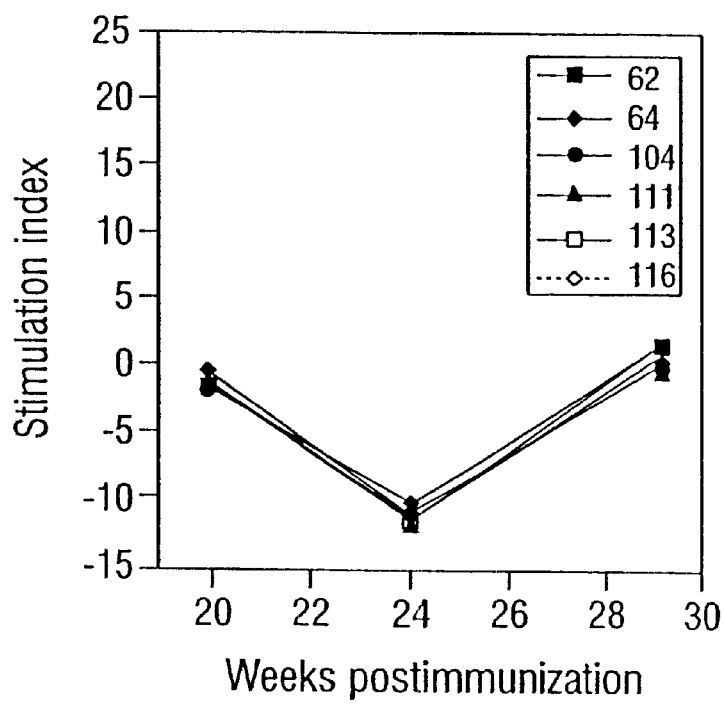
Figures 5, 7B:
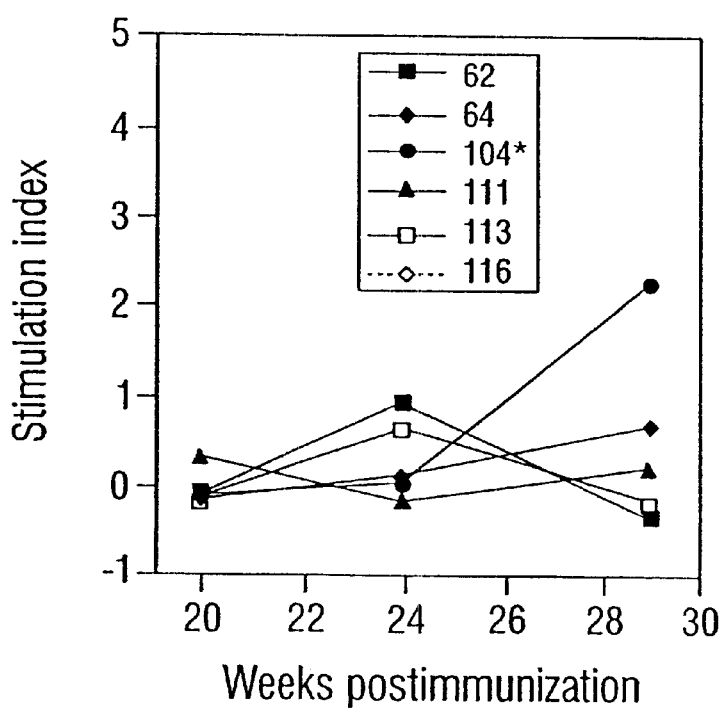
Figure 8A:
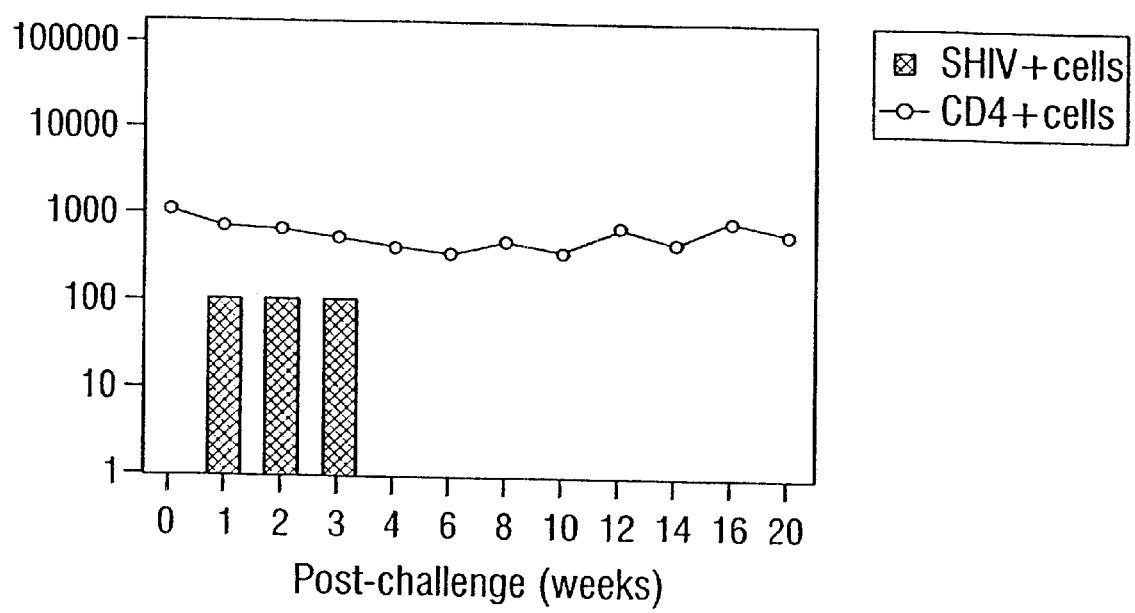
FIG. 8. Post-challenge analysis of blood samples from control and vaccinated monkeys. Post-challenge analysis of blood samples showing efficient control of SHIV infection in the vaccinated monkeys compared to the control animals. Blood samples were collected from the monkeys at different time intervals after challenge with SHIV-ku2, and analyzed for total CD4+ cells by flow cytometry and shown as absolute numbers (CD4+ cells). A series of 10-fold serial dilutions of PBMC isolated from the blood samples were co-cultured with $10^6$ C8166 indicator cells in 24-well tissue culture plates, and the highest dilution of PBMC showing a visible cytopathic effect (CPE) was used to calculate the number of SHIV-infected cells (SHIV+ cells) per $10^6$ PBMC.
Figure 8B:
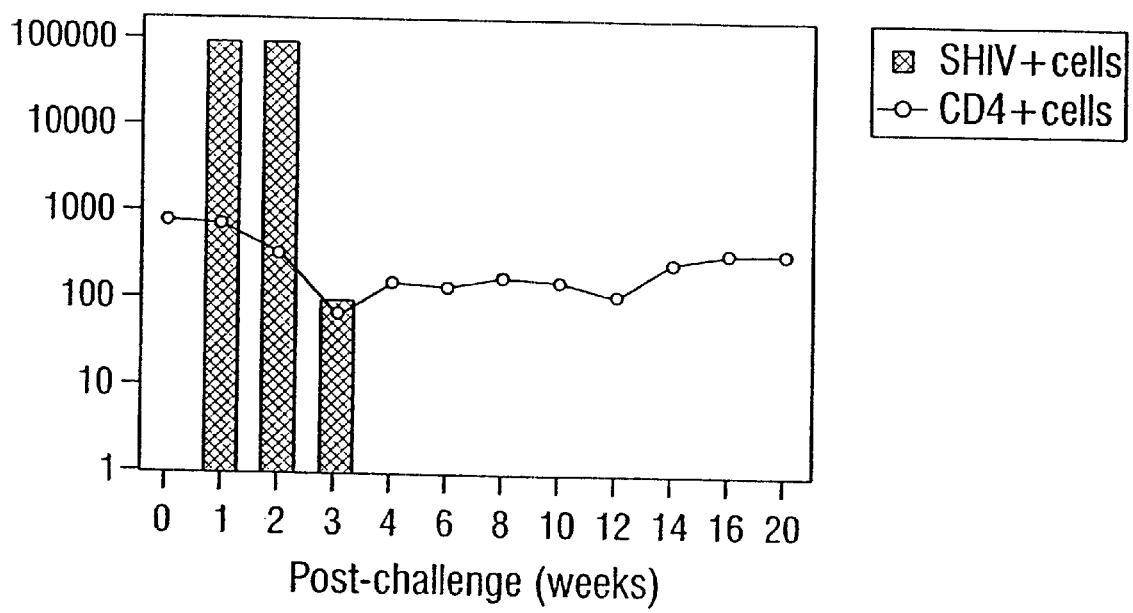
Figure 8C:
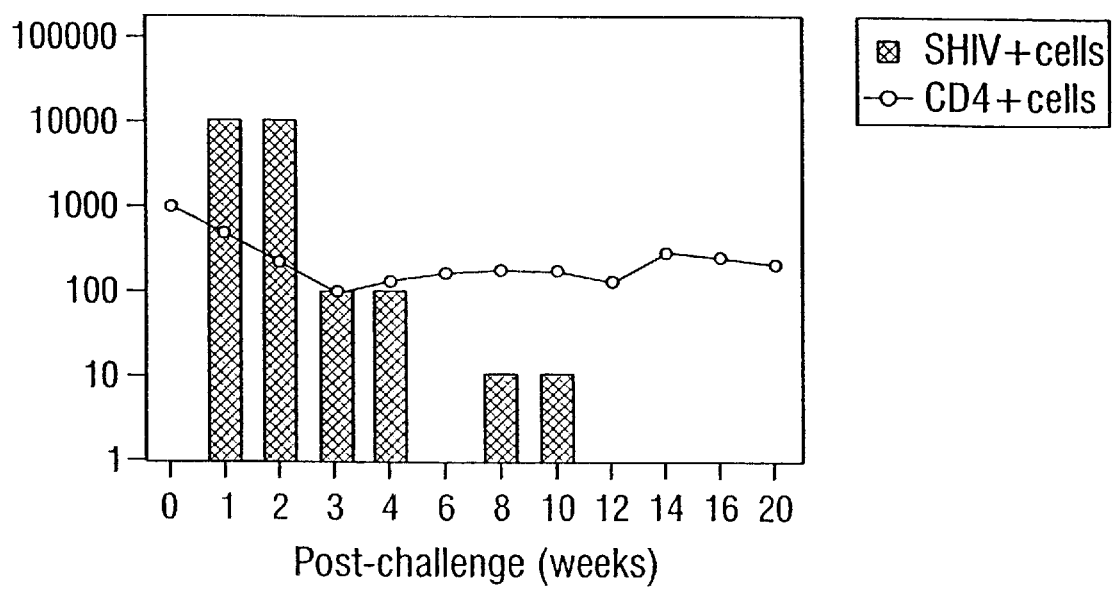
Figure 8D:
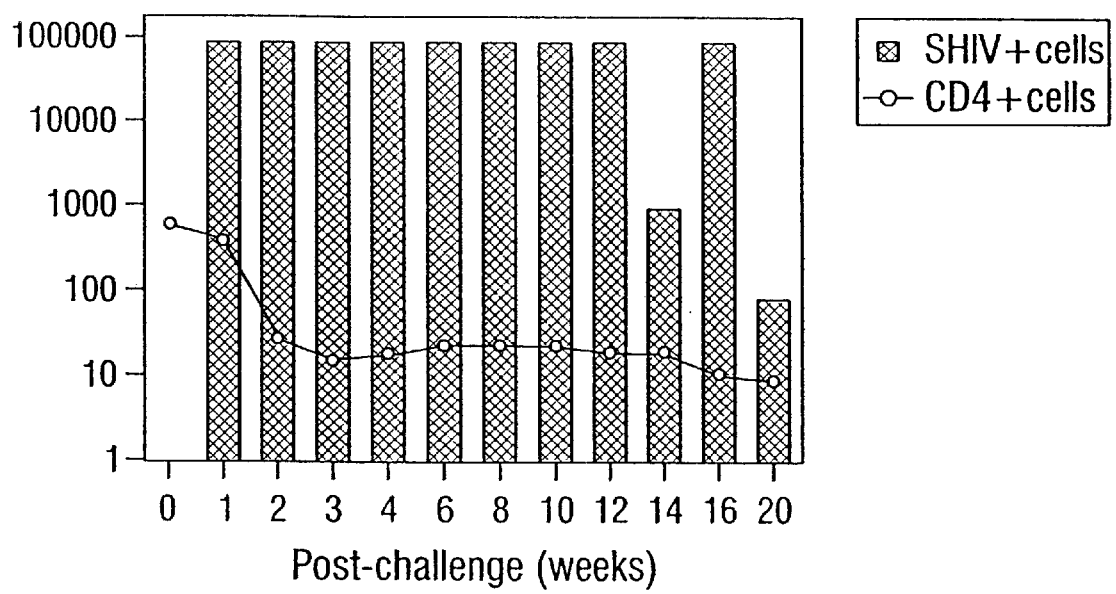
Figure 8E:
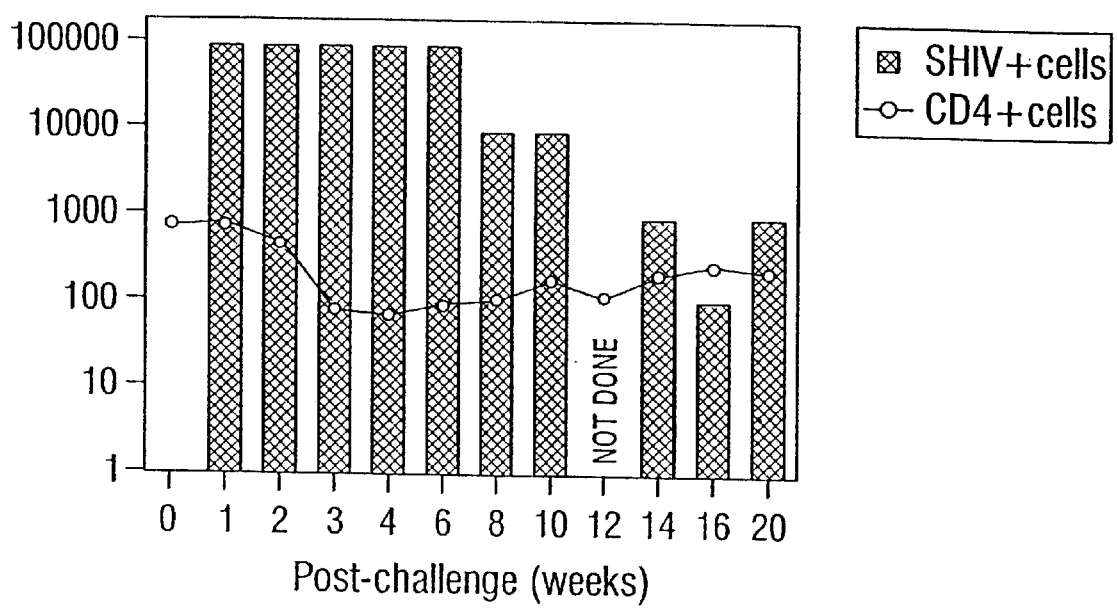

The DC infusions also significantly increased the cellular immune responses in the vaccinated monkeys, but had no effect in the control monkeys (FIGS. 7A and 7B). Importantly, upon challenge with the pathogenic SHIV$_{KU-2}$, even though all the five monkeys were infected, the virus$^+$ cells in circulation quickly dropped to low-to-undetectable levels in the vaccinated animals while that in the controls remained high (FIG. 8).

Figure 9:
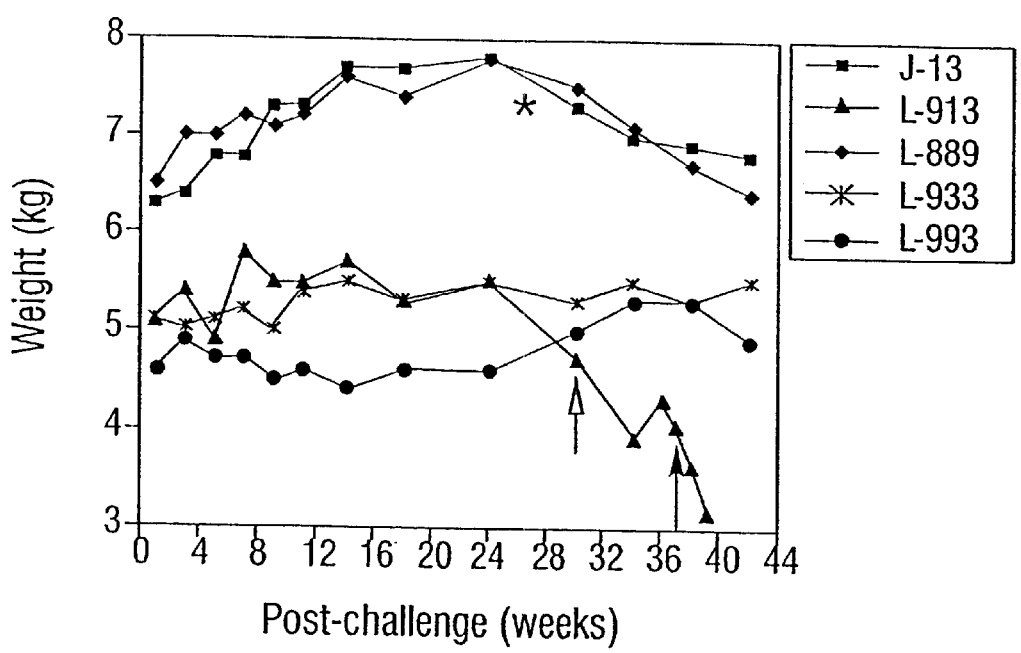
FIG. 9. Changes in total body weights in control and peptide-vaccinated monkeys after SHIV-ku2 challenge. Body weights of the monkeys were monitored continuously from pre-immunization to post-challenge. The two vaccinated monkeys J13 and L889 steadily gained weight and at 24 weeks post-challenge, they were started on a diet feed to maintain a reasonable body weight. The other vaccinated monkey L993 and one control monkey L933 did not show appreciable differences in weight. However, one control monkey L913 had started to lose weight at 24 weeks, and despite supplementation with an enriched diet, continued to show weight loss, which is a sign of wasting syndrome, often associated with AIDS. (The open and filled arrows at weeks 30 and 37, respectively, represent start and stop dates for a food supplement to the control monkey L-913.) This monkey was euthanized at 39 weeks. *Monkeys J-13 and L-889 were put on a diet-feed starting week 24 to prevent obesity.
Figure 10A:
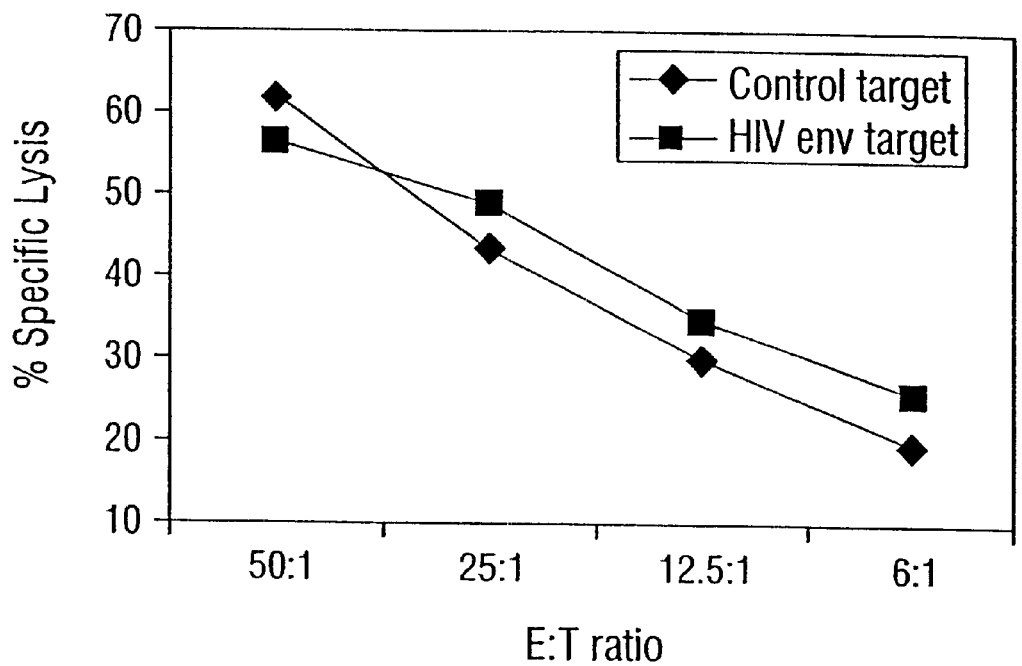
FIGS. 10A–D. HIV env-specific CTL activity against different HLA targets using PBMC from patient RLF. A. HIV env-specific CTL activity against HLA-A2 targets. B. HIV env-specific CTL activity against HLA-B2705 targets. C. HIV env-specific CTL activity against HLA-Cw7 targets. D. HIV env-specific CTL activity against HLA-Cw7 targets.
Figure 10B:
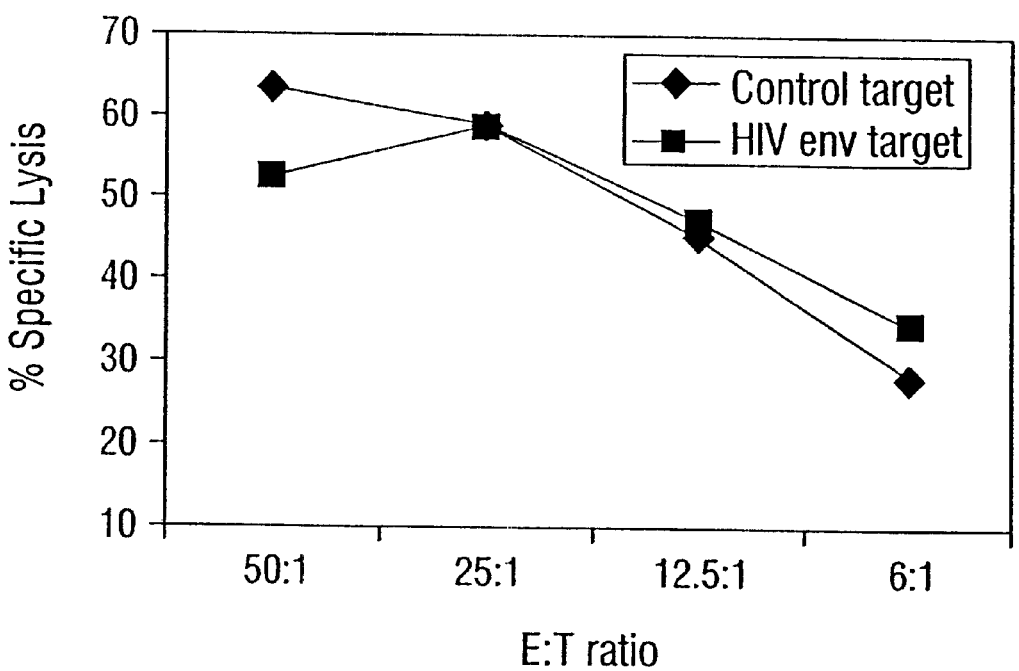
Figure 10C:
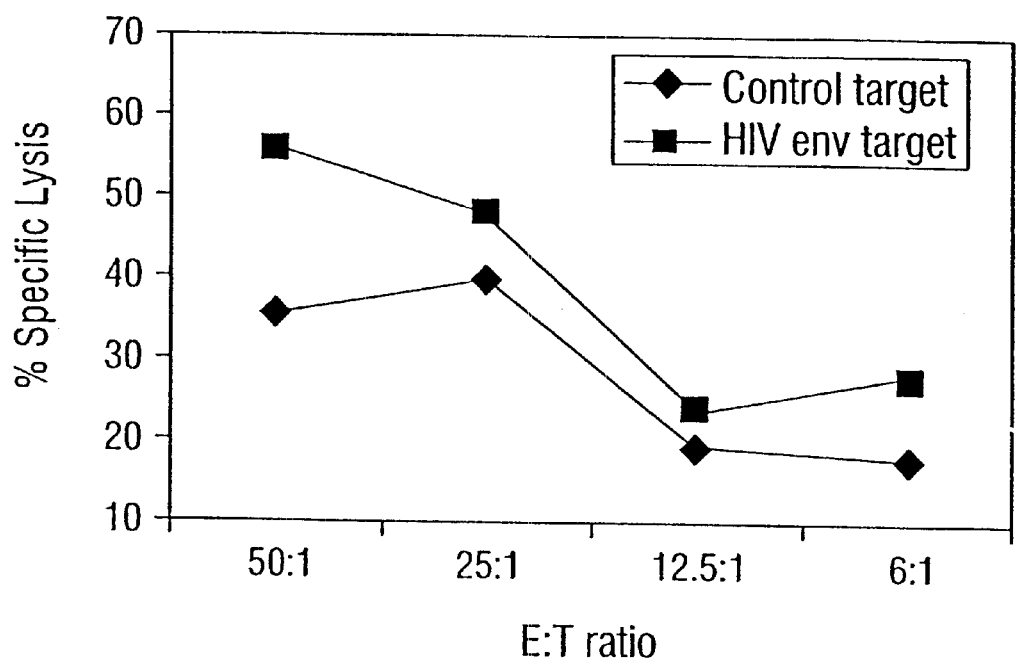
Figure 10D:
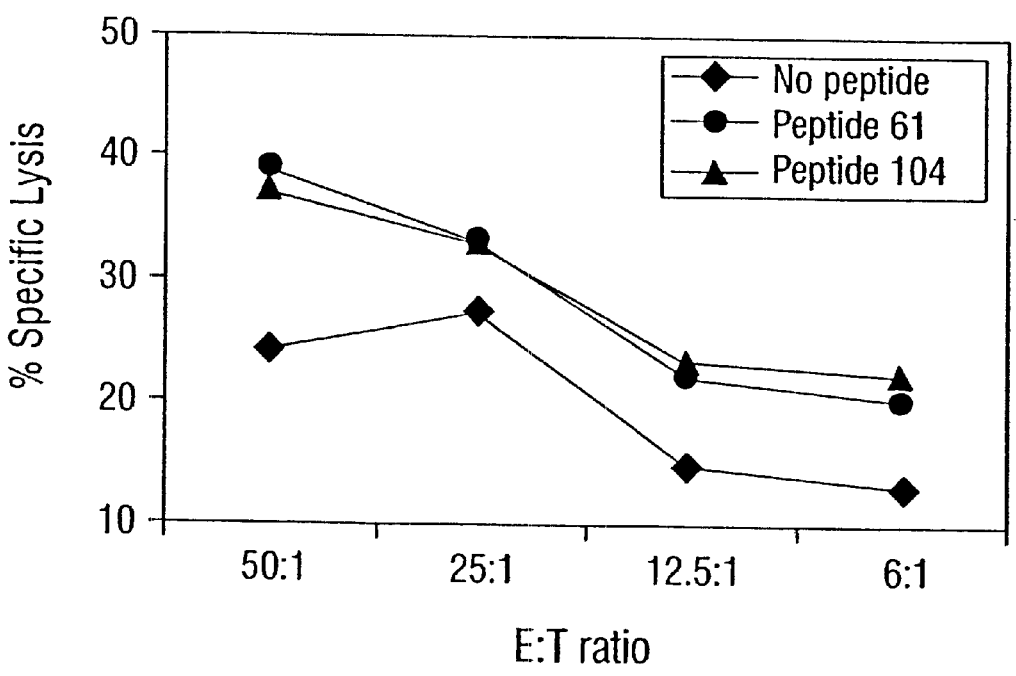
Figure 11A:
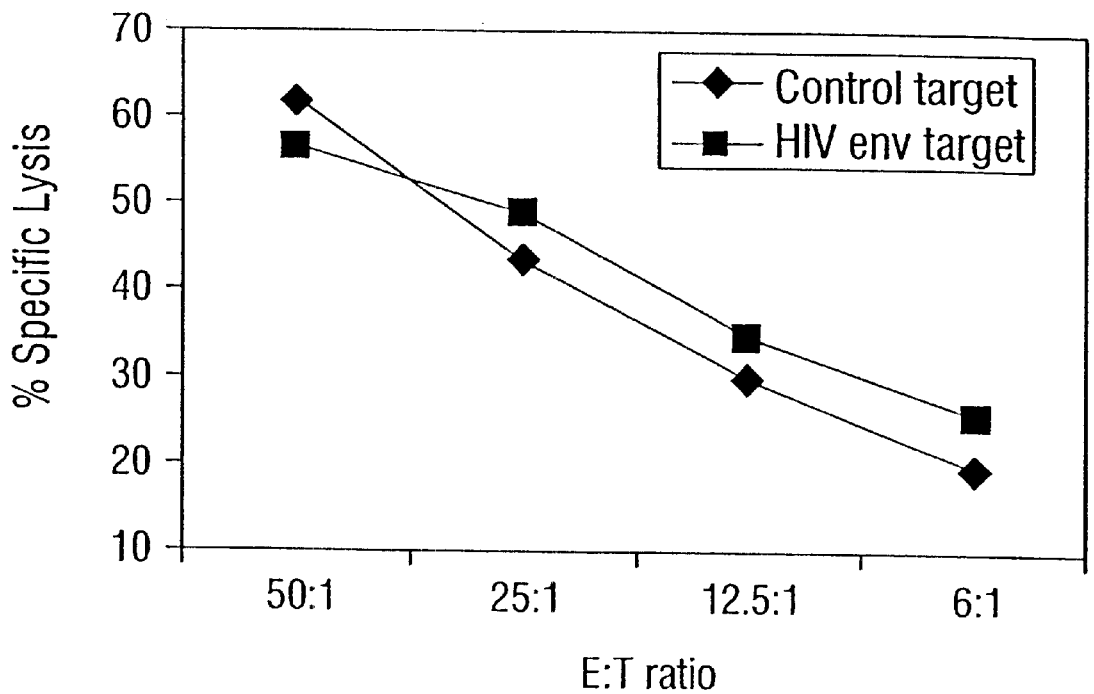
FIGS. 11A–D. HIV env-specific CTL activity against different HLA targets using PBMC from patient DH. A. HIV env-specific CTL activity against HLA-A2 targets. B. HIV env-specific CTL activity against HLA-B2705 targets. C. HIV env-specific CTL activity against HLA-Cw7 targets. D. HIV env peptide-specific CTL activity against HLA-Cw7 targets.
Figure 11B:
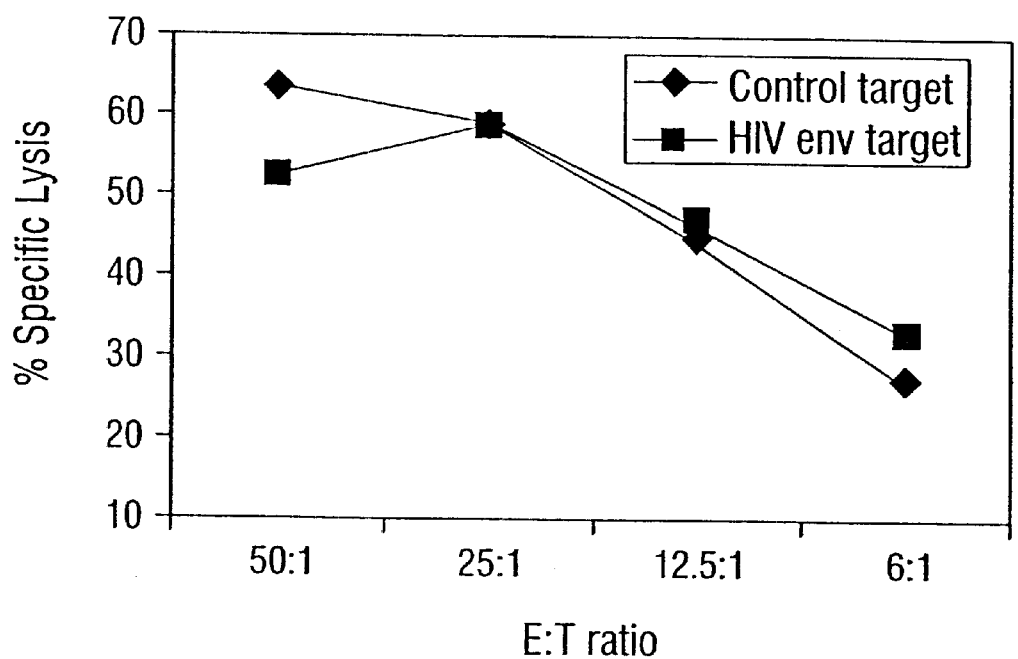
Figure 11C:
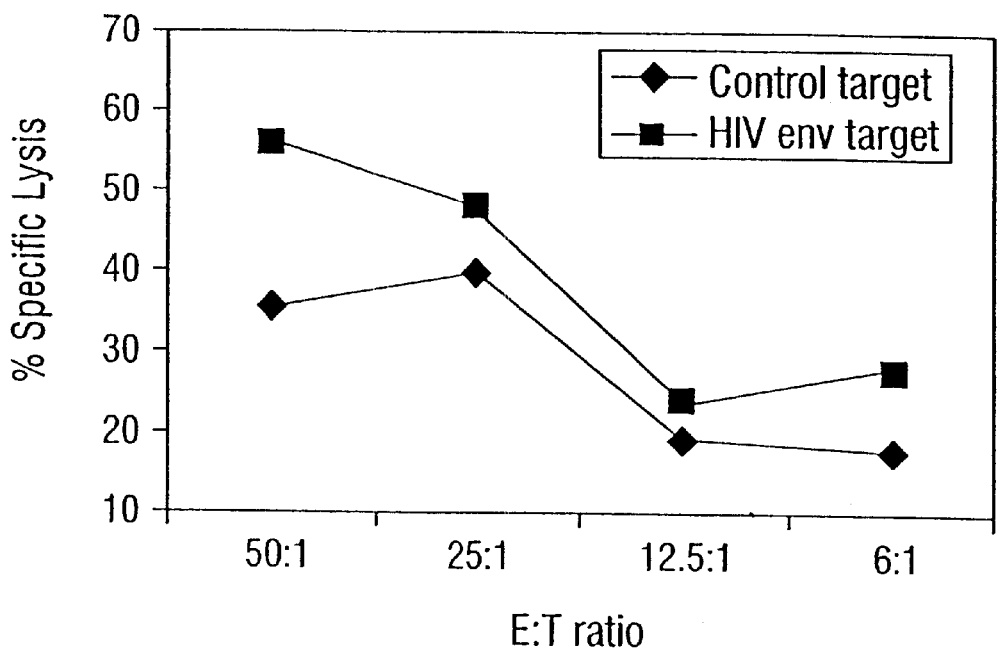
Figure 11D:
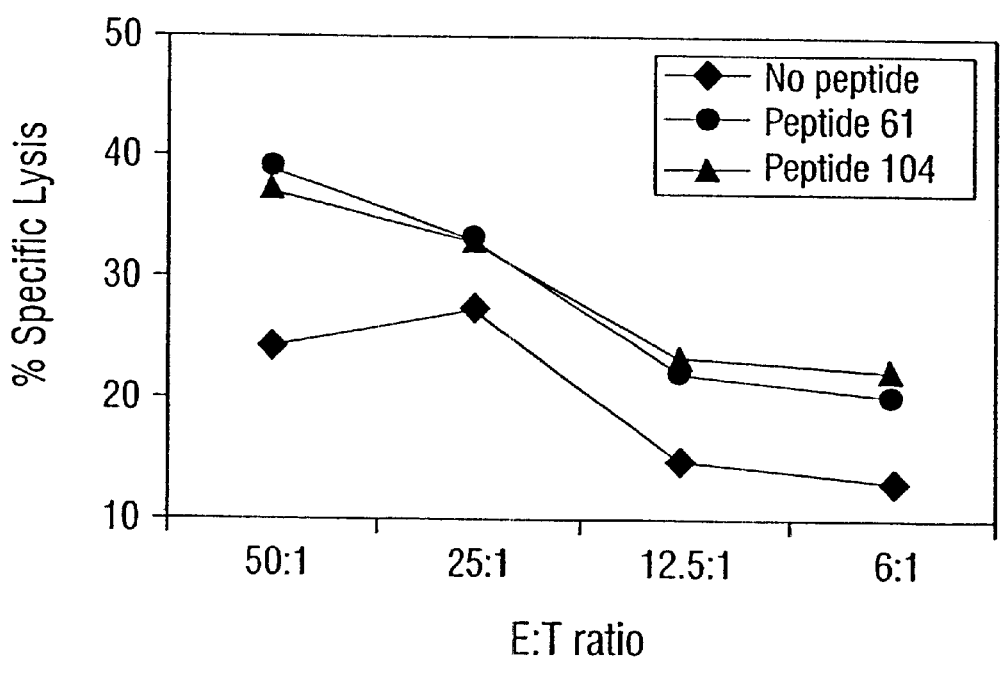

Also, in one control monkey the number of CD4$^+$ cells dropped to 40 within two weeks and further decreased to 6 by 24 weeks, which was accompanied by a significant weight loss indicating wasting, a typical AIDS-associated pathology. By week 39, this monkey lost a significant amount of weight (FIG. 9), had no circulating CD4$^+$ cells, and therefore was euthanized. At necropsy, histological examination revealed emaciation, muscle atrophy, and hemorrhage in stomach. Microscopically, severe lymphoid depletion was evident in several lymph nodes, and also there were lesions in multiple areas of the brain indicative of encephalitis, and intra-nuclear viral inclusions suggestive of CMV infection in the mid-brain area. These are AIDS-related features typical for SHIV infection in macaques. In the other control monkey, despite lack of any obvious symptoms of AIDS, the number of virus$^+$ cell was consistently higher than in the vaccinated animals.

The results obtained thus far strongly indicate the effectiveness of the vaccine based on the CTL epitopes restricted by HLA-Cw7 in the SHIV-rhesus model. However, it has been reported that the C locus of the MHC antigens is not present in rhesus monkeys (Boyson et al., 1996). It is therefore conceivable that the observed protective efficacy of the conserved HIV envelope CTL epitope peptides in the SHIV-rhesus model are due to immune responses specific to MHC alleles that are either closely or distantly related to HLA-Cw7.

Example 8

HLA-Cw7-restriction of CTL Responses in Human LTNPs

Further studies were conducted to confirm the HLA-Cw7-restriction of HIV envelope-specific CTL responses in HIV-infected long-term nonprogressors (LTNPs). Specifically, for these studies a mutant human B-cell line 721.221 that is deficient in HLA Class I expression was used. These 721.221 cells were transfected with and expressed a single HLA allele, and then they were used as target cells to assay the CTL effector function of PBMC from two long-term nonprogressors (RLF and DH). The effector cells were prepared by culturing PBMC from the patients for two weeks in the presence of autologous antigen presenting cells expressing HIV envelope. CTL activity against HIV envelope was determined in a typical chromium release assay. The results are presented in FIG. 10 and FIG. 11. FIG. 10 shows CTL activity with PBMC from patient RLF against target cells expressing HIV envelope protein in the context of Cw7, but not HLA A2 or B2705 (compare data in panels A and B with that in C). Additionally, the data in panel D shows the specificity of the CW7-restricted CTL activity against two conserved HIV envelope peptides. Similar data was obtained with cells from patient DH (FIG. 11) indicating that the HIV envelope-specific CTL activity is restricted by HLA Cw7 and that three conserved HIV envelope peptides serve as Cw7-restricted CTL epitopes in this patient.

These results confirm our earlier report that the HIV-infected long-term nonprogressors exhibit HLA-Cw7-restricted CTL activity, and further identify the conserved envelope peptides as CTL epitopes in two additional individuals that were not analyzed for epitope-specificity before. These results also provide further support to the contention that the HLA-Cw7-restricted CTL responses in the LTNPs, in particular those directed against the conserved HIV envelope peptides identified in these studies, constitute an important aspect of protective immunity against HIV.

Example 9

Minigene Cocktail DNA Vaccine for HIV

In this case, the P18 peptide sequence was cloned as shown below in FIG. 12A. Single intramuscular immunization with 10 μg of this plasmid into BALB/c mice mediated robust bulk CTL activity from mouse splenocytes 60 days later (FIG. 12B). The mini-gene construct mediated CTL responses comparable to those generated by a vector with ubiquitin fused to a region of HTLV IIIb gp120 containing the same P18 epitope (UB#23).

Given the success of this approach, different HIV epitopes were cloned into a mini-gene expression plasmid by PCR cloning in a manner analogous to that for the P18 epitope (FIGS. 13A–F). Plasmid constructs were designed to encode conserved amino acid sequences corresponding to peptide numbers 61, 63, 104, 111, and 113 (see Table 7, though in some cases sequences coding for additional amino acids were included).

Figure 12A:
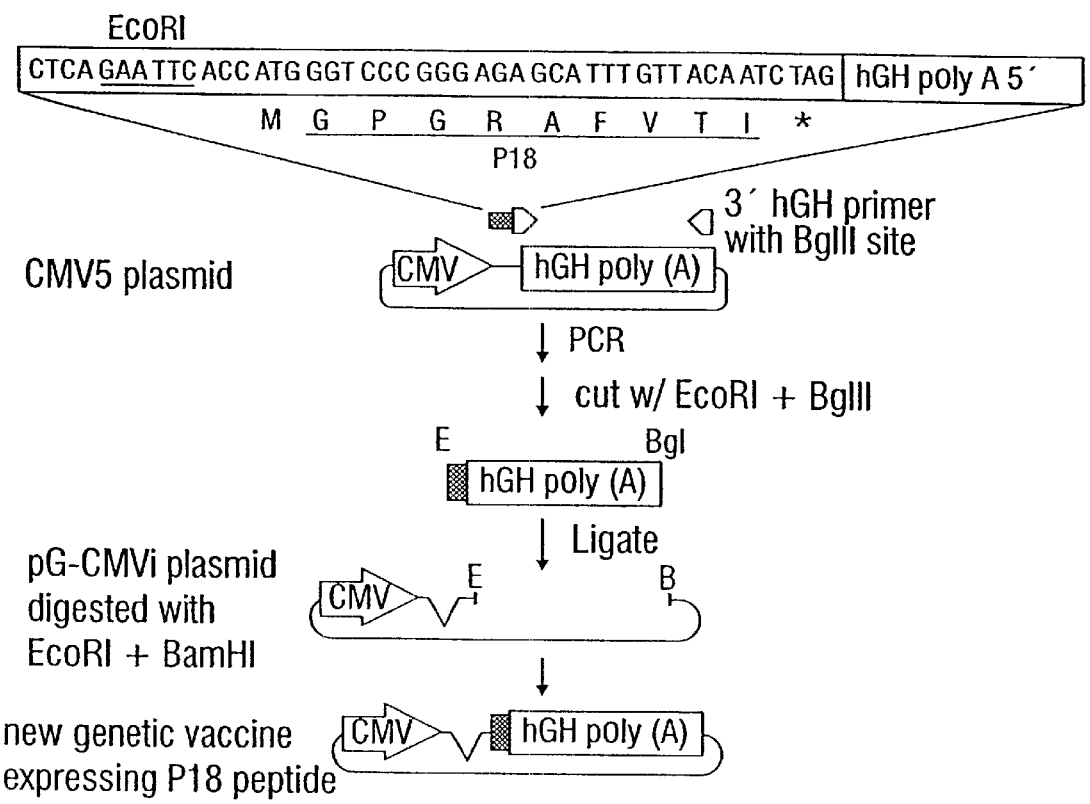
FIGS. 12A–B. Expression vector encoding HIV polypeptide and peptide sequences. A. Mini-gene construct showing the insert representing the sequence of P18, the HIV CTL epitope. B. P18-specific CTLs after single immunization in BALB/c mice with an epitope-expressing genetic vaccine. Mice were immunized by i.m. injection with 10 μg of each plasmid. 60 days later, splenocytes were recovered and assayed for P18-specific CTL responses on P18 peptide-loaded P815 target cells after stimulation in vitro. CMVi-P18 is a genetic vaccine expressing the P18 peptide with an additional start methionine. CMVi-UB#23 is a ubiquitin-fusion protein genetic vaccine expressing a region of gp120 containing the P18 epitope. CMVi-UB#2 is a negative control plasmid expressing a region of the gag gene also fused to ubiquitin.
Figure 12B:
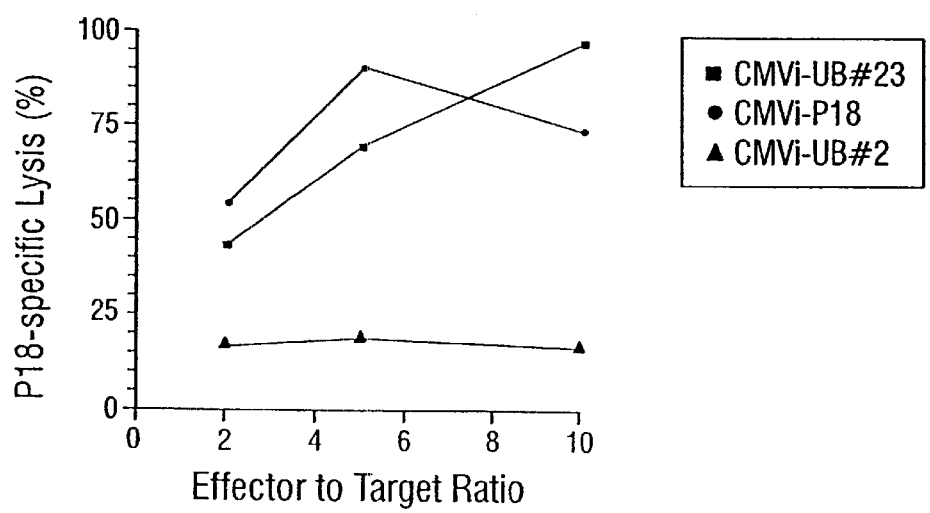
Figure 13A:
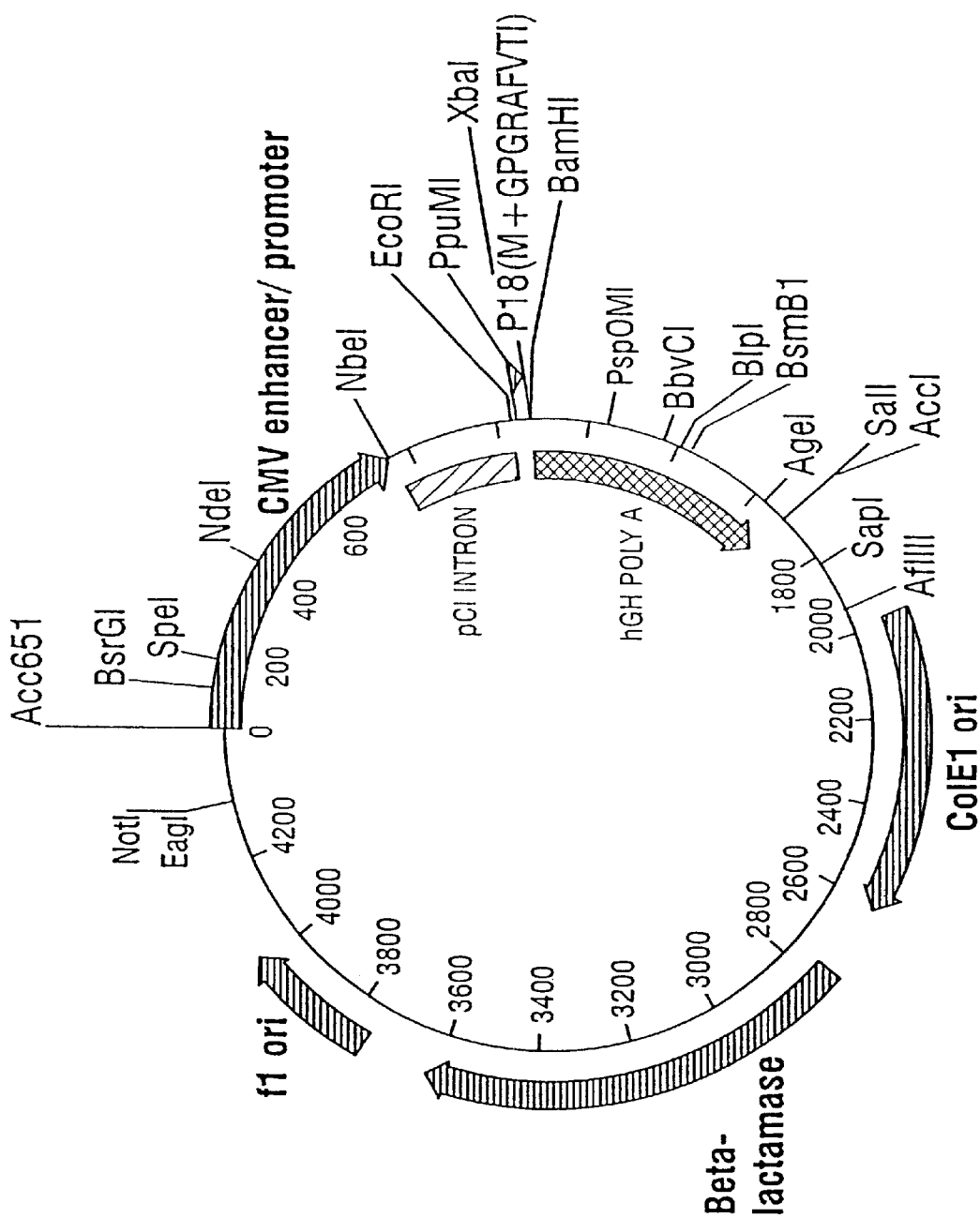
FIGS. 13A–F. Expression vector constructs encoding specific HIV peptide sequences. A. P18 construct. B. Peptide #61 construct. C. Peptide #63 construct. D. Peptide #104 construct. E. Peptide #111 construct. F. Peptide #113 construct.
Figure 13B:
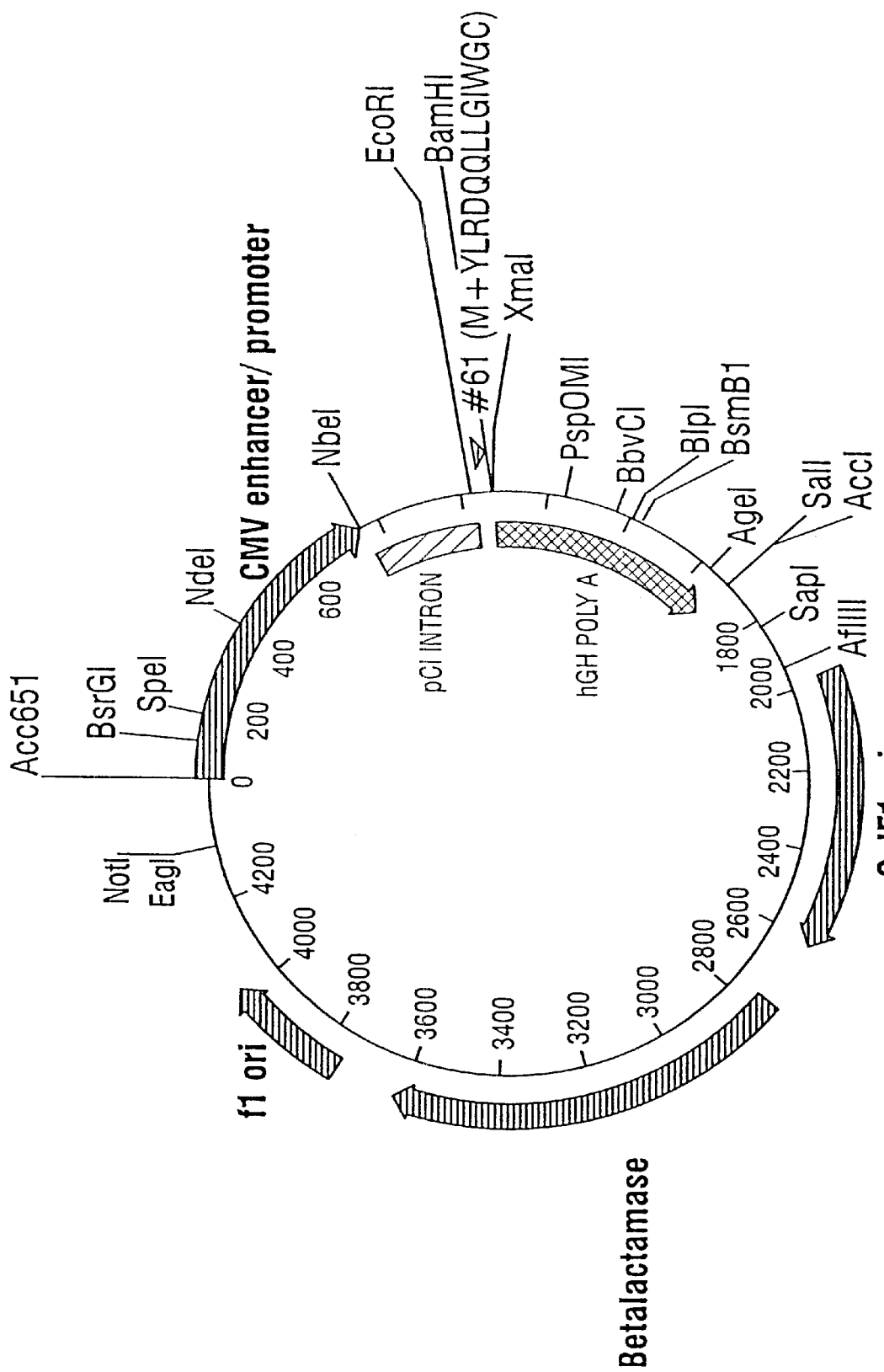
Figure 13C:
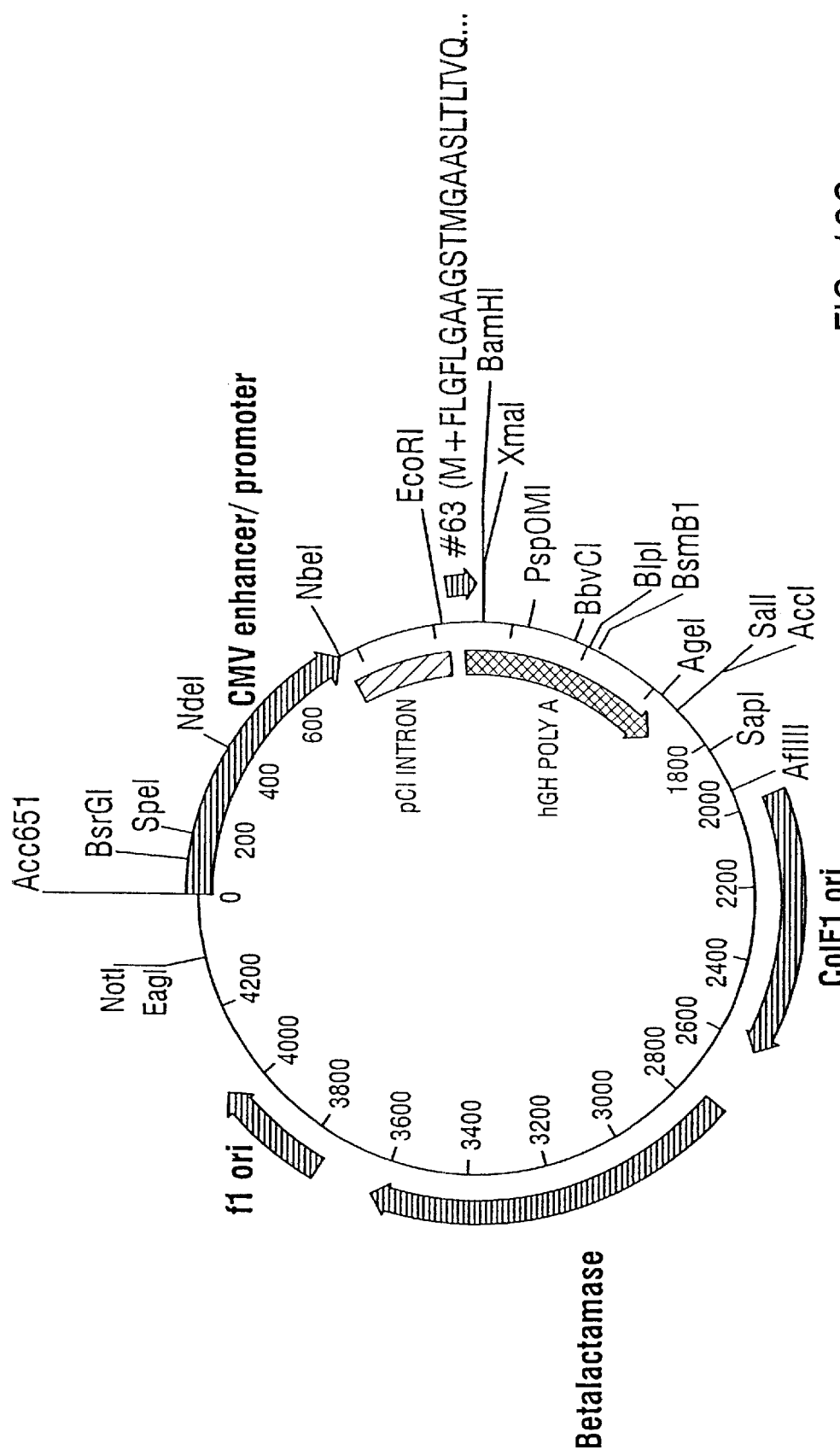
Figure 13D:
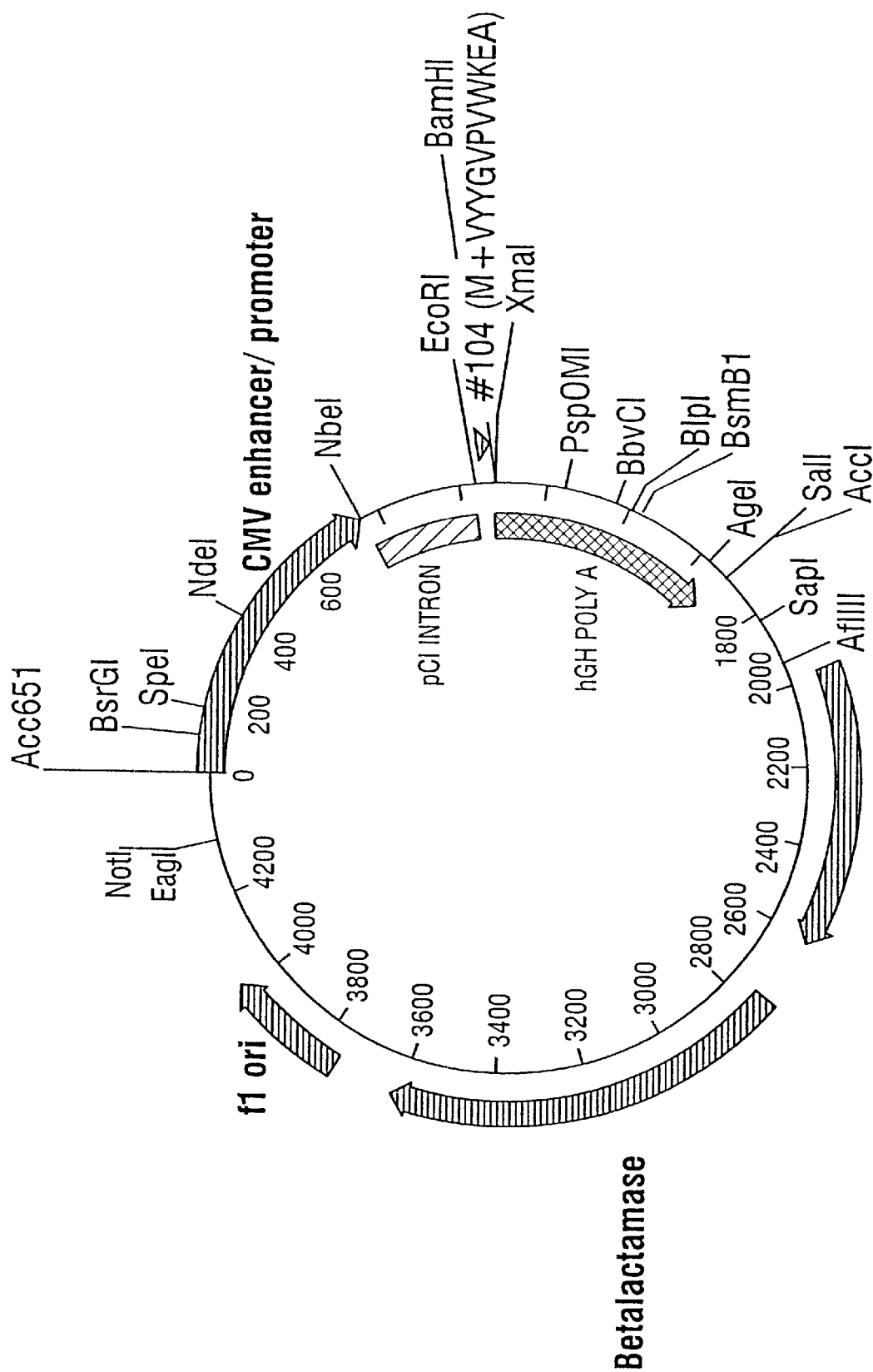
Figure 13E:
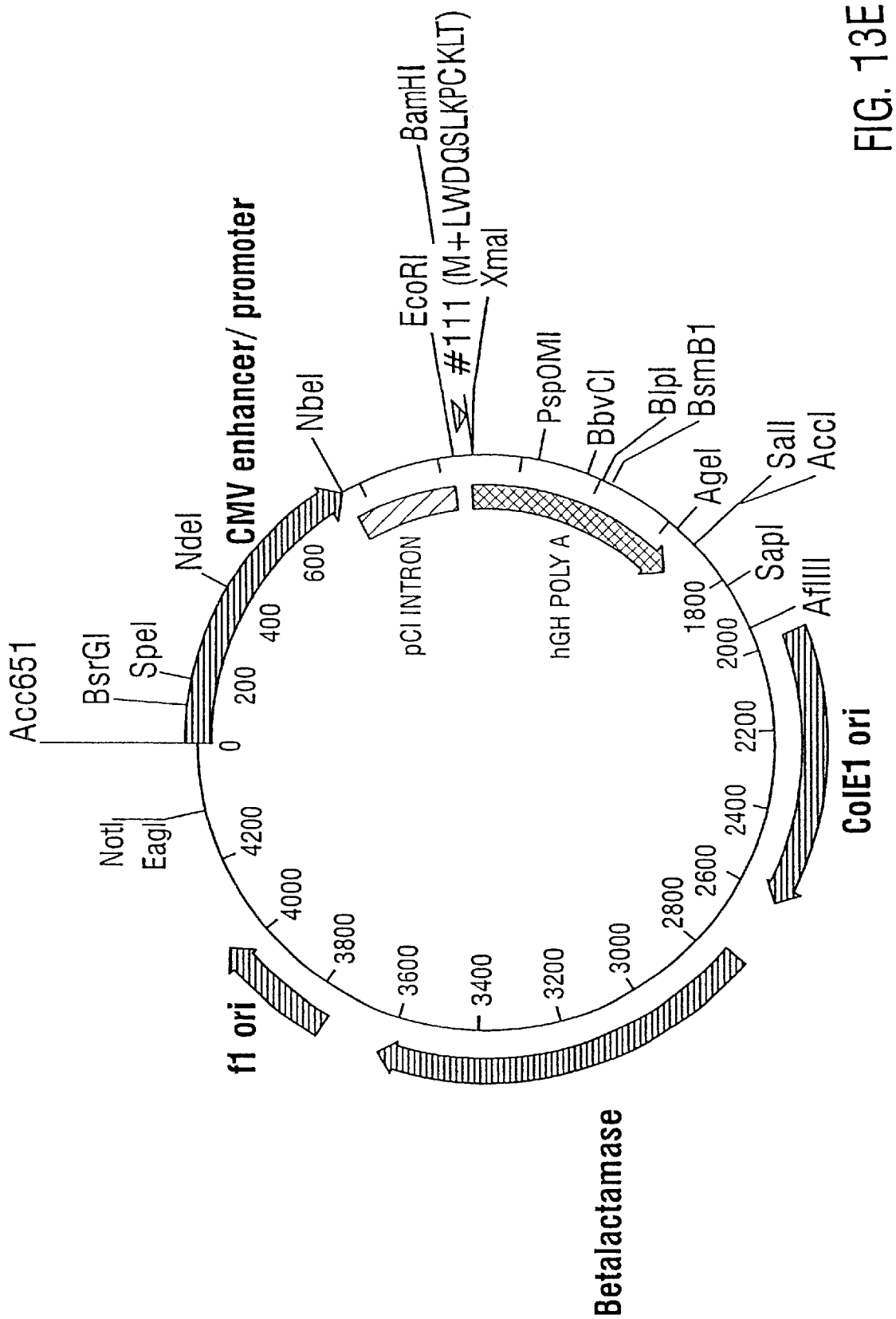
Figure 13F:
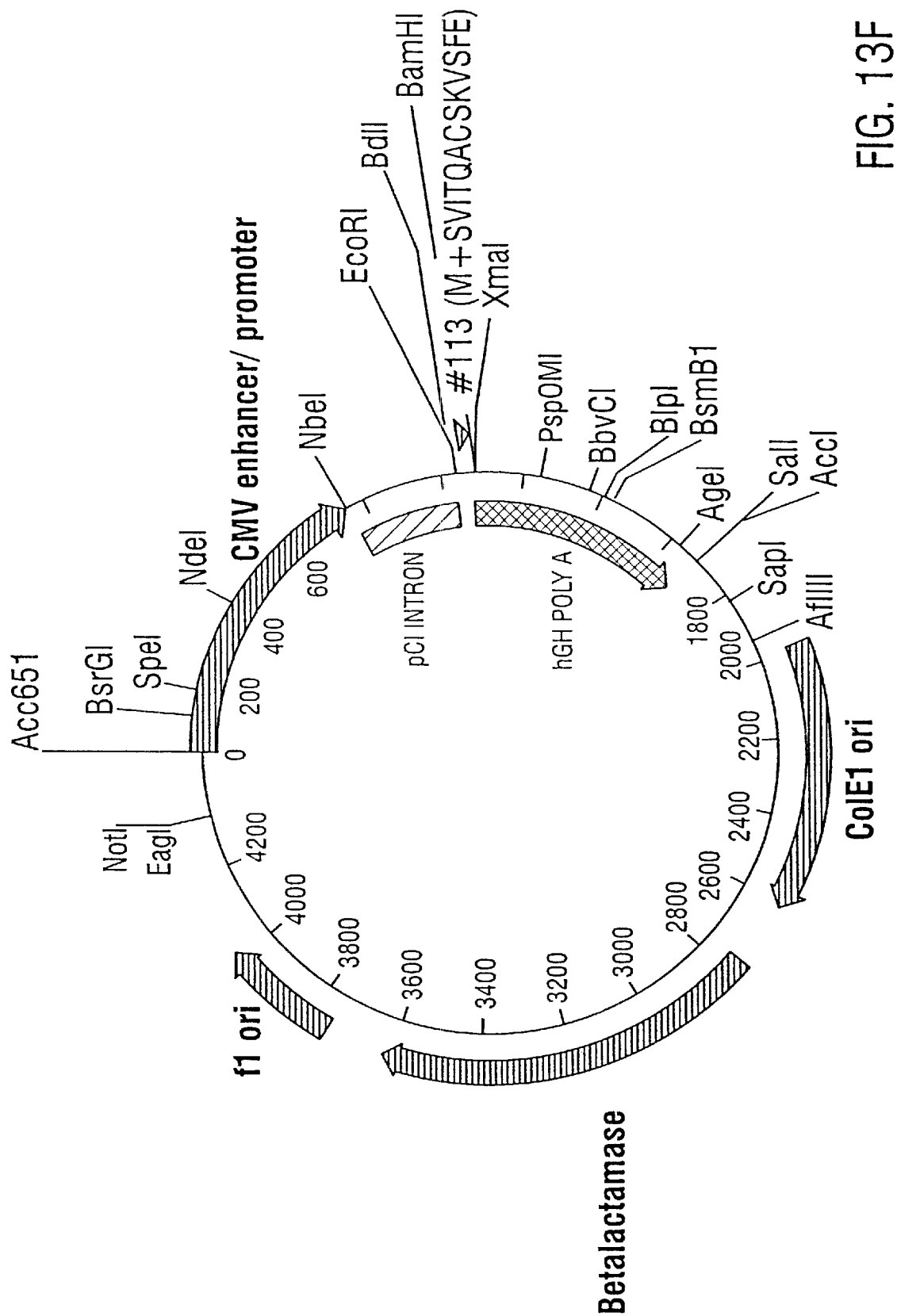

To do this, oligonucleotides were synthesized for each epitope to amplify the human growth hormone polyadenylation sequence with each epitope appended to the 5' of the poly A sequence (FIG. 12A). The oligo was such that each epitope is proceeded by an EcoRI site and a Kozak start methionine along with a stop codon immediately after the final amino acid of the peptide. Each of these epitope oligos was used in combination with an oligonucleotide specific for the 3' of the hGH poly adenylation sequence that has a BglII site added. Each epitope oligo will be amplified by PCR with Taq polymerase and gel purified with Qiaex II. The PCR product will then be digested with EcoRI and BglII, gel purified and ligated into the EcoRI and BamHI sites of the vector pG-CMVi (FIG. 12A). The resulting vector will have a cytomegalovirus enhancer/promoter, a 5' synthetic intron, a Kozak methionine, antigen epitope, stop codon, and hGH poly adenylation sequence for over-expression in mammalian cells. By this strategy peptides are produced in the cytoplasm where the methionine can be trimmed from the epitope for TAP translocation into the eridoplasmic reticulum (E.R.) and MHC I loading.

The constructs were first tested in mouse models for induction of Th and/or CTL responses. To do this, BALB/c mice were immunized by intramuscular (i.m.) injection with 10 µg of each plasmid purified from endotoxin-free Qiagen plasmid purification columns. These will be directly compared to mice immunized with synthetic peptide and adjuvant (Sastry, 1991; Sastry, 1992). The P18 mini-gene construct (FIG. 12B) will be used as a positive control. 14 days later one half of the mice will be sacrificed and Th and CTL activities will be assessed. The other half of the mice will be assayed at 60 days for memory T cell responses. These experiments assess: 1) the ability of the mini-gene constructs to elicit Th/CTL relative to the synthetic peptides in mice; and 2) indicate the efficacy of this method in other mammals.

If there is a problem with any of the cytoplasmic expression constructs, the peptide sequence will be transferred to the pSECi vector such that the antigen peptide will be fused immediately after the cleavage site for the α1-antitrypsin secretory leader. In this format, the peptide will be translated and secreted into the E.R. where the secretory leader will be removed thereby revealing the exact antigenic peptide. In this approach, the peptides avoid the addition of a heterologous methionine and avoid cytoplasmic proteolytic degradation. These second generation vectors will be tested in mice as described above. If the epitopes still fail, they will be fused downstream of ubiquitin (Barry, 1995). The ubiquitin can be poly-ubiquitinated thereby targeting the peptides to the proteasome for subsequent cleavage into peptides appropriate for TAP and MHC class I interactions. These constructs will be tested in mice as above. In some aspects of the invention, the methods can be performed by cotransfection of the mini-gene plasmids with plasmids encoding murine granulocyte-macrophage colony stimulating factor (Johnston, 1997) that enhances humoral as well as cellular immune responses as well as IL-12 that augments murine CTLs. Alternatively, the string of beads approach can be adopted where each MHC I epitope is fused to each other and also a heterologous T helper epitope is included to enhance immunogenicity (Ishioka, 1999).

For each construct, batches of 5–8 mice will receive the mini-gene vaccine at 10 μg, 100 μg, and 1 mg of plasmid. Mice in control batches will receive the equivalent synthetic peptide with adjuvant and in all groups of mice the peptide- and gp160-specific immune responses will be monitored at 14d and 60d time points as described above. Additionally, studies in the mouse model will include testing a cocktail of the plasmids, encoding each of the six highly conserved HIV envelope peptides, at the optimum concentration for priming of specific Th and CTL responses.

Results from the mouse studies will form the basis for testing the plasmid cocktail in the SHIV-rhesus model. A group of 8 monkeys will receive the optimal dose of the plasmid cocktail and 14 days after immunization, PBMCs will be harvested from the monkeys and tested for Th activity by the typical [$^3$H]thymidine incorporation assay, and against antigen-expressing and peptide-loaded autologous cells for CTL activity after in vitro restimulation. This time point should indicate relative levels of CTL priming by the constructs. Additionally, 60 days after immunization, PBMC from the monkeys will be tested for Th and CTLs again as an indication of the level of T cell memory that has been established over a moderate period. The monkeys will then be boosted with the same amount of DNA and CTLs measured at 14 and 60 days to determine if the booster has any effect. The monkeys will be boosted only once to avoid "over-dosing" the animals with DNA and attenuating the responses. If CTL responses are minimal after one boost, one additional boost with the same time line will be attempted. Once the CTL correlate measurements are complete, each monkey will be challenged with SHIV as described in the preliminary results section. Viral titers will be assessed over subsequent weeks by RT-PCR for the viral genome, and infectious center assays.

Example 10

Synthetic Peptide Vaccines for Mucosal Immunization of Mice

HIV synthetic peptides were effective for mucosal immunization and induction of specific immune responses in the mucosal and systemic compartments. These studies involved immunizing Balb/c or C57B1/6 mice by the intranasal route, 4 times at weekly intervals, with synthetic peptides that we reported earlier to function as CTL-inducers and also as epitopes. Two peptides from the V3 loop region in the envelope protein of different HIV strains were chosen, and one peptide from the E6 oncoprotein of human papillomavirus type 16 (HPV-16). Initially, cholera toxin (CT, 1 μg/mouse) was used as the mucosal adjuvant and data was obtained showing induction of specific CTL responses. These responses were observed with as little as two doses of the peptide in CT.

Because of toxicity issues, further experiments using mutated forms of the CT and Act were conducted. For these experiments the CTL epitope peptide from the V3 loop of HIV-1 IIIB was used. Mice were immunized, 4 times at weekly intervals, by the intranasal route with the peptide in Act (1 μg/mouse). The spleen and cervical lymph node cells were harvested and tested for CTL activity after in vitro restimulation for 5 days with the peptide. Efficient CTL activity was evident in both the cell populations indicating the induction of specific CTL activity in both the mucosal and systemic compartments. Also tested was another peptide from the amino-terminal region of HIV gp160 that had been reported to be capable of inducing specific proliferative responses (Sastry, 1991). In this case, the peptide was emulsified in CFA and injected into the hind foot pad of the mouse, or mixed with heat-inactivated Act and introduced by the intranasal route. In case of foot pad immunization the popliteal lymph node cells, and in the case of intranasal immunization the spleen and cervical lymph node cells were tested and observed to be positive for proliferative responses to the peptide.

Other experiments will be conducted to investigate the adjuvant activity of CT and Act mutants in conjunction with the therapeutic and preventative therapies of the claimed invention. The mutated form of CT was designated as CT2* in which amino acid residues Arg7 and Glu112 within the enzymatic active A subunit of CT were substituted for Lys and Gln, respectively. The mutated toxin was purified by another group to homogeneity level, and unlike native CT, the CT2* was devoid of its ability to evoke fluid secretion in the ligated small intestinal loops of rabbits. In addition, the lavage fluid of the CT2* (1 µg) challenged loops contained basal level of 3'5'-adenosine monophosphate (cAMP) and prostaglandin ($PGE_2$) levels. On the contrary, the ligated loops challenged with native CT (1 µg) evoked a significant fluid secretory response (1.9 ml/cm of the loop) with a 4–5 fold increase in the cAMP and $PGE_2$ levels in the loop fluid. These data clearly indicated that mutated CT (CT2*) would not have any safety problems. Although one can utilize only the binding subunit of CT (CTB) as a mucosal adjuvant, the mutated intact CT will be used.

A heat-inactivated form of Act demonstrated its capacity to function' as an adjuvant for priming CTL responses by an HIV peptide when introduced into mice by the intranasal route. In addition, a mutated form of Act was generated by another group, in which a substitution of amino acid residue Trp394 with phenylalanine resulted in mutated form of Act that can be used in conjunction with the present invention.

Experiments will be performed with mutated forms of the CT and Act for testing their capacity to serve as mucosal adjuvants to administer the HIV envelope peptide cocktail by the intranasal route for priming specific Th and CTL responses in mice. Based on results from these preliminary studies, a primate study will be designed for intranasal immunization for priming specific cellular immune responses. In the SHIV-rhesus model, only the mutated toxin that is more potent as a mucosal adjuvant will be utilized.

Based on the outcome of the studies in mice, one of the mutated toxin preparations will be chosen and the study will begin in monkeys for mucosal vaccination with the peptides by the intranasal route followed by challenge with SHIV by the intravaginal route. Because several reports in the literature described successful priming of immune responses when the antigen was introduced into mice by the intravaginal route, mice given the antigen (admixed with the selected mutant toxin) by the intravaginal route will be tested and monitored for immune responses.

For the mucosal immunization studies in mice, a vaccination regimen was followed that included four weekly intranasal doses of the peptide (1 ug) in CT and one week later harvesting the spleen and draining cervical lymph node cells for determining the immune responses. A similar regimen will be adopted for the immunization of the monkeys (n=8), but the vaccine will be administered four times at two-week intervals followed by two monthly dosings (10 ug toxin/monkey). The method for intranasal immunization of the monkeys will be as described by Imaoka et al. In this procedure, the monkeys will be anesthetized with ketamine and placed in dorsal recumbancy with head tilted back so that the nares are pointed upward. The vaccine solution (0.5 ml) will be instilled drop-wise into each nostril without inserting the syringe into the nasal cavity. The monkeys will be kept in this position for 10 min and then placed in lateral recumbancy until they have recovered from anesthesia. The immunological monitoring, SHIV challenge and subsequent testing for protective responses will be as described above in the design for studies in specific aim 1. As stated above, murine studies will be performed to determine the potential of intravaginal administration of the peptide cocktail for generating efficient and specific immune responses. Based on the results from these studies, a decision will be made to conduct the SHIV-rhesus study (in a group of 8 animals) for administering the peptide cocktail by direct injection of four equal portions of the vaccine at four equidistant quadrants using a 22 gauge needle. A series of four injections at two-week intervals will be followed by two monthly doses of the peptide cocktail (each peptide at 100 ug/dose in 1 ml saline). The immunological monitoring will be for at least six months before challenging with SHIV by the intravaginal route and a further follow-up for one year as described above.

Blood samples will be collected at two-week intervals to monitor the immune responses. Additionally, biopsies of draining lymph nodes will be obtained two weeks after the final dosing to determine the local immune responses. The lymph nodes responding to the intranasal administration will be from the submandibular and the upper deep cervical regions. Those nodes specific to the intravaginal route will be from the nodes in the inguinal region (either the superficial or deep chains). Subsequent to the SHIV challenge of the animals, the virological testing will be done using the same lymphoid regions of the animals, but from the contralateral side to those previously sampled.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents, which are both chemically and physiologically related, may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,367,110
U.S. Pat. No. 4,452,901
U.S. Pat. No. 4,554,101
U.S. Pat. No. 4,578,770
U.S. Pat. No. 4,596,792
U.S. Pat. No. 4,599,230
U.S. Pat. No. 4,601,903
U.S. Pat. No. 4,608,251
U.S. Pat. No. 4,683,195
U.S. Pat. No. 4,683,202
U.S. Pat. No. 4,690,915
U.S. Pat. No. 4,797,368
U.S. Pat. No. 4,800,159
U.S. Pat. No. 4,883,750
U.S. Pat. No. 5,028,592
U.S. Pat. No. 5,139,941
U.S. Pat. No. 5,199,942
U.S. Pat. No. 5,221,605
U.S. Pat. No. 5,238,808
U.S. Pat. No. 5,279,721
U.S. Pat. No. 5,310,687
U.S. Pat. No. 5,620,896
U.S. Pat. No. 5,958,895
EPA No. 320 308
EPA No. 329 822

GB Application No. 2 202 328
PCT Application No. PCT/US87/00880
PCT Application No. PCT/US89/01025
PCT Application WO 88/10315
PCT Application WO 89/06700
WO 90/07641
Ada and Jones, *Curr. Top. Microbiol. Immunol.*, 1986.
Aichele et al., *J. Exp. Med.*, 171:1815–1820, 1990.
Altman et al., *Science*, 274:94–96, 1996.
An L-L and Whitton, *J. Virol.*, 71:2292–2302, 1997.
Ariizumi, Kitajima, Bergstresser, Takashima, *Eur. J. Immunol.*, 25:2137–2141, 1995.
Baichwal et al., "Vectors for gene transfer derived from animal DNA viruses: Transient and stable expression of transferred genes," In: *Gene Transfer*, Kucherlapati, R., ed., Plenum Press, New York, pp. 117–148, 1986.
Barany and Merrifield, "Solid-Phase Peptide Synthesis," In: *The Peptides: Analysis, Synthesis, Biology*, Gross and Meinhofer, eds., Academic Press, New York, pp. 3–284, 1980.
Barry et al., *Nature*, 377:632–635, 1995.
Berzofsky, *FASEB J.*, 5:2412–2418, 1991.
Bevan, *Nature*, 342:478–479, 1989.
Bjorkman and Parham, *Ann. Rev. Biochem.*, 59:253–288, 1990.
Bjorling et al. *AIDS* 6:1259–1264, 1996.
Bogedain et al., *J. Virol.*, 69:48724879, 1995.
Boussif et al., *Proc. Nat'l Acad. Sci. USA*, 92:7297–7301, 1995.
Boyson et al. *J. Immunol.* 156:4656–4665, 1996.
Braciale et al., *Immonul. Rev.*, 98:95–114, 1987.
Brutlag et al., *CABIOS*, 6:237–245, 1990.
Callebaut et al., *Science*, 262:2045–2050, 1993.
Capaldi et al., *Biochem. Biophys. Res. Comm.*, 76:425 1977.
Carmichael et al., *J. Exp. Med.*, 177:249–256, 1993.
Casement et al., *Virology*, 211(1):261–67, 1995.
Caux et al., *J. Exp. Med.*, 180:1263–1272, 1994.
Chang et al., *Hepatology*, 14:134A, 1991.
Chen and Okayama, *Mol. Cell Biol.*, 7:2745–2752, 1987.
Chenciner et al., *Eur. J. Immunol*, 19:1537–1544, 1989.
Chopra et al., *Gene* 139:87–91, 1994.
Chopra et al., *Microbial Path.* 21:357–377, 1996.
Ciernik et al., *J. Immunol.*, 156:2369–2375, 1996.
Clark et al., *Human Gene Therapy*, 6:1329–1341.
Clerget-Raslain et al., *Res. Virol.*, 142:423–438, 1991.
Clerici et al., *J. Infect. Dis.*, 164:178–182, 1991.
Coffin, In: *Virology*, Fields et al., eds., Raven Press, New York, pp. 1437–1500, 1990.
Cong et al., *J. Immunol.* 158:3936–3946, 1997.
Coupar et al., *Gene*, 68:1–10, 1988.
Dadaglio et al., *J. Immunol.*, 147:2302–2309, 1991.
Dai et al., *J. Virol.*, 66:3151–3154, 1992.
Del Guercio et al., Vaccine 15:441–448, 1997.
De Rossi et al., *Virology*, 184:187–196, 1991.
Deres et al., *Nature*, 342:561–564, 1989.
Dill et al., *Proc. Nat'l Acad. Sci. USA*, 85:5664–5668, 1988.
Dull et al., *J. Virol.*, 72:8463–8471, 1998
Dupuis et al., *J. Immunol.*, 155:2232–2239, 1995.
Enk and Katz, *Proc. Nat'l Acad. Sci. USA*, 89;1398–1402, 1992.
Falk et al., *J. Exp. Med.*, 182:1005–1018, 1995.
Falk et al., *Proc. Nat'l Acad. Sci. USA*, 90:12005–12009, 1993.
Fechheimer et al., *Proc. Nat'l Acad. Sci. USA*, 84:8463–8467, 1987.
Ferguson et al., *Gene* 156:79–83, 1995.
Ferguson et al., *Infect. Immun.* 65:4299–4308, 1997.
Fetrow and Bryant, *Biotechnology*, 11:479–483, 1993.
Flotte et al., *Gene Therapy*, 2:29–37, 1995.
Flotte et al., *Proc. Nat'l. Acad. Sci. USA* 90:10613–10617, 1993.
Flotte, et al., *Am. J. Respir. Cell Mol. Biol.*, 7:349–35,6, 1992.
Fraley et al., *Proc. Nat'l Acad. Sci. USA*, 76:3348–3352, 1979.
Freshney "Animal cell culture: a practical approach, Oxford (England); New York: IRL Press, Oxford University Press, 1992.
Friedmann, *Science*, 244:1275–1281, 1989.
Frohman, *PCR PROTOCOLS: A GUIDE TO METHODS AND APPLICATIONS*, Academic Press, New York, 1990.
Fuller and Haynes, *AIDS Res. Hum. Retroviruses*, 11:1433–1441, 1994.
Gallichan et al., *J. Exp. Med.* 181:1879–1890, 1996.
Gasson et al., *Immunogenetics*, 25:313–322, 1987.
Gopal, *Mol. Cell Biol.*, 5:1188–1190, 1985.
Graham and van der Eb, *Virology*, 52:456–467, 1973.
Graham et al., *J. Gen. Virol.*, 36:59–72, 1977.
Grunhaus and Horwitz, *Seminar in Virology*, 3:237–252, 1992.
Harland and Weintraub, *J. Cell Biol.*, 101:1094–1099, 1985.
Haynes et al., *Science*, 274:324–328, 1996.
Hermonat and Muzyczka, *Proc. Nat'l Acad. Sci. USA*, 81:6466–6470, 1984.
Heufler et al., *J. Exp. Med.*, 176:1221–1226, 1992.
Horwich et al. *J. Virol.*, 64:642–650, 1990.
Houghten, R. A. *Proc. Nat'l Acad. Sci. USA*, 82:5131–5135, 1985.
Howes et al., *Nature*, 277:67, 1979.
Imaoka et al., *J. Immunol.*, 161:5952–5958, 1998.
Ishioka et al., *J. Immunol.*, 162:3915–3925, 1999.
Jameson and Wolf, *Comput. Appl. Biosci.*, 4(1):181–186, 1988.
Jassoy et al., *J. Immunol.*, 149:3113–3119, 1992.
Johnson et al., *J. Exp. Med.*, 175:961–971, 1992.
Johnson et al., *J. Virol.*, 67:438–445, 1993.
Johnston et al., Boehm, ed. Marcel Dekker, Inc., New York, p. 1–8, 1997.
Kaplitt et al., *Nature Genetics*, 8:148–154, 1994.
Kast et al., *Proc. Nat'l Acad. Sci. USA*, 88:2283, 1991.
Keusch et al., *J. Infect. Dis.* 131:58–63.
Kitajima et al., *J. Immunol.*, 155:3794–3800, 1995.
Klein et al., *J. Exp. Med.*, 181:1365–1372, 1995.
Klein, *Natural History of the Major Histocompatibility Complex*, John Wiley & Sons, New York, pp. 775, 1986.
Kotin et al., *Proc. Nat'l Acad. Sci. USA*, 87:2211–2215, 1990.
Koup et al., *J. Virol.*, 68:4650–4655, 1994.
Kyte and Doolittle, *J. Mol. Biol.*, 157:105–132, 1982.
LaFace et al., *Viology*, 162:483–486, 1988.
Laughlin et al., *J. Virol.*, 60:515–524, 1986.
Lebkowski, et al., *Mol. Cell. Biol.*, 8:3988–3996, 1988.
Levy, *Microbiol. Rev.*, 57:183, 1993.
Lifson et al., *J. Infect. Dis.*, 163:959–965, 1991.
Littaua et al., *J. Virol.*, 65:4051–4056, 1991.
Lukacher et al., *J. Exp. Med.*, 160:814–826, 1984.
Lu et al., *Virology*, 209:147–154,1995.
Luo et al., *Blood*, 82: suppl. 1:303A, 1994.
Lycke et al., *Scand. J. Immunol.* 23:611–616, 1986.
Mann et al., *Cell*, 33:153–159, 1983.
Matsue et al., *J. Invest. Dermatol.*, 99:537–541, 1992.
McCarty et al., *J. Virol.*, 65:2936–2945, 1991.
McLaughlin et al., *J. Virol.*, 62:1963–1973, 1988.
McMichael et al., *Nature*, 270:524–546, 1977.

Merino et al., *Int'l. J. Food. Microbiol.* 28:157–168, 1995.
Merrifield, R. B., *J. Am. Chem. Soc.*, 85:2149–2154, 1963.
Mizrahi, *Process Biochem.*, (August):9–12, 1983.
Modrow et al., *J. Virol.* 61:570–578, 1987.
Mohamadzadeh et al., *J. Immunol.*, 156:3102–3106, 1996.
Mortara et al., *J. Virol.* 73:4447–4451, 1999.
Munoz et al., *J. Acquired Immune Syndr. Hum. Retroviruses*, 8:496–505, 1995.
Musey et al., *New Engl. J. Med.*, 337:1267–1274, 1997.
Muzyczka, N., *Curr. Top. Microbiol. Immunol.*, 158:97–129, 1992.
Naldini et al., *Science*, 272:263–267, 1996.
Nehete et al., *AIDS Res. Hum. Retroviruses*, 9:235–240, 1993.
Nehete et al., *Vir. Immunol.*, 7:189, 1994.
Nehete et al., *AIDS* 9:567–572, 1995.
Nehete et al., *Cell. Immunol.*, 160:217, 1995.
Nehete et al., *J. Clin. Immunol.*, 16:115–124, 1996.
Nehete et al., *Vir. Immunol.*, 11:119–129, 1998.
Nehete et al., *Vir. Immunol.*, 11:147–158, 1998.
Nicolas and Rubinstein, "Retroviral vectors," In: *Vectors: A survey of molecular: cloning vectors and their uses*, Rodriguez and Denhardt, eds., Butterworth, Stoneham, England, pp. 494–513, 1988.
Nicolau and Sene, *Biochem. Biophys. Acta*, 721:185–190, 1982.
Nixon et al., *Nature* 336:484–487, 1988.
Ohi et al., *Gene*, 89:279–282, 1990.
Olerum and Zetterquist, *Tissue Antigens*, 39:225–235, 1992.
Paltaleo et al., *J. Immunol*, 144:1696, 1990.
Pantaleo et al., *Nature*, 370:463–467, 1994.
Paskind et al., *Virology*, 67:242–248, 1975.
Peterson et al., *Infect. Immunol.* 67:794–799, 1999.
Phillips et al., In: *Large Scale Mammalian Cell Culture*, Feder, J. and Tolbert, W. R., eds., Academic Press, Orlando, Fla., 1985.
Picard et al., *J. Acquired Immune Defic. Syndr.*, 5:539–546., 1992.
Pierce, *Infect. Immunol.* 158:341–346, 1984.
Plata et al., *Nature*, 328:348–351, 1987.
Pontesilli et al., *Clin. Exp. Immunol.*, 100:419–424, 1995.
Porgador et al., *J. Immunol.* 158:834–841, 1997.
Potter et al., *Proc. Nat'l Acad. Sci. USA*, 81:7161–7165, 1984.
Ratner et al., *Nature* 313:277–284, 1985.
Ridgeway, "Mammalian expression vectors," In: *Vectors: A survey of molecular cloning vectors and their uses.*, Rodriguez R. L., Denhardt D. T., eds., Butterworth, Stoneham, England, pp. 467–492, 1988.
Rinaldo et al., *J. Virol.*, 69:5838–5842, 1995.
Rippe et al., *Mol. Cell Biol.*, 10:689–695, 1990.
Roos et al., *J. Infect. Dis.*, 171:531–536, 1995.
Rosenberg et al., *Science*, 278:1447–1450, 1997.
Roux et al., *Proc. Nat'l Acad. Sci. USA*, 86:9079–9083, 1989.
Rowland-Jones et al., *Lancet*, 341:860–861, 1993.
Rowland-Jones et al., *Nature Med.*, 1:59–64, 1995.
Sambrook, et al., *Molecular Cloning, A Laboratory Manual*, 2nd ed., Cold Spring Harbor Laboratory, Cold Spring, Harbor, N.Y., 1989.
Samulski et al., *EMBO J.*, 10:3941–3950, 1991.
Samulski et al., *J. Virol.*, 63:3822–3828, 1989.
Sastry and Arlinghaus, *AIDS*, 5:699–707, 1991.
Sastry et al., *Viral Immunol.*, 8(3):165–74, 1994.
Sastry et al., *Virology*, 188:502–509, 1992.
Schendel et al., *J. Immunol.*, 149:2406–2416, 1992.
Schreiber et al., *J. Immunol.*, 149:3525–3534, 1992.
Schrier et al., *J. Immunol.*, 142:1166–1176.
Sedegah et al., *Imunology*, 91:9866–9870, 1994.
Shelling & Smith, *Gene Therapy*, 1:165–169, 1994.
Sodoyer et al., *EMBO J.*, 3:879–885, 1984.
Steinman, *Ann. Rev. Immunol.*, 9:271–296, 1991.
Steinman, Inaba, Schuler, In: *The Immune Functions of Epidermal Langerhans Cells*, Heidrun Moll, ed., R. G. Landes Company, Austin, Tex., pp. 1–1 9, 1995.
Stratford-Perricaudet and Perricaudet, In: *Human Gene Transfer*, O. Cohen-Haguenauer and M. Boiron, eds., John Libbey Eurotext, France, p. 51–61, 1991.
Takahashi et al., *Proc. Natl. Acad. Sci. USA*, 88:10277–102, 1991.
Tam et al., *J. Am. Chem. Soc.*, 105:6442, 1983.
Temin, "Retrovirus vectors for gene transfer: Efficient integration into and expression of exogenous DNA in vertebrate cell genome," In: *Gene Transfer*, Kucherlapati, ed., Plenum Press, New York, pp. 149–188, 1986.
Tooze, J., ed., *Molecular Biology of DNA Tumor Viruses*, 2nd ed., Cold Spring Harbor Laboratory, Cold Spring Harbor, N.Y., 1991.
Townsend and Bodmer, *Annu. Rev. Immunol.*, 7:601–624, 1989.
Townsend et al., *Cell*, 44:949–968, 1986.
Tratschin et al., *Mol. Cell. Biol.*, 4:2072–2081, 1984.
Tratschin et al., *Mol. Cell. Biol.*, 5:32581–3260, 1985.
Trowsdale, *Trends Genet.*, 9:117–122, 1993.
Tsubota et al., *J. Exp. Med.*, 169:1421–1434, 1989.
Tur-Kaspa et al., *Mol. Cell Biol.*, 6:716–718, 1986.
Ulmer et al., *Science*, 259:1745–1749, 1993.
Unanue & Cerottini, *FASEB J.* 3:2496–2502, 1989.
van den Eynde et al., *J. Exp. Med.*, 182:689–698, 1995.
Walker et al., *Science*, 234:1563, 1986.
Walker et al., *Nature*, 328:345–348, 1987.
Walker et al., *Science*, 240:64–66, 1988.
Walsh et al., *Proc. Nat'l Acad. Sci. USA*, 89:7257–7261, 1994.
Wang et al., *Infec. Imm.*, 66:4193–4202, 1998.
Wei et al., *Gene Therapy*, 1:261–268, 1994.
Weinberger et al., *Science*, 228:740–742, 1985.
Wigler et al., *Proc. Nat'l Acad. Sci. USA*, 77:3567, 1980.
Wolf et al., *Comput. Appl. Biosci.*, 4(1):187–191, 1988.
Wu and Wu, *Biochemistry*, 27:887–892, 1988.
Wu and Wu, *J. Biol. Chem.*, 262:4429–4432, 1987.
Xiang et al., *Virology*, 199:132–140, 1994.
Xu et al., *Infect. Immun.* 66:3501–3509, 1998.
Yamada et al., *Epidemiol. & Infect.* 119:121–126,1997.
Yang et al., *J. Virol.*, 68:4847–4856, 1994.
Yang et al., *Proc. Natl'l Acad. Sci. USA*, 87:9568–9572, 1990.
Yasutomi et al., *J. Virol.*, 70:678–681, 1996.
Yoder et al., *Blood*, 82: suppl. 1:347A, 1994.
Yokoyama et al., *J. Virol.*, 69:2684–2688, 1995.
Zemmour and Parham, *Immunogenetics*, 37:239–250, 1993.
Zhou et al., *Exp. Hematol. (NY)*, 21:928–933, 1993.
Zhou et al., *J. Exp. Med.*, 179:1867–1875, 1994.

What is claimed is:

1. A method of treating an HIV infection in a human subject comprising administering to said subject a synthetic peptide composition comprising at least the sequence of SEQ ID NO:20, 21, 22, 23, 24, 25 or 40.

2. The method of claim 1, further comprising determining whether said subject exhibits an HLA-Cw7-restricted CTL response.

3. The method of claim 1, wherein synthetic HIV peptides of the composition comprise up to 50 residues.

4. The method of claim 3, wherein synthetic HIV peptides of the composition are 11 to 25 residues in length.

5. The method of claim 4, wherein said synthetic peptides are 11 to 25 residues in length and comprise the sequences:
   (a) SEQ ID NO:26, 27, 28, 29, 30, 31, 32, 33 or 34;
   (b) SEQ ID NO:20, 21, 22, 23, 24, 25 or 40; and
   (c) SEQ ID NO:1, 2 or 3.

6. The method of claim 1 wherein said composition is fixer defined as comprising a plurality of HIV peptides, wherein said composition further comprises an HIV peptide having the sequence:

(a) SEQ ID NO:26, 27, 28, 29, 30, 31, 32, 33 or 34; or
   (b) SEQ ID NO:1, 2 or 3.

7. The method of claim 1, wherein the composition further comprises one or more synthetic peptides comprising the sequences:
   (a) SEQ ID NO:8, 9, 10, 11, 12, 13, 14, 15 or 38; or
   (b) SEQ ID NO:16, 17, 18, 19 or 39.

8. The method of claim 6, wherein the plurality of HIV peptides comprises three different peptides comprising, individually, the sequences:
   (a) SEQ ID NO:26, 27, 28, 29, 30, 31, 32, 33 or 34;
   (b) SEQ ID NO:20, 21, 22, 23, 24, 25 or 40; and
   (c) SEQ IM NO:1, 2 or 3.

9. The method of claim 8, wherein the plurality of HIV peptides comprises four different peptides comprising, individually, the sequences:
   (a) SEQ ID NO:26, 27, 28, 29, 30, 31, 32, 33 or 34;
   (b) SEQ ID NO:20, 21, 22, 23, 24, 25 or 40;
   (c) SEQ ID NO:1, 2 or 3; and
   (d) SEQ ID NO:4, 5, 6, 7, 8, 9, 10, 11, 12, 13, 14, 15, 38, 16, 17, 18, 19 or 39.

10. The method of claim 9, wherein the plurality of HIV peptides comprises five different peptides comprising, individually, the sequences:
  (a) SEQ ID NO:26, 27, 28, 29, 30, 31, 32, 33 or 34;
  (b) SEQ ID NO:20, 21, 22, 23, 24, 25 or 40;
  (c) SEQ ID NO:1, 2 or 3;
  (d) SEQ ID NO:4, 5, 6 or 7; and
  (e) SEQ ID NO:8, 9, 10, 11, 12, 13, 14, 15, 38, 16, 17, 18, 19 or 39.

11. The method of claim 10, wherein the plurality of HIV peptides comprises six different peptides comprising, individually, the sequences:
  (a) SEQ ID NO:26, 27, 28, 29, 30, 31, 32, 33 or 34;
  (b) SEQ ID NO:20, 21, 22, 23, 24, 25 or 40;
  (c) SEQ ID NO:1, 2 or 3;
  (d) SEQ ID NO:4, 5, 6, or 7;
  (e) SEQ ID NO:8, 9, 10, 11, 12, 13, 14, 15 or 38; and
  (f) SEQ ID NO:16, 17, 18, 19 or 20.

12. The method of claim 1, wherein said HIV peptide or peptides are coupled to a carrier molecule.

13. The method of claim 12, wherein said carrier molecule is KLH or BSA.

14. The method of claim 1, wherein said composition further comprises an adjuvant.

15. The method of claim 14, wherein said adjuvant is selected from a group consisting of lipids, toxins, cytokines, oligonucleotides and bacterial DNA.

16. The method of claim 1, further comprising administering AZT to said subject.

17. The method of claim 1, further comprising carrying out HAART on said subject.

18. The method of claim 2, wherein the subject does not exhibit an HLA-Cw7-restricted CTL response, further comprising:
  (c) determining if the subject expresses the HLA-Cw7 haplotype; and if so,
  (d) eliciting said response.

19. The method of claim 18, wherein eliciting said response comprises administering to said subject a therapeutically effective amount of $\alpha$- or $\gamma$-interferon, whereby the level of HLA-Cw7 haplotype expression increases.

20. The method of claim 18, wherein determining expression of the HLA-Cw7 haplotype comprises a serological assay using an antibody that recognizes an HLA-Cw7 epitope.

21. The method of claim 18, wherein determining expression of the HLA-Cw7 haplotype comprises performing a nucleic acid amplification reaction, wherein a region within the coding sequence of HLA-Cw7 is amplified.

22. The method of claim 1, wherein the HIV is HIV-1.

23. The method of claim 1, wherein the composition is injected into the subject intradermally or subcutaneously.

24. The method of claim 1, wherein the composition is administered more than one time.

25. The method of any claims 1, 2, 3–6, 7–22, 23, 24 wherein the treatment resulted in preventing an HIV-infected subject from developing AIDS.

* * * * *

UNITED STATES PATENT AND TRADEMARK OFFICE
CERTIFICATE OF CORRECTION

PATENT NO. : 6,656,471 B1
DATED : December 2, 2003
INVENTOR(S) : K. Jagannadha Sastry, Ralph B. Arlinghaus and Pramod N. Nehete It is certified that error appears in the above-identified patent and that said Letters Patent is hereby corrected as shown below:

<u>Column 79,</u>
Line 65, please delete "fixer" and insert -- further -- therefor.

<u>Column 80,</u>
Line 59, please delete "IM" and insert -- ID -- therefor.

<u>Column 82,</u>
Line 27, after "any" please insert -- one of -- therefor.
Line 28, please delete "resulted" and insert -- results -- therefor.

Signed and Sealed this

Ninth Day of March, 2004

JON W. DUDAS
*Acting Director of the United States Patent and Trademark Office*